(12) United States Patent
Kosma et al.

(10) Patent No.: US 8,476,315 B2
(45) Date of Patent: Jul. 2, 2013

(54) N-HYDROXY C29-AMIDE DERIVATIVES OF OLEANDRANE

(75) Inventors: Paul Kosma, Vienna (AT); Ulrich Jordis, Vienna (AT); Dirk Classen-Houben, Vienna (AT); Bernhard Kueenburg, Vienna (AT); Christian Stanetty, Vienna (AT); Laszlo Czollner, Ebenfurth (AT)

(73) Assignee: Onepharm Research & Development GmbH, Vienna (AT)

( * ) Notice: Subject to any disclaimer, the term of this patent is extended or adjusted under 35 U.S.C. 154(b) by 0 days.

(21) Appl. No.: 13/256,042

(22) PCT Filed: Mar. 10, 2010

(86) PCT No.: PCT/EP2010/053045
§ 371 (c)(1),
(2), (4) Date: Oct. 12, 2011

(87) PCT Pub. No.: WO2010/103046
PCT Pub. Date: Sep. 16, 2010

(65) Prior Publication Data
US 2012/0022154 A1    Jan. 26, 2012

(30) Foreign Application Priority Data
Mar. 13, 2009 (EP) .................... 09155079

(51) Int. Cl.
*A61K 31/215* (2006.01)
*A61K 31/19* (2006.01)
*C07C 331/00* (2006.01)
*C07C 67/02* (2006.01)
*C07C 259/04* (2006.01)

(52) U.S. Cl.
USPC ........... 514/507; 514/510; 514/575; 560/250; 560/315; 562/622

(58) Field of Classification Search
USPC ........... 514/507, 510, 575; 562/622; 560/250, 560/315
See application file for complete search history.

(56) References Cited

PUBLICATIONS

Abe, N. et al., Microbiol. Immunol., vol. 26 (6), 1982, pp. 535-539.
Andersen, F., International Journal of Toxicology, vol. 26, 2007, pp. 79-112.
Asl, M.N. and Hosseinzadeh, H., Phytotherapy Research, vol. 22, 2008, pp. 709-724.
Boyle, W.J. et al., Nature, vol. 423, 2003, pp. 337-342.
Brieskorn, C. et al., Archiv Pharm Ber Dtsch Pharm Ges, vol. 303(11), 1970, pp. 905-912.
Diederich, S. et al., Eur. J. Endocrinol., vol. 142, 2000, pp. 200-207.
Ech-Chahad, A. et al. Tetrahedron Letters, vol. 46, 2005, pp. 5113-5115.
Escher, G. et al., J. Exp. Med., vol. 186, 1997, pp. 189-198.
Isbrucker, R.A. and Burdock, G.A., Regul Toxicol Pharmacol, vol. 46, 2006, pp. 167-192.
Latif, S.A. et al., Mol. Cell Endocrinol., vol. 243, 2005, pp. 43-50.
Nicolaou, K.C. et al., J Am Chem Soc, vol. 124, 2002, pp. 2245-2258.
Odermatt, A. et al., J. Biol. Chem. vol. 274, 1999, pp. 28762-28770.
Petrenko, N.I. et al.: "Synthesis and antiinflammatory and antiulcer properties of glycyrrhetic acid derivatives containing fragments of amino acids or their methyl ethers," Pharmaceutical Chemistry Journal 2000 US, vol. 34, No. 5, 2000, pp. 250-253.
Rios, J. et al., Studies in Natural Product Chemistry, vol. 22, 2000, pp. 93-143.
Schuster, D. et al., J. Med. Chem., vol. 49, 2006, pp. 3454-3466.
Schweizer, R.A. et al., Mol. Cell Endocrinol., vol. 212, 2003, pp. 41-49.
Su, X., et al., Bioorg. & Med. Chem., vol. 12, 2004, pp. 4439-4457.
Su, X., et al., J. Steroid Biochem. Mol. Biol., vol. 104, 2007, pp. 312-320.
Suda, T. et al., Bone, 1995, vol. 17, 2 Suppl., pp. 87S-91S.
Ukil A, et al., J Immunol., vol. 175, 2005, pp. 1161-1169.
Zhang, Y.H. et al., Cell. Immunol., vol. 162, 1995, pp. 97-104.
Zhang, Y.H. et al., Immunology, vol. 79, 1993, pp. 528-534.
Extended European Search Report, European Patent Application No. 09155079.8, Sep. 16, 2009.
International Preliminary Report on Patentability, International Patent Application No. PCT/EP2010/053045, Sep. 13, 2011.
International Search Report, International Patent Application No. PCT/EP2010/053045, May 18, 2010.

*Primary Examiner* — Raymond Henley, III
(74) *Attorney, Agent, or Firm* — Michael Fedrick; Loza & Loza, LLP

(57) ABSTRACT

The present invention encompasses novel triterpene compounds of general formula I, wherein $R^{3a}$, $R^{3b}$, $R^{11a}$, $R^{11b}$, $R^{31}$ and $R^{32}$ are defined as in claim 1, which are suitable for the prevention and/or treatment of diseases mediated by 11 β-HSD and the use thereof for preparing a medicament having the above-mentioned properties.

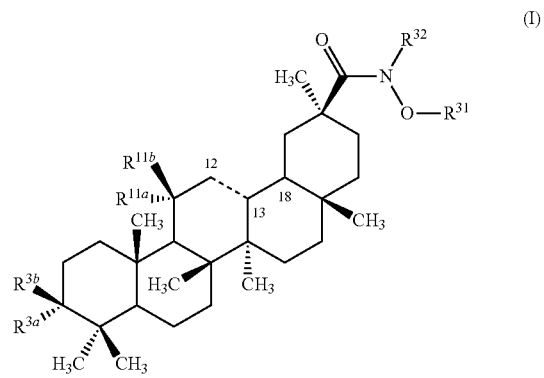

14 Claims, No Drawings

N-HYDROXY C29-AMIDE DERIVATIVES OF OLEANDRANE

CROSS-REFERENCE TO RELATED APPLICATIONS

This application is the U.S. national stage of International Patent Application No. PCT/EP2010/053045, filed on Mar. 10, 2010 and entitled N-HYDROXY C29-AMIDE DERIVATIVES OF OLEANDRANE, which claims the benefit of priority from European Patent Application No. 09155079.8, filed Mar. 13, 2009. The disclosures of the foregoing applications are incorporated herein by reference in their entirety.

FIELD OF THE INVENTION

This invention relates generally to the field of medicinal chemistry. More specifically, it relates to novel triterpene derivatives, preferably glycyrrhetinic acid derivatives that have pharmacologic activities, formulations containing such and their use to diagnose, cure or prevent certain diseases.

BACKGROUND OF THE INVENTION

Licorice root is one of the most ancient medical plants being used in the traditional Chinese, Tibetan, Indian and Arabian medicine. The most important, and well-known bioactive component of licorice root is glycyrrhizin (GL), a natural product of the class of triterpene glycosides, also called saponins. Glycyrrhetinic acid (GA) is the aglycone of GL and thus consists only of the triterpene part without the attached sugar molecules (see FIG. 1). A variety of pharmacological activities for GL and GA have been reported over the last decades comprising in vitro and in vivo studies. A good number of publications can be found in the field of steroid metabolism predominantly describing the inhibitory activity for 11β-HSDs with various pharmacological effects. GA has been widely reported as a potent inhibitor of intercellular gap-junctional communication most likely involving connexin43. Furthermore, anti-inflammatory/immunemodulatory effects were reported suggesting several targets involved in the inflammatory process. Several papers report liver protective and anti-cancer properties whereas the impact on apoptosis/oxidative stress has been discussed controversially. Finally, antibiotic and antiviral effects have been reported comprising antibacterial effects on periodontopathogenic bacteria.

The pharmacology and toxicology of GL and GA has been comprehensively reviewed [1-7].

Figure 1: Structure of Glycyrrhizin (GL) and Glycyrrhetinic acid (GA)

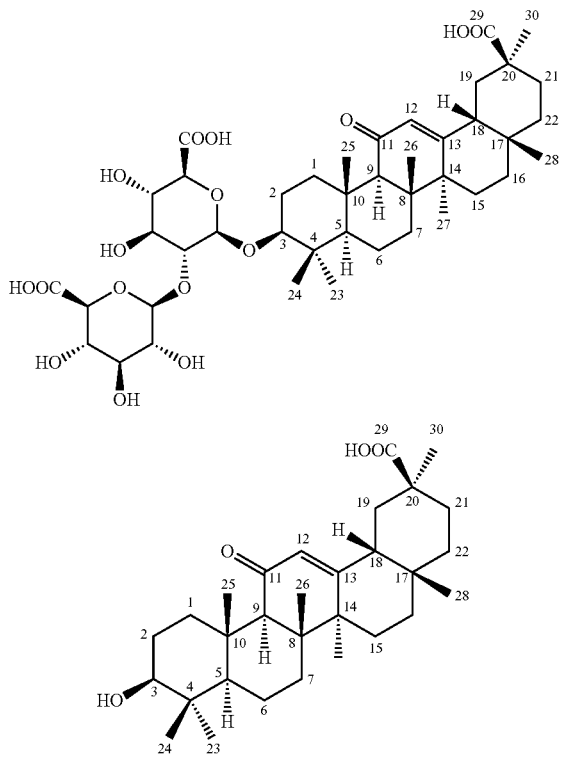

Impact on Apoptosis and Oxidative Stress

GA is a potent inducer of mitochondrial permeability transition and can trigger the pro-apoptotic pathway. GA is a potent inhibitor of bile acid-induced apoptosis and necrosis in a manner consistent with its antioxidative effect, significantly decreases neutrophil-generated oxygen species and inhibits the generation of inflammatory mediators. Below a certain concentration, GA prevents oxidative stress and mitochondrial permeability transition but at higher concentrations GA induces oxidative stress in certain tissues. GA reveals also an effect on the protein expression of markers of oxidative stress (PAI-1 and $p22^{phox}$) and scavenges oxygen free radicals in polymorphonuclear leukocytes (PMN). In addition GL stimulates DNA synthesis, proliferation in hepatocytes, and tyrosine phosphorylation of the EGF receptor and p42 MAP kinase.

Antibiotic and Antiviral Effects

GL, GA and derivatives showed inhibition of replication, growth, proliferation or specific proteins of various viral and bacterial pathogens in vitro and in vivo. Examples include SARS-coronavirus replication, influenza A virus (H1N1, H2N2, H3N2), herpes simplex virus (HSV), hepatitis C virus, hepatitis A, HIV-1-induced cytopathogenicity, hepatitis B virus (HBV), hyaluronate lyase from *Streptococcus agalactiae*, diverse species of periodontopathogenic and capnophilic bacteria, clarithromycin- and metronidazole-resistant strains of *Heliobacter pylori*, plaque formation in Japan encephalitis virus (JEV), vaccinia virus, Epstein-Barr virus (EBV), and *Leishmania donovani*.

In addition GA and GL result in reduced levels of IL-10 and IL-4, but increased levels of IL-12, IFN-gamma, TNF-alpha, and inducible NO synthase.

Liver Protective Effects

GA and GL treatment significantly reduces the increase of serum transaminases induced by D-galactosamine (GalN), CCl4, or retrorsine. GA inhibits the proliferation and collagen production of hepatic stellate cells (HSGs), down-regulates the mRNA expression of type III and I procollagen, and reduces the deposition of type III and I collagen in fibrotic liver. GA also prevents the depletion of glutathione in the livers of CCl4-intoxicated mice and protects gel entrapped hepatocytes from tacrine toxicity.

GA treatment attenuates bile duct and hepatocyte damages in acute vanishing bile duct syndrome (AVBDS) rat model induced by α-naphthylisothiocyanate (ANIT).

Anti-Inflammatory and Immunmodulatory Effects

GA and GL inhibit secretory type IIA phospholipase A2 purified from the synovial fluids of patients with rheumatoid arthritis. GA inhibits the classical complement pathway at the level of C2, complement C3 is a GL-binding protein and GA induces conformational changes in C3. In the presence of GA, two trypsin-resistant fragments of C3α were immunoprecipitated with anti-C3α which could be selectively purified from the synovial fluids of patients with rheumatoid arthritis. In addition, phosphorylation of C3α by CK-2 was completely inhibited by 30 μM GA. GL (100 μM) induces conformational changes in high mobility group box (HMGB)1 and 2 and completely inhibits the phosphorylation of HMGB1/2 by PKC and CK-I.

GA significantly improved bleeding on probing and gingival inflammation in a clinical study evaluating the local application of a paste containing GA.

The anti-inflammatory activity of GA is similar to hydrocortisone on formalin-induced arthritis in albino rats. Repeated treatment with GA significantly inhibits paw edema of rats with adjuvant arthritis (AA) and croton oil-induced mouse-ear-edema, decreases T-lymphocyte ratio, reduces proliferation of synovial cells and pannus formation, and eliminates the destruction of articular cartilage in inflamed joints of AA rat.

GA suppresses TNFα-induced IL-8 production through blockade in the phosphorylation of MAPKs, following IκBα degradation and NFκB activation. GL enhances interleukin-2 (IL-2) secretion and IL-2 receptor (IL-2R) expression. In addition GL promotes tyrosine phosphorylation of p56 induced by anti-CD3. GL augments lipopolysaccharide (LPS)-induced IL-12 p40 mRNA expression, transcription of IL-12 mRNAs and IL-12-protein production. GL increases production of IL-10 in vitro and in mice with Con A-induced hepatitis. GL inhibits prostaglandin E2 production and release of [3H]arachidonic acid. GA lowers inflammatory capillary permeability, inhibits neutrophil emigration and prostaglandin E2 synthesis, and scavenges free radicals in a rat model of histamine, carrageenan, or ararachidonic acid-induced peritonitis. GA dose-dependently increases NO production and iNOS mRNA through activation of protein/DNA binding of NF-κB to its cognate site, enhances the production of nitric oxide from IFN-γ activated cells and tumor cell killing by macrophages activated with IFN-γ. This tumor cell killing is mainly by nitric oxide.

Anti-inflammatory activities of natural triterpenoids including GA have been reviewed recently.

Short Chain Dehydrogenase Reductases (SDR) and Corticoid Metabolism

GA is a potent non-competitive inhibitor of different hydroxysteroid dehydrogenases (HSD). GA inhibits 11β-HSD 1 and 11β-HSD 2 involved in the metabolism of corticosteroids, 3α-HSD involved in inflammatory processes, 3α/β,20β-HSD involved in the metabolism of androgens and progestins, 5β-HSD involved in the metabolism of cortisol, aldosterone and testosterone, and 3β-HSD involved in the metabolism of aldosterone and other steroids.

GL and GA can bind to mineralocorticoid and glucocorticoid receptors with low but sufficient affinity in order to explain the mineralocorticoid-like side effects. GA potentiates the action of aldosterone and facilitates the active transport of sodium in frog skin epithelium. GA stimulates an increase in steroid production in adrenal cells lacking intact cell junctions.

Especially the modification of corticosteroid levels by inhibition of 11β-HSD 1 and 2 by GA has been connected to numerous biological states and diseases. Examples include the reversible, gradual, constant and significant increase in systolic blood pressure, reduction in diuresis and increase in renal sodium retention, the reduction of thigh circumference and thickness of the subcutaneous fat layer in human volunteers after topical application, the reduction of metabolic detoxification of the cigarette smoke carcinogen nitrosamine 4-methylnitrosamino-1-(3-pyridyl)-1-butanone (NNK), the involution of the thymus and thymocyte apoptosis, the potentiation of corticosteroid effects in cultured primary human bronchial epithelial cells (PBECs), ear swelling in dinitrofluorobenzene challenged mice, human volunteer skin vasoconstrictor assay and lung tissue, the retardation of the development of autoimmune disease, as well as the increased glucose use in subregions of the hypothalamus, hippocampus, neocortex and subthalamus.

11β-HSD mRNA is expressed in neurones of the hypothalamic paraventricular nucleus (PVN) where corticotrophin-releasing factor-41 (CRF-41) is synthesized and GA decreases the release of CRF-41 into hypophysial portal blood in rats, suggesting that 11β-HSD regulates the effective corticosterone feedback signal to CRF-41 neurons.

Anticancer Effects

GA inhibits oxidative stress DMBA/TPA-induced skin tumor formation, inhibits ear edema and ornithine decarboxylase activity induced by croton oil in mice, protects against rapid DNA damage and decreases unscheduled DNA synthesis induced by benzo[a]pyrene, increases the antiproliferative effect of glucocorticoids In MCF-7 and ZR-75-1 breast cancer cells, reduces the tumor weight in rats transplanted with 'Oberling-Guerin' myeloma, inhibits proliferation of HepG2 human hepatoma cell line, inhibits the mutagenicity of benzo[a]pyrene, 2-aminofluorene and aflatoxin B1, and protects against tumor initiation as well as tumor promotion by 7,12-dimethylbenz[a]anthracene (DMBA) and 12-O-tetradecanoylphorbol-13-acetate.

GA also increases the accumulation of calcein, a fluorescent substrate of multidrug resistance protein 1 (MRP1) and of daunorubicin, a fluorescent substrate of P-glycoprotein, resulting in sensitivity to anticancer drugs, showing that GA reverses multidrug resistance.

Gap Junction Blockade and Endothelial Relaxation

GA inhibits intercellular gap-junctional communication in human fibroblasts and cultured rat neonatal cardiomyocytes, as well as type 1 or type 2A protein phosphatase-mediated Connexin43 dephosphorylation in WB-F344 rat liver epithelial cells. GA inhibites fluorescence replacement after photobleaching (FRAP) in primary chick osteocyte cultures, also indicating gap junction blockade.

GA increases the apparent cell input resistance and completely blocks membrane chloride conductance blocked while $Na^+$ and $K^+$ conductance are virtually unchanged.

GA in a concentration-dependent fashion attenuates EDHF-type relaxations to acetylcholine (ACh), observed in the presence of NG-nitro-L-arginine methyl ester (L-NAME)

and indomethacin, modulates contractions produced by noradrenalin or high-K solutions and significantly reduces ACh-induced hyperpolarizations in both, endothelial and smooth muscle cells of guinea pig coronary and rat mesenteric arteries. Inhibition of the EDHF-hyperpolarization and relaxation in the smooth muscle may stem from the inhibition of endothelial cell hyperpolarization. GA quickly blocked electrical communication between smooth muscle and endothelial cells in guinea-pig mesenteric arterioles.

GA inhibits pressure-induced myogenic tone of rat middle cerebral arteries and vasopressin-induced vasoconstriction, increases input resistance in rat isolated mesenteric small arteries, desynchronised isolated smooth muscle cells, and had nonjunctional effects on membrane currents. GA significantly increases the frequency of phrenic bursts decreases the peak amplitude of integrated phrenic nerve discharge in an arterially perfused rat preparation.

GA inhibits the spike component of the action potential (AP), reduces contraction evoked by electrical stimulation, inhibits slow depolarization with superimposed APs and phasic contractions of the ureter induced by neurokinin A, and inhibits the KCl-evoked APs and phasic contractions without affecting the sustained responses in the guinea pig ureter.

GA inhibits frequencies of paced contractions, likely owing to inhibition of l-type $Ca^{2+}$ channels, reduces the amplitudes of spontaneous and nerve-induced contractions, decreases phasic contractions and depolarizes resting membrane potential in murine small intestinal muscles. GA also inhibits the spread of Lucifer yellow, increases input resistance, decreases cell capacitance in interstitial cells of Cajal networks and decreased L-type $Ca^{2+}$ current without affecting the voltage dependence of this current.

GA decreased the postsynaptic light response in murine retinal ganglion cells to 30% of control.

Other Effects

GA reduces the bon resorption in rheumatoid arthritis and periodontits.

GA reduces coughing in guinea-pigs by 50% compared to saline.

GA increases cytoplasmic free $Ca^{2+}$ and inhibits $Ca^{2+}$ increases induced by antigen, ATP, phenyephrine and thrombin. GA inhibits dexamethasone-induced increases in the histamine synthesis and histamine release. GA inhibits histidine decarboxylase and maturation of mast cells, lowers expression of PKC delta mRNA suggesting that the inhibition of histamine synthesis by GA is regulated by nPKC delta. GA significantly inhibits the degranulation of RBL-2H3 cells induced by IgE with the antigen (DNP-HSA) and rat peritoneal mast cells induced by compound 48/80. GA inhibits the passive cutaneous anaphylactic reaction as well as the scratching behaviour in mice induced by compound 48/80 and the production of IgE in ovalbumin-induced asthma mice.

GA sodium salt strongly counteracts arrhythmia induced by chloroform, lengthens the appearance time of arrhythmia induced by $CaCl_2$, slightly retards the heart rate of rats and rabbits, and partly antagonizes the acceleration effect of isoproterenol on rabbit hearts.

GA competitively inhibits the $Na^+/K^+$-ATPase of canine kidney basolateral membranes.

GA significantly increases insulin-stimulated glucose uptake in 3T3-L1 adipocytes, glucose-stimulated insulin secretion in islets isolated from mice and induces mRNA levels of insulin receptor substrate-2, pancreas duodenum homeobox-1 and glucokinase in islets.

SUMMARY OF THE INVENTION

New triterpene derivatives, preferably glycyrrhetinic acid derivatives have been prepared and show desirable biological and pharmacologic activities relevant for the diagnosis, prevention and therapy of certain diseases.

Accordingly, one aspect of the present invention includes compounds having the following general structural formula I:

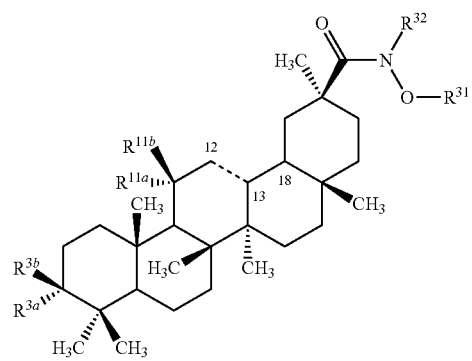

wherein $R^{3a}$ and $R^{3b}$ together are selected from =O, =$NR^a$, =N—O—$R^a$; or $R^{3a}$ and $R^{3b}$ are independently from one another selected from hydrogen, —O—$R^a$, —O—C(=O)—$R^a$, —NH—$R^a$, —NH—O—$R^a$, —NH—C(=O)—$R^a$ and —NH—S(=O)$_2R^a$; and $R^{11a}$ and $R^{11b}$ together are selected from =O, =$NR^a$, =N—O—$R^a$; or $R^{11a}$ and $R^{11b}$ are independently from one another selected from hydrogen, —O—$R^a$, —O—C(=O)—$R^a$, —NH—$R^a$, methyl, ethyl, ethynyl, fluorine, chlorine, and bromine; and a single or double bond is present at 12-13;

$R^{31}$ is selected from hydrogen, hydroxyalkyl, $C_{1-6}$alkyl, $C_{2-6}$alkenyl, $C_{2-8}$alkynyl, —$CF_3$, —$(CH_2)_n$—$C_{6-14}$aryl, —CH=CH—$C_{6-14}$aryl, —C≡C—$C_{6-14}$aryl, —$(CH_2)_n$—$C_{5-14}$heteroaryl, —CH=CH—$C_{5-14}$heteroaryl, —C≡C—$C_{5-14}$heteroaryl, carboxylic acid, —$(CH_2)_n$—$C_{3-8}$cycloalkyl, —CH=CH—$C_{3-8}$cycloalkyl and —C≡C—$C_{3-8}$cycloalkyl; and $R^{32}$ is hydrogen or selected from optionally substituted hydroxyalkyl, $C_{1-6}$alkyl, $C_{2-6}$alkenyl, $C_{2-8}$alkynyl, —$CF_3$, —$(CH_2)_n$—$C_{6-14}$aryl, —CH=CH—$C_{6-14}$aryl, —C≡C—$C_{6-14}$aryl, —$(CH_2)_n$—$C_{5-14}$heteroaryl, —CH=CH—$C_{5-14}$heteroaryl, —C≡C—$C_{5-14}$heteroaryl, carboxylic acid, —$(CH_2)_n$—$C_{3-8}$cycloalkyl, —CH=CH—$C_{3-8}$cycloalkyl and —C≡C—$C_{3-8}$cycloalkyl;

$R^a$ is selected from hydrogen, hydroxyalkyl, $C_{1-6}$alkyl, $C_{2-6}$alkenyl, $C_{2-8}$alkynyl, —$CF_3$, —$(CH_2)_n$—$C_{6-14}$aryl, —CH=CH—$C_{6-14}$aryl, —C≡C—$C_{6-14}$aryl, —$(CH_2)_n$—$C_{5-14}$heteroaryl, —CH=CH—$C_{5-14}$heteroaryl, —C≡C—$C_{5-14}$heteroaryl, carboxylic acid, —$(CH_2)_n$—$C_{3-8}$cycloalkyl, —CH=CH—$C_{3-8}$cycloalkyl and —C≡C—$C_{3-8}$cycloalkyl; and each n independently of one another denotes 0, 1 or 2; and optionally in the form of the pharmaceutically effective salts, solvates, prodrugs, tautomers, racemates, enantiomers, diastereomers or the mixtures thereof, with the proviso that compounds (3S,18R,20S)-3-(acetyloxy)-N-hydroxy-11-oxo-olean-12-en-29-amide and (3S,18R,20S)-3-(hydroxy)-N-hydroxy-11-oxo-olean-12-en-29-amide are not encompassed.

In a further aspect, the present invention includes compounds of general formula I, wherein
$R^{11a}$ and $R^{11b}$ together denotes =O; and
a double bond is present at 12-13.

A further aspect of the invention are compounds of general formula I, wherein
$R^{31}$ is selected hydrogen, $C_{1-6}$alkyl, $C_{2-6}$alkenyl, $C_{2-8}$alkynyl, —$CF_3$, —$(CH_2)_n$—$C_{6-14}$aryl, —$(CH_2)_n$—$C_{5-14}$heteroaryl and —$(CH_2)_n$—$C_{3-8}$cycloalkyl.

A further aspect of the invention are compounds of general formula I, wherein
$R^{32}$ is selected from hydrogen and optionally substituted hydroxyalkyl, $C_{1-6}$alkyl, $C_{2-6}$alkenyl, $C_{2-8}$alkynyl, —$CF_3$, —$(CH_2)_n$—$C_{6-14}$aryl, —$(CH_2)_n$—$C_{5-14}$heteroaryl and —$(CH_2)_n$—$C_{3-8}$cycloalkyl.

In a further aspect, the present invention includes compounds of general formula I, wherein
$R^{32}$ is selected from hydrogen, methyl, ethyl, n-propyl, i-propyl, allyl, ethynyl, 2-hydroxyethyl, 3-hydroxypropyl, cyclopropyl and cyclobutyl.

A further aspect of the invention are compounds of general formula I, wherein
$R^{3a}$ is hydrogen and
$R^{3b}$ is selected from —O—$R^a$, —O—C(=O)—$R^a$, —NH—$R^a$, —NH—O—$R^a$, —NH—C(=O)—$R^a$ and —NH—S(=O)$_2R^a$.

A further aspect of the invention are compounds of general formula I, wherein
$R^{3b}$ is selected from —OH, —O-acetyl, —O-succinyl, —$NH_2$, —NH-acetyl, —NH-succinyl, —NH—$S(O)_2CF_3$, —NH—$S(O)_2CH_3$ and —NH—$S(O)_2CH_2CH_2COOH$.

A further aspect of the invention are compounds of general formula I, wherein
$R^{3b}$ is hydrogen
$R^{3a}$ is selected from O—$R^a$, —O—C(=O)—$R^a$, —NH—$R^a$, —NH—O—$R^a$, —NH—C(=O)—$R^a$ and —NH—S(=O)$_2R^a$.

A further aspect of the invention are compounds of general formula I, wherein
$R^{3a}$ is selected from —OH, —O-acetyl, —O-succinyl, —$NH_2$, —NH-acetyl, —NH-succinyl, —NH—$S(O)_2CF_3$, —NH—$S(O)_2CH_3$ and —NH—$S(O)_2CH_2CH_2COOH$.

A further aspect of the invention are compounds of general formula I, wherein
$R^{3a}$ and $R^{3b}$ together are selected from oxo, imino and =N—O—$R^a$.

In a further aspect, the present invention includes compounds of general formula I, wherein
$R^{3a}$ and $R^{3b}$ together are =N—O—$R^a$ and $R^a$ is hydrogen or methyl.

A further aspect of the invention are compounds of general formula I, selected from the group consisting of
(3S,18R,20S)-3-(Acetyloxy)-N-hydroxy-N-methyl-11-oxo-olean-12-en-29-amide
(3S,18R,20S)-3-Hydroxy-N-methoxy-11-oxo-olean-12-en-29-amide
(3S,18R,20S)-3-(Acetyloxy)-N-methoxy-11-oxo-olean-12-en-29-amide
(3S,18R,20S)-3-(Acetyloxy)-N-methyl-N-methoxy-11-oxo-olean-12-en-29-amide
(3S,18R,20S)-3-Hydroxy-N-methyl-N-methoxy-11-oxo-olean-12-en-29-amide
(3S,18R,20S)-3-Hydroxy-N-(2-propen-1-yloxy)-11-oxo-olean-12-en-29-amide
(3S,18R,20S)-3-(Acetyloxy)-N-(2-propen-1-yloxy)-11-oxo-olean-12-en-29-amide
(3S,18R,20S)-3-Hydroxy-N-(1,1-dimethylethoxy)-11-oxo-olean-12-en-29-amide
(3S,18R,20S)-3-(Acetyloxy)-N-(1,1-dimethylethoxy)-11-oxo-olean-12-en-29-amide
(3S,18R,20S)-3-Hydroxy-N-(phenylmethoxy)-11-oxo-olean-12-en-29-amide
(3S,18R,20S)-3-(Acetyloxy)-N-(phenylmethoxy)-11-oxo-olean-12-en-29-amide
(3S,18R,20S)-3-Hydroxy-N-phenoxy-11-oxo-olean-12-en-29-amide
(3S,18R,20S)-3-(Acetyloxy)-N-phenoxy-11-oxo-olean-12-en-29-amide and
(3S,18R,20S)-3-(Acetamino)-N-benzyloxy-11-oxo-olean-12-en-29-amide
(3S,18R,20S)-3-(Acetamino)-N-hydroxy-11-oxo-olean-12-en-29-amide
(3R,18R,20S)-3-(Acetamino)-N-benzyloxy-11-oxo-olean-12-en-29-amide
(3R,18R,20S)-3-(Acetamino)-N-hydroxy-11-oxo-olean-12-en-29-amide
(18R,20S)-3-imino-N-Hydroxy-11-oxo-olean-12-en-29-amide.
(18R,20S)-N-Hydroxy-3,11-dioxo-olean-12-en-29-amide.

In a further aspect, the present invention includes compounds of general formula I or the pharmacologically effective salts thereof, as medicaments.

In a further aspect, the present invention includes a pharmaceutical preparation, containing as active substance one or more compounds of general formula I or the pharmacologically effective salts thereof, optionally in combination with conventional excipients and/or carriers.

In a further aspect, the present invention includes the use of compounds of general formula I for preparing a medicament for the treatment and/or prevention of chronic inflammatory diseases, autoimmune diseases, skin diseases, bone diseases, metabolic diseases, infectious diseases and cancer.

In a further aspect, the present invention includes a use of a compound or a combination of compounds of the invention as a medicament or as a diagnostic.

In a further aspect, the present invention includes use of a compound or a combination of compounds of the invention to treat a condition or disease that benefits from the inhibition of 11β-HSD isozymes. In particular embodiments the condition or disease that benefit from 11β-HSD inhibition are chronic inflammatory diseases.

Accordingly, also included within the scope of the present invention is a method of treating chronic inflammatory diseases, comprising administering an effective amount of a compound of the invention to a subject in need thereof. Further the invention includes a use of a compound of the invention to treat chronic inflammatory diseases, as well as a use of a compound of the invention to prepare a medicament to treat chronic inflammatory diseases.

In a further aspect, the present invention includes a method of treating autoimmune diseases, comprising administering an effective amount of a compound of the invention to a subject in need thereof. Further the invention includes a use of a compound of the invention to treat autoimmune diseases, as well as a use of a compound of the invention to prepare a medicament to treat autoimmune diseases.

Also included within the scope of the present invention is a method of treating skin diseases, comprising administering an effective amount of a compound of the invention to a subject in need thereof. Further the invention includes a use of a compound of the invention to treat skin diseases, as well as a use of a compound of the invention to prepare a medicament to treat skin diseases.

The present invention also includes a method of treating metabolic diseases, comprising administering an effective amount of a compound of the invention to a subject in need thereof. The invention also includes a use of an 11β-HSD inhibiting compound of the invention to treat metabolic diseases, as well as a use of an 11β-HSD inhibiting compound of the invention to prepare a medicament to treat and metabolic diseases.

An additional aspect of the present invention is a method of treating infectious diseases comprising administering an effective amount of a compound of the invention to a subject in need thereof. Also included in the present invention is a use of a compound of the invention to treat infectious diseases as well as a use of a compound of the invention to prepare a medicament to treat infectious diseases.

A further aspect of the present invention is a method of treating cancer comprising administering an effective amount of a compound of the invention to a subject in need thereof. Also included in the present invention is a use of a compound of the invention to treat cancer as well as a use of a compound of the invention to prepare a medicament to treat cancer.

Other features and advantages of the present invention will become apparent from the detailed description. It should be understood, however, that the detailed description and the specific examples while indicating preferred embodiments of the invention are given by way of illustration only, since various changes and modifications within the spirit and scope of the invention will become apparent to those skilled in the art from this detailed description.

DETAILED DESCRIPTION OF THE INVENTION

The compounds of the invention include compounds of formula I as hereinbefore defined, including all polymorphs and crystal habits thereof, salts, prodrugs and isomers thereof (including optical, geometric and tautomeric isomers) as hereinafter defined and isotopically-labeled compounds of formula I.

Unless specified otherwise, the term alkyl, when used alone or in combination with other groups or atoms, refers to a saturated straight or branched chain consisting solely of 1 to 6 hydrogen-substituted carbon atoms, and includes methyl, ethyl, propyl, isopropyl, n-butyl, 1-methylpropyl, isobutyl, t-butyl, 2,2-dimethylbutyl, n-pentyl, 2-methylpentyl, 3-methylpentyl, 4-methylpentyl, n-hexyl and the like.

Unless specified otherwise, the term alkenyl refers to a partially unsaturated straight or branched chain consisting solely of 2 to 6 hydrogen-substituted carbon atoms that contains at least one double bond, and includes vinyl, allyl, 2-methylprop-1-enyl, but-1-enyl, but-2-enyl, but-3-enyl, buta-1,3-dienyl, penta-1,3-dienyl, penta-2,4-dienyl, 2-methylbut-1-enyl, 2-methylpent-1-enyl, 4-methylpent-1-enyl, 4-methylpent-2-enyl, 2-methylpent-2-enyl, 4-methylpenta-1,3-dienyl, hexen-1-yl and the like.

Unless specified otherwise, the term alkynyl refers to a partially unsaturated straight or branched chain consisting solely of 2 to 8 hydrogen-substituted carbon atoms that contains at least one triple bond, and includes ethynyl, 1-propynyl, 2-propynyl, 2-methylprop-1-ynyl, 1-butynyl, 2-butynyl, 3-butynyl, 1,3-butadiynyl, 3-methylbut-1-ynyl, 4-methylbut-ynyl, 4-methylbut-2-ynyl, 2-methylbut-1-ynyl, 1-pentynyl, 2-pentynyl, 3-pentynyl, 4-pentynyl, 1,3-pentadiynyl, 1,4-pentadiynyl, 3-methylpent-1-ynyl, 4-methylpent-2-ynyl, 4-methylpent-2-ynyl, 1-hexynyl, and the like.

Unless specified otherwise, the term hydroxyalkyl refers to an aliphatic alkyl-, alkenyl-, or alkynyl-groups substituted with one or more hydroxyl groups, and includes 2-hydroxyethyl, 2-hydroxypropyl, 3-hydroxypropyl, 2-hydroxybutyl, 3-hydroxybutyl, 4-hydroxybutyl, 2-hydroxy-1-methyl-ethyl, 2-hydroxy-1-ethyl-ethyl, 2,3-bihydroxypropyl, 2,3,4-trihydroxybutyl, 2-hydroxy-1-hydroxymethyl-ethyl, 3-hydroxy-2-hydroxymethyl-propyl, 3-hydroxy-1-(2-hydroxyethyl)-propyl, and the like.

Unless specified otherwise, the term carboxylic acid refers to an aliphatic mono- or dicarboxylic acid group containing from 2 to 18 carbon atoms that may optionally be substituted with one or more, identical or different substituents, independently selected from $C_{1-4}$alkyl, fluoro-substituted $C_{1-4}$alkyl, halo, $OC_{1-4}$alkyl, fluoro-substituted $OC_{1-4}$alkyl, aryl, heteroaryl, $NH_2$, NH(alkyl), N(alkyl)$_2$, $CO_2H$, $CO_2$(alkyl), $NO_2$ and CN. Examples of carboxylic acids include formic acid, acetic acid, propionic acid, butyric acid, valeric acid, caproic acid, enanthic acid, caprylic acid, acrylic acid, pyruvic acid, acetoacetic acid, oxalic acid, malonic acid, malic acid, fumaric acid, succinic acid, glutaric acid, adipic acid, lactic acid, and the like.

Unless specified otherwise, the term cycloalkyl, when used alone or in combination with other groups or atoms, refers to a saturated or unsaturated ring consisting solely of 3 to 8 carbon atoms, that may optionally be substituted with one or more, identical or different substituents, suitably one to three substituents, independently selected from $C_{1-4}$alkyl, fluoro-substituted $C_{1-4}$alkyl, halo, $OC_{1-4}$alkyl, fluoro-substituted $OC_{1-4}$alkyl, $NH_2$, NH(alkyl), N(alkyl)$_2$, $CO_2H$, $CO_2$(alkyl), $NO_2$ and CN. Examples of cycloalkyl groups include cyclopropyl, cyclobutyl, cyclopentyl, cyclohexyl, cycloheptyl, cyclooctyl, cyclopropenyl, cyclobutenyl, cyclopentenyl, cyclohexenyl, cycloheptenyl, cyclooctenyl and the like.

Unless specified otherwise, the term aryl refers to an aromatic mono- or bicyclic group containing from 6 to 14 carbon atoms that may be optionally fused with a fully or partially saturated or unsaturated carbocyclic ring and may optionally be substituted with one or more, identical or different substituents, suitably one to three substituents, independently selected from $C_{1-4}$alkyl, fluoro-substituted $C_{1-4}$alkyl, halo, $OC_{1-4}$alkyl, fluoro-substituted $OC_{1-4}$alkyl, $NH_2$, NH(alkyl), N(alkyl)$_2$, $CO_2H$, $CO_2$(alkyl), $NO_2$ and CN. Examples of aryl groups include phenyl, naphthyl, indanyl, and the like.

Unless specified otherwise, the term heteroaryl refers to an aromatic mono- or bicyclic group containing from 5 to 14 carbon atoms, of which one to five is replaced with a heteroatom selected from N, S and O, that may optionally be reduced to a non-aromatic heterocycle and may optionally be substituted with one or more, identical or different substituents, suitably one to three substituents, independently selected from $C_{1-4}$alkyl, fluoro-substituted $C_{1-4}$alkyl, halo, $OC_{1-4}$alkyl, fluoro-substituted $OC_{1-4}$alkyl, $NH_2$, NH(alkyl), N(alkyl)$_2$, $CO_2H$, $CO_2$(alkyl), $NO_2$ and CN. Examples of heteroaryl groups include pyrrolyl, dihydropyrrolyl, pyrrolidinyl, indolyl, isoindolyl, indolizinyl, imidazolyl, pyrazolyl, benzimidazolyl, imidazo(1,2-a)pyridinyl, indazolyl, purinyl, pyrrolo(2,3-c)pyridinyl, pyrrolo(3,2-c)pyridinyl, pyrrolo(2,3-b)pyridinyl, pyrazolo(1,5-a)pyridinyl, 1,2,3-triazolyl, 1,2,4-triazolyl, tetrazolyl, oxazolyl, isoxazolyl, 1,3,4-oxadiazolyl, 1,2,5-oxadiazolyl, 1,2,4-oxadiazolyl, 1,2,3-oxadiazolyl, thiazolyl, isothiazolyl, 1,3,4-thiadiazolyl, 1,2,5-thiadiazolyl, 1,2,4-thiadiazolyl, 1,2,3-thiadiazolyl, furanyl, dihydrofuranyl, tetrahydrofuranyl, benzofuranyl, isobenzofuranyl, thiophenyl, dihydrothiophenyl, tetrahydrothiophenyl, benzothiophenyl, benzoisothiophenyl, pyridyl, piperidinyl, quinolinyl, isoquinolinyl, quinolizinyl, pyrazinyl, pyridazinyl, pyrimidinyl, pyranyl, tetrahydropyranyl, 1,2,3-triazinyl, 1,2,4-triazinyl, 1,3,5-triazinyl, chromenyl, morpholinyl, diazepinyl, benzodiazepinyl, and the like.

Unless specified otherwise, the term fluoro-substituted as used herein means that, in the group being described, one or more, including all, of the hydrogen atoms has been replaced by F. For example, a fluoro-substituted alkyl includes trifluoromethyl, trifluoroethyl, pentafluoroethyl and the like.

Unless specified otherwise, as used herein, the terms halogen and halo include F, Cl, Br, and I. Under standard nomenclature rules used throughout this disclosure, the point of attachment of the designated side chain is described first followed by the adjacent functionality toward the terminal portion. A substituent's point of attachment may also be indicated by a dashed line to indicate the point(s) of attachment, followed by the adjacent functionality and ending with the terminal functionality.

It is intended that the definition of any substituent or variable at a particular location in a molecule be independent of its definitions elsewhere in that molecule. It is understood that substituents and substitution patterns on the compounds of this invention can be selected by one of ordinary skill in the art to provide compounds that are chemically stable and that can be readily synthesized by techniques known in the art as well as those methods set forth herein.

The term pharmaceutically acceptable means compatible with the treatment of animals, in particular, humans. The term pharmaceutically acceptable salt includes both pharmaceutically acceptable acid addition salts and pharmaceutically acceptable basic addition salts.

The term pharmaceutically acceptable acid addition salt as used herein means any non-toxic organic or inorganic salt of any base compound of the disclosure, or any of its intermediates. Basic compounds of the disclosure that may form an acid addition salt include, for example, compounds that contain a basic nitrogen atom. Illustrative inorganic acids which form suitable salts include hydrochloric, hydrobromic, sulfuric and phosphoric acids, as well as metal salts such as sodium monohydrogen orthophosphate and potassium hydrogen sulfate. Illustrative organic acids that form suitable salts include mono-, di-, and tricarboxylic acids such as glycolic, lactic, pyruvic, malonic, succinic, glutaric, fumaric, malic, tartaric, citric, ascorbic, maleic, benzoic, phenylacetic, cinnamic and salicylic acids, as well as sulfonic acids such as p-toluene sulfonic and methanesulfonic acids. Either the mono-, di- or the tri-acid salts can be formed, and such salts may exist in either a hydrated, solvated or substantially anhydrous form. In general, the acid addition salts of the compounds of the disclosure are more soluble in water and various hydrophilic organic solvents, and generally demonstrate higher melting points in comparison to their free base forms. The selection of the appropriate salt will be known to one skilled in the art. Other non-pharmaceutically acceptable acid addition salts, e.g. oxalates, may be used, for example, in the isolation of the compounds of the disclosure, for laboratory use, or for subsequent conversion to a pharmaceutically acceptable acid addition salt.

The term pharmaceutically acceptable basic salt as used herein means any non-toxic organic or inorganic basic addition salt of any acid compound of the invention, or any of its intermediates, which are suitable for or compatible with the treatment of animals, in particular humans. Acidic compounds of the invention that may form a basic addition salt include, for example compounds that contain carboxylic acid, sulfonic acid, sulfinic acid, sulfonamide, N-unsubstituted tetrazole, phosphoric acid ester, or sulfuric acid ester. Illustrative inorganic bases which form suitable salts include lithium, sodium, potassium, calcium, magnesium, or barium hydroxide. Illustrative organic bases which form suitable salts include aliphatic, alicyclic or aromatic organic amines such as methylamine, trimethylamine and picoline or ammonia. The selection of the appropriate salt will be known to a person skilled in the art. Other non-pharmaceutically acceptable basic addition salts, may be used, for example, in the isolation of the compounds of the invention, for laboratory use, or for subsequent conversion to a pharmaceutically acceptable acid addition salt. The formation of a desired compound salt is achieved using standard techniques. For example, the neutral compound is treated with a base in a suitable solvent and the formed salt is isolated by filtration, extraction or any other suitable method.

The term subject or patient or synonym thereto, as used herein includes all members of the animal kingdom, especially mammals, including human. The subject or patient is suitably a human.

As used herein, and as well understood in the art, treatment is an approach for obtaining beneficial or desired results, including clinical results. Beneficial or desired clinical results can include, but are not limited to, alleviation or amelioration of one or more symptoms or conditions, diminishment of extent of disease, stabilized (i.e. not worsening) state of disease, preventing spread of disease, delay or slowing of disease progression, amelioration or palliation of the disease state, and remission (whether partial or total), whether detectable or undetectable. Treatment can also mean prolonging survival as compared to expected survival if not receiving treatment.

Palliating a disease or disorder means that the extent and/or undesirable clinical manifestations of a disorder or a disease state are lessened and/or time course of the progression is slowed or lengthened, as compared to not treating the disorder. The term prevention or prophylaxis, or synonym thereto, as used herein refers to a reduction in the risk or probability of a patient becoming afflicted with the disease or manifesting a symptom associated with the disease.

The term therapeutically effective amount, effective amount or sufficient amount of a compound of the present invention is a quantity sufficient to, when administered to the subject, including a mammal, for example a human, effect beneficial or desired results, including clinical results, and, as such, an effective amount or synonym thereof depends upon the context in which it is being applied. For example, in the context of 11β-HSD inhibition, it is an amount of the compound sufficient to achieve an inhibition of 11β-HSD activity compared to the response obtained without administration of the compound. In the context of disease, therapeutically effective amounts of the compounds of the present invention are used to treat, modulate, attenuate, reverse, or affect a disease or conditions that benefits from an inhibition of 11β-HSD, for example, chronic inflammatory diseases. An effective amount is intended to mean that amount of a compound that is sufficient to treat, prevent or inhibit such diseases or conditions. The amount of a given compound of the present invention that will correspond to such an amount will vary depending upon various factors, such as the given drug or compound, the pharmaceutical formulation, the route of administration, the type of disease or disorder, the identity of the subject or host being treated, and the like, but can nevertheless be routinely determined by one skilled in the art. Also, as used herein, a therapeutically effective amount of a compound of the present invention is an amount which prevents, inhibits, suppresses or reduces a disease or conditions that benefits from an inhibition of 11β-HSD, for example, chronic inflammatory diseases as determined by clinical symptoms in a subject as compared to a control. As defined herein, a therapeutically effective amount of a compound of the present invention may be readily determined by one of ordinary skill by routine methods known in the art.

In an embodiment, a therapeutically effective amount of a compound of the present invention ranges from about 0.01 to about 100 mg/kg body weight, suitably about 0.02 to about 50 mg/kg body weight, and more suitably, from about 0.05 to about 20 mg/kg body weight. The skilled artisan will appreciate that certain factors may influence the dosage required to effectively treat a subject, or prevent a subject, suffering from a disease or conditions that benefits from an inhibition of 11β-HSD activity, for example chronic inflammatory diseases, and these factors include, but are not limited to, the severity of the disease or disorder, previous treatments, the general health and/or age of the subject and other diseases present.

Moreover, a treatment or prevention regime of a subject with a therapeutically effective amount of the compound of the present invention may consist of a single administration, or alternatively comprise a series of applications. For example, the compound of the present invention may be administered at least once a week. However, in another embodiment, the compound may be administered to the subject from about one time per week to about three times daily for a given treatment. The length of the treatment period depends on a variety of factors, such as the severity of the disease, the age of the patient, the concentration and the activity of the compounds of the present invention, or a combination thereof. It will also be appreciated that the effective dosage of the compound used for the treatment or prophylaxis may increase or decrease over the course of a particular treatment or prophylaxis regime. Changes in dosage may result and become apparent by standard diagnostic assays known in the art. In some instances, chronic administration may be required.

As used herein the term administered contemporaneously means that two substances are administered to a subject in such a way that they are both biologically active in the subject at the same time. The exact details of the administration will depend on the pharmacokinetics of the two substances in the presence of each other, and can include administering one substance within 24 hours of administration of the other, if the pharmacokinetics is suitable. Designs of suitable dosing regimens are routine for one skilled in the art. In particular embodiments, two substances will be administered substantially simultaneously, i.e. within minutes of each other, or in a single composition that comprises both substances.

To inhibit or suppress or reduce or downregulate a function or activity, such 11β-HSD activity, is to reduce the function or activity when compared to otherwise same conditions except for a condition or parameter of interest, or alternatively, as compared to another conditions.

In understanding the scope of the present disclosure, the term comprising and its derivatives, as used herein, are intended to be open ended terms that specify the presence of the stated features, elements, components, groups, integers, and/or steps, but do not exclude the presence of other unstated features, elements, components, groups, integers and/or steps. The foregoing also applies to words having similar meanings such as the terms, including, having and their derivatives. Finally, terms of degree such as substantially, about and approximately as used herein mean a reasonable amount of deviation of the modified term such that the end result is not significantly changed. These terms of degree should be construed as including a deviation of at least ±5% of the modified term if this deviation would not negate the meaning of the word it modifies.

Unless otherwise indicated, the terms a, an, and the as used herein mean one or more that one.

Compounds of the Invention

A new class of compounds derived from glycyrrhetinic acid has been identified as drugs for the treatment of chronic inflammatory diseases, autoimmune diseases, skin diseases, bone diseases, metabolic diseases, infectious diseases and cancer. The compounds according to the invention may be readily prepared by a person skilled in the art on the basis of his general knowledge. Results show, that glycyrrhetinic acid derivatives, namely compound 1, inhibit both, 11β-HSDs enzyme activity and TNFα expression. Accordingly, compound 1 and related compounds are a novel class of mechanism-based drugs against chronic inflammatory diseases, autoimmune diseases, skin diseases, bone diseases, metabolic diseases, infectious diseases and cancer that act as inhibitors of 11β-HSDs enzyme activity and TNFα expression.

Accordingly, in one its aspects, the present invention includes a compound selected from a compound of formula I:

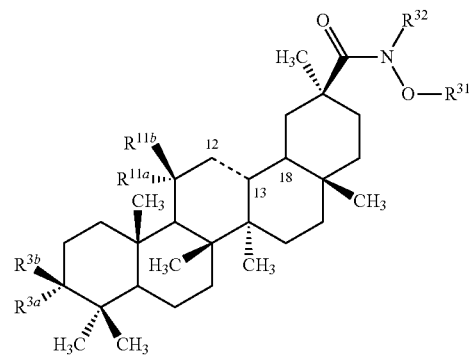

wherein $R^{3a}$, $R^{3b}$, $R^{11a}$, $R^{11b}$, $R^{31}$ and $R^{31}$ have the meanings as defined herein.

The compounds of the invention may exist in a continuum of solid states ranging from fully amorphous to fully crystalline. The term amorphous refers to a state in which the material lacks long range order at the molecular level and, depending upon temperature, may exhibit the physical properties of a solid or a liquid. Typically such materials do not give distinctive X-ray diffraction patterns and, while exhibiting the properties of a solid, are more formally described as a liquid. Upon heating, a change from solid to liquid properties occurs which is characterized by a change of state, typically second order (glass transition). The term crystalline refers to a solid phase in which the material has a regular ordered internal structure at the molecular level and gives a distinctive X-ray diffraction pattern with defined peaks. Such materials when heated sufficiently will also exhibit the properties of a liquid, but the change from solid to liquid is characterized by a phase change, typically first order (melting point).

The compounds of the invention may also exist in unsolvated and solvated forms. The term solvate is used herein to describe a molecular complex comprising the compound of the invention and one or more pharmaceutically acceptable solvent molecules, for example, ethanol. The term hydrate is employed when said solvent is water. When the solvent or water is tightly bound, the complex will have a well-defined stoichiometry independent of humidity. When, however, the solvent or water is weakly bound the water/solvent content will be dependent on humidity and drying conditions. In such cases, non-stoichiometry will be the norm.

Herein all references to compounds of formula I include references to salts, solvates, prodrugs and multi-component complexes thereof.

The compounds of formula I can be prepared using methods known in the art, for example, 18α- and 18β-glycyrrhetinic acid and their methyl esters may be converted into the corresponding dienones by reaction with 2-iodoxybenzoic acid as per a reported method [8].

The present invention includes radiolabeled forms of the compounds of the invention, for example, compounds of the invention labeled by incorporation within the structure $^3$H, $^{11}$C or $^{14}$C or a radioactive halogen such as $^{125}$I and $^{18}$F. A radiolabeled compound of the invention may be prepared using standard methods known in the art. For example, tritium may be incorporated into a compound of the invention using standard techniques, for example by hydrogenation of a suitable precursor to a compound of the invention using tritium gas and a catalyst. Alternatively, a compound of the invention containing radioactive iodine may be prepared from the corresponding trialkyltin (suitably trimethyltin) derivative using standard iodination conditions, such as [$^{125}$I] sodium iodide in the presence of chloramine-T in a suitable solvent, such as dimethylformamide. The trialkyltin compound may be prepared from the corresponding non-radioactive halo, suitably iodo, compound using standard palladium-catalyzed stannylation conditions, for example hexamethylditin in the presence of tetrakis (triphenylphosphine) palladium (0) in an inert solvent, such as dioxane, and at elevated temperatures. Further, a compound of the invention containing a radioactive fluorine may be prepared, for example, by reaction of K[$^{18}$F]/K222 with a suitable precursor compound, such as a compound of formula I comprising a suitable leaving group, for example a tosyl group, that may be displaced with the $^{18}$F anion.

Methods and Compositions

The present invention relates to novel compounds of formula I, accordingly the present invention includes all uses of these compounds including, for example, in therapeutic and diagnostic applications. The present invention accordingly includes the use of a compound or a combination of compounds of the invention as a medicament or as a diagnostic.

In their ability to inhibit the enzymatic activity of 11β-HSD, certain compounds of the invention are useful for treating any condition or disease that benefits from an inhibition of 11β-HSD. In an embodiment of the invention, the conditions or diseases that benefit from an inhibition of 11β-HSD are chronic inflammatory diseases, autoimmune diseases, skin diseases, bone diseases, metabolic diseases, infectious diseases and cancer.

Accordingly, the present invention includes a method of treating chronic inflammatory diseases, autoimmune diseases, skin diseases, bone diseases, metabolic diseases, infectious diseases and cancer comprising administering an effective amount of a compound of the invention to a subject in need thereof. The invention also includes a use of a compound of the invention to treat chronic inflammatory diseases, autoimmune diseases, skin diseases, bone diseases, metabolic diseases, infectious diseases and cancer and a use of a compound of the invention to prepare a medicament to treat chronic inflammatory diseases, autoimmune diseases, skin diseases, bone diseases, metabolic diseases, infectious diseases and cancer. In embodiments of the invention the chronic inflammatory disease is selected from stomatitis, gingivitis, periodontitis, peri-implantitis and osteoarthritis. In embodiments of the invention the autoimmune disease is selected from rheumatoid arthritis, systemic lupus erythematosus (SLE), Sjögren's syndrome, scleroderma, dermatomyositis, and polymyositis, inflammatory bowel diseases like Crohn's disease and ulcerative colitis. In embodiments of the invention the skin disease is selected from dermatitis, contact dermatitis, allergic dermatitis, atopic dermatitis, psoriasis, eczema, prurigo simplex acuta, prurigo simplex subacuta, prurigo nodularis, alopecia greata, Idiopathic thrombocytopenic purpura, pemphigus vulgaris, actinic keratosis. In embodiments of the invention the bone disease is selected from inflammation and/or immune mediated bone loss, osteoporosis, postmenopausal osteoporosis, Paget's disease, lytic bone metastases, arthritis, juvenile chronic arthritis, adjuvant arthritis, infectious diseases, bone loss by cancer, bone loss by HIV, tooth loss, bone marrow inflammation, synovial inflammation, cartilage and/or bone erosion and/or proteoglycan damage, osteopenie, osteosclerose, osteonecrosis. In embodiments of the invention the metabolic disease or disorder is selected from fasting hyperglycemia, diabetes mellitus, in particular insulin dependent type II diabetes, impaired fasting glucose, impaired glucose tolerance, insulin resistance, high blood pressure, central obesity (also known as visceral adiposity), decreased HDL cholesterol and elevated triglycerides. In embodiments of the invention the infectious disease is selected from viral, bacterial or fungal infections. In embodiments of the invention the cancer is selected from bladder cancer, breast cancer, colorectal cancer, cutaneous melanoma, skin cancer, squamous cell carcinoma of the skin, endometrial cancer, leukemia, lung cancer, non-Hodgkin lymphoma, ovarian cancer, pancreatic cancer, and prostate cancer.

The present invention also includes a method of treating chronic inflammatory diseases, autoimmune diseases, skin diseases, bone diseases, metabolic diseases, infectious diseases and cancer comprising administering an effective amount of a compound of the invention to a subject in need thereof. Further the invention includes a use of a compound of the invention to treat chronic inflammatory diseases, autoimmune diseases, skin diseases, bone diseases, metabolic diseases, infectious diseases and cancer, as well as a use of a compound of the invention to prepare a medicament to treat these diseases.

In an embodiment of the invention the 11β-HSD inhibiting compound is compound 1. A person skilled in the art would be able to identify 11β-HSD inhibiting compounds of the invention using, for example enzyme assays with mammalian 11β-HSD isolated from specific tissue or expressed in transfected cell lines as described in the examples below and in literature [9-12].

In their ability to downregulate the expression or activity of TNFα, the compounds of the invention are useful for treating any condition or disease that benefits from a downregulation in the expression or activity of TNFα. In an embodiment of the invention, the conditions or diseases that that benefit from a downregulation in the expression or activity of TNFα, are inflammatory diseases, in particular rheumatoid arthritis, psoriasis, periodontitis, systemic lupus erythematosus (SLE), Sjögren's syndrome, scleroderma, dermatomyositis, and polymyositis, Crohn's disease and ulcerative colitis, asthma bronchiale.

Accordingly, in a further embodiment of the present invention, there is included a method of treating inflammatory diseases comprising administering a TNFα-downregulating effective amount of a compound of the invention to a subject in need thereof. A person skilled in the art would be able to identify TNFα-downregulating compounds of the invention by contacting one or more cells with a compound of the invention and assaying for the presence of one TNFα and comparing the levels of TNFα in the one or more cells with that of controls. Such methods are known in the art [13,14] and are described in the examples herein below.

The compounds of the invention are suitably formulated into pharmaceutical compositions for administration to human subjects in a biologically compatible form suitable for administration in vivo. Accordingly, in another aspect, the present invention includes a pharmaceutical composition comprising a compound of the invention and a pharmaceutically acceptable carrier or diluent.

The compositions containing the compounds of the invention can be prepared by known methods for the preparation of pharmaceutically acceptable compositions which can be administered to subjects, such that an effective quantity of the active substance is combined in a mixture with a pharmaceutically acceptable vehicle. Suitable vehicles are described in literature [15-17]. On this basis, the compositions include, albeit not exclusively, solutions of the substances in association with one or more pharmaceutically acceptable vehicles or diluents, and contained in buffered solutions with a suitable pH and iso-osmotic with the physiological fluids.

In accordance with the methods of the invention, the described compounds, salts or solvates thereof may be administered to a patient in a variety of forms depending on the selected route of administration, as will be understood by those skilled in the art. The compositions of the invention may be administered, for example, by peroral, parenteral, buccal, sublingual, nasal, rectal, patch, pump or transdermal (topical) administration and the pharmaceutical compositions formulated accordingly. Parenteral administration includes intravenous, intraperitoneal, subcutaneous, intramuscular, transepithelial, nasal, intrapulmonary, intrathecal, rectal and topical modes of administration. Parenteral administration may be by continuous infusion over a selected period of time.

A compound of the invention may be orally administered, for example, with an inert diluent or with an assimilable edible carrier, or it may be enclosed in hard or soft shell gelatin capsules, or it may be compressed into tablets, or it may be incorporated directly with the food of the diet. For oral therapeutic administration, the compound of the invention may be incorporated with excipient and used in the form of ingestible tablets, buccal tablets, troches, capsules, elixirs, suspensions, syrups, wafers, and the like.

A compound of the invention may also be administered parenterally. Solutions of a compound of the invention can be prepared in water suitably mixed with a surfactant such as hydroxypropylcellulose. Dispersions can also be prepared in glycerol, propylene glycol, liquid polyethylene glycols, DMSO and mixtures thereof with or without alcohol, and in oils. Under ordinary conditions of storage and use, these preparations contain a preservative to prevent the growth of microorganisms. A person skilled in the art would know how to prepare suitable formulations.

The pharmaceutical forms suitable for injectable use include sterile aqueous solutions or dispersion and sterile powders for the extemporaneous preparation of sterile injectable solutions or dispersions. In all cases the form must be sterile and must be fluid to the extent that easy syringability exists. Ampoules are convenient unit dosages. In addition, a pharmaceutical form suitable for injectable use includes sterile powders for the direct needle-free injection of the substance into the outer layer of skin in a simple-to-use-device.

Compositions for nasal and pulmonary administration may conveniently be formulated as aerosols, drops, gels and powders. Aerosol formulations typically comprise a solution or fine suspension of the active substance in a physiologically acceptable aqueous or non-aqueous solvent and are usually presented in single or multidose quantities in sterile form in a sealed container, which can take the form of a cartridge or refill for use with an atomizing device.

Alternatively, the sealed container may be a unitary dispensing device such as a single dose inhaler or an aerosol dispenser fitted with a metering valve which is intended for disposal after use. Where the dosage form comprises an aerosol dispenser, it will contain a propellant which can be a compressed gas such as compressed air or an organic propellant such as hydrofluoroalkanes. The aerosol dosage forms can also take the form of a pump-atomizer. Where the dosage form comprises a dry powder inhaler, it can contain a propellant or rely on the force of patient inhalation to entrain powder from the device and subsequently break-up the powder into small aerosol particles.

Compositions suitable for buccal or sublingual administration include tablets, lozenges, pastilles, and patches wherein the active ingredient is formulated with a carrier such as sugar, acacia, tragacanth, or gelatin and glycerine. Compositions for rectal administration are conveniently in the form of suppositories containing a conventional suppository base such as cocoa butter.

Compositions for topical administration may include, for example, propylene glycol, isopropyl alcohol, mineral oil and glycerin. Preparations suitable for topical administration include liquid or semi-liquid preparations such as liniments, lotions, applicants, and oil-in-water or water-in-oil emulsions such as creams, ointments or pastes; or solutions or suspensions such as drops. Moreover, suitable preparations for topical administration include patches wherein the ingredient is formulated with carriers such as adhesives, solvents, or polymers. In addition to the aforementioned ingredients, the topical preparations may include one or more additional ingredients such as diluents, buffers, flavoring agents, binders, surface active agents, thickeners, lubricants, preservatives, e.g. methyl hydroxybenzoate (including anti-oxidants), emulsifying agents and the like.

Sustained or direct release compositions can be formulated, e.g. liposomes or those wherein the active compound is protected with differentially degradable coatings, such as by microencapsulation, multiple coatings, etc or those wherein the compound is inbedded into a polymer matrix such as polylactid or the like. It is also possible to freeze-dry the compounds of the invention and use the lypolizates obtained, for example, for the preparation of products for injection.

The dosage of the compounds of formula I and/or compositions of the invention can vary depending on many factors such as the pharmacodynamic properties of the compound, the mode of administration, the age, health and weight of the recipient, the nature and extent of the symptoms, the frequency of the treatment and the type of concurrent treatment, if any, and the clearance rate of the compound in the human or animal to be treated. One of skill in the art can determine the appropriate dosage based on the above factors. The compounds of formula I may be administered initially in a suitable dosage that may be adjusted as required, depending on the clinical response.

The compounds of the invention may be administered to a subject alone or in combination with pharmaceutically acceptable carriers, as noted above, and/or with other pharmaceutically active agents for the treatment of chronic inflammatory diseases, autoimmune diseases, skin diseases, bone diseases, metabolic diseases, infectious diseases and cancer, the proportion of which is determined by the solubility and chemical nature of the compounds, chosen route of administration and standard pharmaceutical practice.

The compounds of formula I, or salts or solvates thereof, can be used alone or in combination with other agents or therapies that treat inflammatory and autoimmune diseases, for example, but not limited to, non-steroidal anti-inflammatory drugs (NSAIDS), corticosteroids, disease modifying anti-rheumatic drugs (DMARDs), TNFα blockers, interleukin 1 (IL-1) blockers, monoclonal antibodies against B cells, and T cell activation blocker.

The compounds of formula I, or salts or solvates thereof, can be used alone or in combination with other agents or therapies that treat skin diseases, for example, but not limited to, corticosteroids, immunomodulating agents, retinoids, urea, zinc oxide, panthenol, antibiotics, and antimycotics.

The compounds of formula I, or salts or solvates thereof, can be used alone or in combination with other agents or therapies that treat metabolic diseases, for example, but not limited to, sulfonylureas, meglitinides, biguanides, thiazolidinediones (TZDs), and α-glucosidase inhibitors.

The compounds of formula I, or salts or solvates thereof, can be used alone or in combination with other agents or therapies that treat infectious diseases, for example, but not limited to, antibiotics like aminoglycosides, ansamycins, carbacephem, carbapenems, cephalosporins, glycopeptides, macrolides, monobactams, penicillins, polypeptides, quinolones, sulfonamides, and tetracyclines, antimycotics like polyenes, imidazoles, triazoles, allylamines, and echinocandins, and antivirals like cell entry blockers, nucleoside analogues, reverse transcriptase inhibitors, protease inhibitors, and neuraminidase inhibitors.

The compounds of formula I, or salts or solvates thereof, can be used alone or in combination with other agents or therapies that treat cancer, for example, but not limited to, cytotoxic drugs, kinase inhibitors, antibodies and immunotherapy, selective receptor modulators, non-steroidal anti-inflammatory drugs (NSAIDS), corticosteroids, and enzyme modulators.

While the following Examples illustrate the invention in further detail, it will be appreciated that the invention is not limited to the specific examples.

EXAMPLES

Experimental Data

All solvents were purified and dried by standard procedures. Melting points were measured on a Büchi B-545 melting point apparatus or a Kofler hot stage microscope and are uncorrected. Column chromatography was performed on silica gel 60 (230-400 mesh, Merck). Reactions were monitored by TLC on silica gel 60 $F_{254}$ pre-coated glass plates (Merck) or on silica gel 60 $F_{254}$ HPTLC pre-coated glass plates with 2.5 cm concentration zone (Merck); spots were detected by UV light examination or visualized by spraying with anisaldehyde sulfuric acid, molybdophosphoric acid, mixture of molybdophosphoric acid and CeIV ammonium nitrate or ninhydrine and heating. Concentration of solutions was performed at reduced pressure at temperatures <50° C. NMR spectra were recorded at 297 K in $CDCl_3$, pyridine-$d_5$, DMSO-$d_6$ or MeOD with a Bruker AC 200 spectrometer ($^1H$ at 200.13 MHz, $^{13}C$ at 50.31 MHz), a Bruker DPX 300 spectrometer ($^1H$ at 300.13 MHz, $^{13}C$ at 75.47 MHz), a Bruker AC 400 spectrometer ($^1H$ at 400.13 MHz, $^{13}C$ at 100.61 MHz) and with a Bruker DPX 400 spectrometer ($^1H$ at 400.13 MHz, $^{13}C$ at 100.61 MHz) using standard Bruker NMR software. $^1H$ NMR spectra were referenced to tetramethylsilane. $^{13}C$ NMR spectra were referenced to chloroform (δ 77.00). Infrared spectra were recorded on a BIORAD ATR-FT-IR spectrometer as solutions in DCM or MeOH. Elemental analyses were measured with an EA 1108 CHNS-O from Carlo Erba. Compounds were purified by MPLC (medium pressure liquid chromatography) using preparative silica gel (40-63 mm) columns. HPLC was performed using a Waters 2695 instrument with Merck Chromolith RP18 columns and a gradient of 3% to 60% acetonitrile and water containing HCOOH 0.1% at a flow of 1.0 to 3.0 mL/min. Preparative LC was performed using a Waters instrument with Merck Geminy RP18 columns and a gradient of 3% to 60% acetonitrile and water containing HCOOH 0.1% at a flow of 25 mL/min. The HPLC reported purity is the number generated for the peak area as calculated using the Waters Millennium software with the Maxplot option for the UV maximum of the corresponding peak. Mass spectra were measure in CI-mode with ammonia as a reagent gas on a thermo scientific.

General Synthetic Procedure for the Preparation of the Hydroxamic Acids

To a stirred solution of the appropriate acid chloride (1 mmol) in methylene chloride (30 mL) were added the hydroxylamine derivate as HCl salt (1.2 mmol), and triethylamine (2 mmol). The mixture was stirred under nitrogen at room temperature for 16-24 h. When TLC showed the completion of the reaction, the reaction mixture was poured into water and extracted with methylene chloride (2×30 mL). The combined organic phase was washed with 2% HCl (20 mL) and water (20 mL), dried over magnesium sulfate and filtered. Evaporation of the solvent gave a residue which was purified by flash chromatography (SiO2, methylene chloride methanol, gradient elution) to give the hydroxamic acid as product.

General Procedure for Deprotection of 3-Acetylated Hydroxamic Acids

To a stirred solution of the appropriate protected compound (0.55 mmol) in methanol (25 ml) were added KOH pellets (5.5 mmol) and the reaction mixture was stirred at RT. After 48 h the solvent was removed under vacuum and water (25 ml) was added to the residue. The aqueous layer was extracted in DCM (3 times 25 ml) and the combined organic layers were then washed with 2N HCl and finally with water (je 30 ml). The separated organic layer was dried over $Na_2SO_4$, filtered and the solvent evaporated. Purification of the crude product on silica with a mixture of 0-5% methanol in methylene chloride yielded the final product as white powder.

Example 1

Compound 1 (Reference)

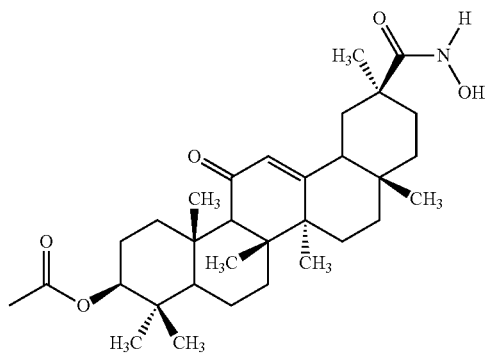

(3S,18R,20S)-3-(Acetyloxy)-N-hydroxy-11-oxo-olean-12-en-29-amide (3S,18R,20S)-3-(Acetyloxy)-11-oxo-olean-12-en-29-oic acid was reacted with hydroxylamine hydrochloride to (3S,18R,20S)-3-(acetyloxy)-N-hydroxy-11-oxo-olean-12-en-29-amide according to the general synthetic procedure for the preparation of the hydroxamic acids.

$^1$H NMR (200 MHz, DMSO-$d_6$): δ 8.3 (br, 1H), 7.8 (br, 1H), 5.24 (s, 1H), 4.16 (m, 1H), 2.48-0.22 (m, 21H), 1.73 (s, 3H), 1.08 (s, 3H), 1.02 (s, 3H), 0.80 (s, 3H), 0.76 (s, 3H), 0.56 (s, 6H), 0.47 (s, 3H).

$^{13}$C NMR (200 MHz, DMSO-$d_6$): δ 198.9, 172.2, 170.0, 169.7, 127.4, 79.6, 60.8, 53.7, 47.5, 44.8, 43.0, 41.8, 40.6, 2, 37.8, 37.6, 37.2, 36.5, 32.0, 31.3, 30.2, 28.7, 28.3, 27.7, 26.0, 25.9, 23.2, 23.0, 21.0, 18.3, 16.9, 16.6, 16.1

Example 2

Compound 2 (Reference)

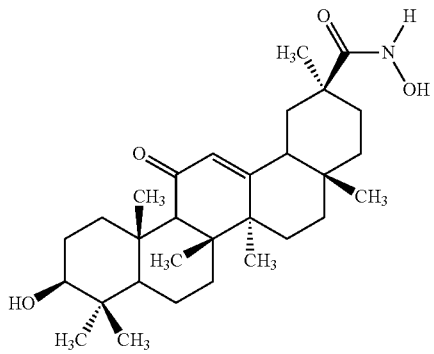

(3S,18R,20S)-3-Hydroxy-N-hydroxy-11-oxo-olean-12-en-29-amide (3S,18R,20S)-3-(Acetyloxy)-N-hydroxy-11-oxo-olean-12-en-29-amide was hydrolyzed to (3S,18R,20S)-3-hydroxy-N-hydroxy-11-oxo-olean-12-en-29-amide according to the general procedure for deprotection of 3-acetylated hydroxamic acids $^1$H NMR (200 MHz, pyridine-$d_5$): δ 8.51 (s, 1H), 6.10 (br, 1H), 3.42 (m, 1H), 3.10 (m, 1H), 1.52-0.58 (m, 22H), 1.36 (s, 3H), 1.28 (s, 6H), 1.23 (s, 3H), 1.07 (s, 3H), 1.04 (s, 3H), 0.67 (s, 3H).

$^{13}$C NMR (200 MHz, DMSO-$d_6$): δ 200.1, 173.7, 169.9, 129.0, 78.4, 62.6, 55.8, 48.8, 45.9, 43.9, 43.2, 42.3, 40.2 (2C), 38.4, 38.0, 33.4, 32.4, 31.8, 30.0, 29.2, 28.9, 28.6, 27.3, 27.1, 23.9, 19.2, 18.4, 17.3, 17.0

Example 3

Compound 3

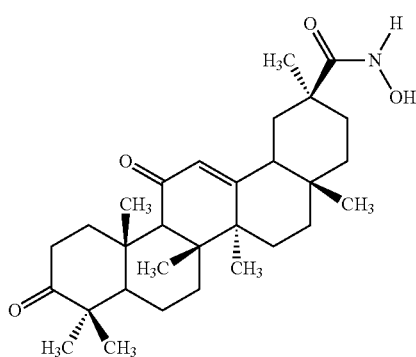

(18R,20S)-N-Hydroxy-3,11-dioxo-olean-12-en-29-amide

To a stirred solution of (18R,20S)-3,11-dioxo-olean-12-en-29-oic acid (940 mg, 2.0 mmol) in 15 mL terahydrofurane were added at 0° C. triethyl amine (1.0 mL, 10 mmol) and chloroformic acid ethyl ester (250 μL, 2.5 mmol). The reaction mixture was stirred at 0° C. for 10 min fallowed by addition of hydroxylamine hydrochloride (470 mg, 6.6 mmol). After 15 h stirring at RT (room temperature), the solvent was evaporated and the residue purified by column chromatography (100 g SiO$_2$, 0-5% methanol in methylene chloride) to yield the final product (340 mg, 35%) as white powder.

$^1$H NMR (200 MHz, CDCl$_3$): δ 5.65 (s, 1H), 2.90 (m, 1H), 2.60 (m, 1H), 2.50-0.75 (m, 15H), 1.35 (s, 3H), 1.23 (s, 3H), 1.22 (s, 3H), 1.14 (s, 3H), 1.07 (s, 3H), 1.04 (s, 3H), 0.85 (s, 3H)

$^{13}$C NMR (50 MHz, CDCl$_3$): δ 217.1, 199.2, 172.2, 169.0, 128.6, 61.0, 55.3, 48.0, 47.7, 45.4, 45.2, 43.3, 40.9, 39.8, 37.3, 36.7, 34.1, 31.9 (2C), 30.8, 28.4, 27.4, 26.4, 26.3, 26.2, 23.4, 21.3, 18.8, 18.5, 15.7

Example 4

Compound 4

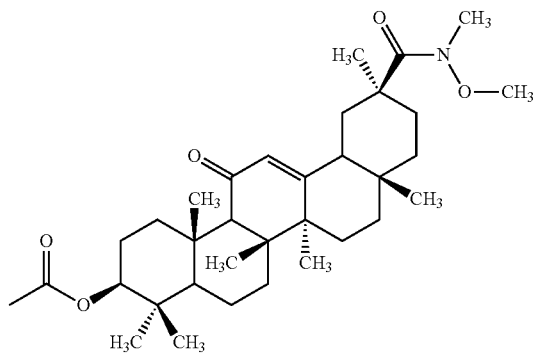

(3S,18R,20S)-3-(Acetyloxy)-N-methyl-N-methoxy-11-oxo-olean-12-en-29-amide (3S,18R,20S)-3-(Acetyloxy)-11-oxo-olean-12-en-29-oic acid was reacted with O,N-dimethyl-hydroxylamine hydrochloride to (3S,18R,20S)-3-(acetyloxy)-N-methyl-N-methoxy-11-oxo-olean-12-en-29-amide according to the general synthetic procedure for the preparation of the hydroxamic acids.

$^1$H NMR (200 MHz, CDCl$_3$) δ 5.63 (s, 1H), 4.44 (dd, 1H), 3.60 (s, 3H), 3.11 (s, 3H), 2.72 (dt, 1H), 2.32-0.66 (m, 20H), 1.98 (s, 3H), 1.30 (s, 3H), 1.12 (s, 3H), 1.10 (s, 3H), 1.06 (s, 3H), 0.81 (s, 6H), 0.75 (s, 3H)

$^{13}$C NMR (50 MHz, CDCl$_3$) δ 200.0, 176.8, 170.9, 169.7, 128.4, 80.6, 61.6, 60.5, 55.0, 48.3, 45.3, 44.7, 43.2, 42.3, 38.8, 38.0, 37.9, 36.9, 33.8, 32.7, 31.9, 31.9, 28.4, 28.0, 26.7, 26.5, 26.2, 23.5, 23.1, 21.3, 18.6, 17.3, 16.6, 16.4

Example 5

Compound 5

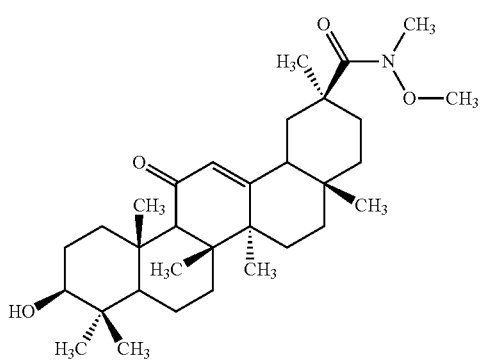

(3S,18R,20S)-3-Hydroxy-N-methyl-N-methoxy-11-oxo-olean-12-en-29-amide (3S,18R,20S)-3-(Acetyloxy)-N-methyl-N-methoxy-11-oxo-olean-12-en-29-amide was hydrolyzed to (3S,18R,20S)-3-hydroxy-N-methyl-N-methoxy-11-oxo-olean-12-en-29-amide according to the general procedure for deprotection of 3-acetylated hydroxamic acids $^1$H NMR (200 MHz, CDCl$_3$): δ 5.64 (s, 1H), 3.61 (s, 3H), 3.35 (m, 1H), 3.12 (s, 3H), 2.70 (m, 1H), 2.31-0.58 (m, 26H), 1.30 (s, 3H), 1.12 (s, 3H), 1.06 (s, 3H), 1.05 (s, 3H), 0.94 (s, 3H), 0.74 (s, 3H)

$^{13}$C NMR (50 MHz, CDCl$_3$): δ 200.4, 176.9, 169.9, 128.4, 78.8, 61.7, 60.6, 54.9, 48.3, 45.3, 44.8, 43.3, 42.4, 39.1 (2C), 37.9, 37.0, 33.9, 32.8, 31.9 (2C), 28.4, 28.1, 27.2, 26.7, 26.5, 26.2, 23.1, 18.7, 17.5, 16.4, 15.6

Example 6

Compound 6

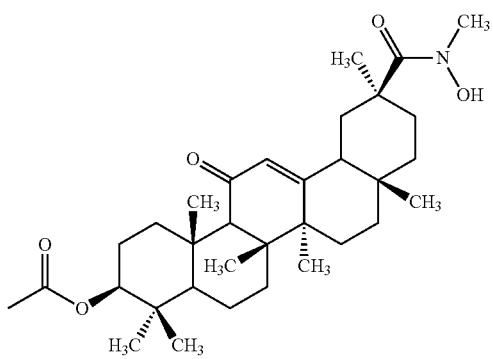

(3S,18R,20S)-3-(Acetyloxy)-N-hydroxy-N-methyl-11-oxo-olean-12-en-29-amide (3S,18R,20S)-3-(Acetyloxy)-11-oxo-olean-12-en-29-oic acid was reacted with N-methyl-hydroxylamine hydrochloride to (3S,18R,20S)-3-(Acetyloxy)-N-methyl-N-hydroxy-11-oxo-olean-12-en-29-amide according to the general synthetic procedure for the preparation of the hydroxamic acids.

$^1$H NMR (200 MHz, CDCl$_3$): δ 5.59 (s, 1H), 4.44 (s, 1H), 3.27 (t, 3H), 2.70 (m, 1H), 2.35-0.70 (m, 21H), 1.98 (s, 3H), 1.28 (s, 3H), 1.13 (s, 3H), 1.10 (s, 3H), 1.05 (s, 3H), 0.81 (s, 6H), 0.74 (s, 3H)

$^{13}$C NMR (50 MHz, CDCl$_3$): δ 200.8, 174.4, 174.2, 171.0, 128.1, 80.6, 61.7, 55.0, 48.5, 45.4, 43.6, 43.4, 42.3, 38.8, 38.3, 38.0, 37.7, 36.9, 32.7, 32.6, 31.8, 28.5, 28.0, 26.7, 26.4, 26.2, 23.5, 23.1, 21.3, 18.6, 17.3, 16.6, 16.4

Example 7

Compound 7

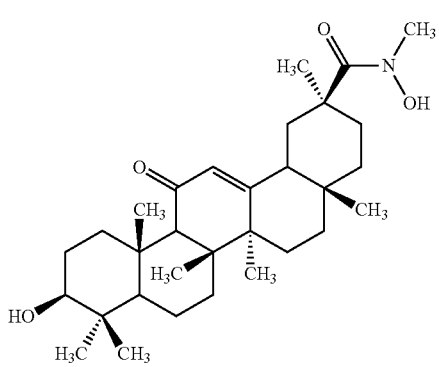

(3S,18R,20S)-3-Hydroxy-N-hydroxy-N-methyl-11-oxo-olean-12-en-29-amide (3S,18R,20S)-3-(Acetyloxy)-N-methyl-N-hydroxy-11-oxo-olean-12-en-29-amide was hydrolyzed to (3S,18R,20S)-3-hydroxy-N-methyl-N-hydroxy-11-oxo-olean-12-en-29-amide according to the general procedure for deprotection of 3-acetylated hydroxamic acids $^1$H NMR (200 MHz, Pyridine, d$_5$): δ: 8.69 (s, 2H), 6.05 (m, 1H), 3.56 (s, 1H), 3.46 (s, 3H), 2.70 (m, 1H), 2.49 (m, 1H), 0.5-2.0 (m, 40H)

$^{13}$C NMR (50 MHz, Pyridine, d$_5$) 200.17, 176.46, 170.61, 129.14, 78.37, 62.62, 55.80, 50.12, 49.12, 45.95, 45.08, 44.03, 43.78, 40.26, 40.25, 39.07, 39.03, 38.09, 33.51, 32.59, 32.28, 29.22, 28.60, 27.43, 27.25, 26.75, 23.71, 19.32, 18.41, 17.30, 17.06

Example 8

Compound 8

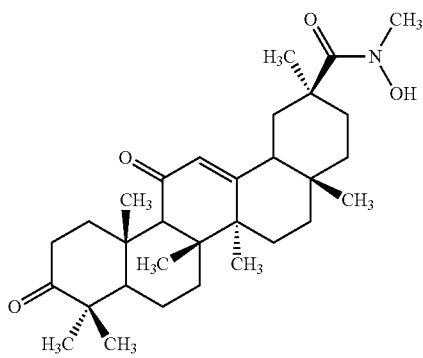

(18R,20S)-N-Hydroxy-N-methyl-3,11-dioxo-olean-12-en-29-amide

Cr(VI)O$_3$ (3.25 g, 21.38 mmol) was dissolved in a mixture of H$_2$SO$_4$ (conc.) (3.3 mL)-water (9.8 mL) at 0° C. within around 30 minutes and was stirred until use. Jones' reagent was added dropwise via a dropping funnel to a stirred solution (mechanical stirrer) of glycyrrhetinic acid (9.0 g, 19.12 mmol, 1.0 equiv) in THF (31 mL) at −10° C. (ice-EtOH) keeping the temperature below 0° C. After around ⅔ of the addition a lot of precipitate was formed. After complete addition of reagent, the reaction mixture was allowed to come to RT and was stirred under TLC monitoring (DCM:MeOH 20:1). Upon complete conversion (1 h) water (90 mL) was added and the mixture was stirred for several minutes before the precipitated solid was filtered and washed with water several times. The residue was taken up in THF/MeOH (150:10 mL) and dried over $Na_2SO_4$, filtered and evaporated. The offwhite solid was recrystallized from MeOH/DCM to give 8.1 g (94.9%) (18R,20S)-3,11-dioxo-olean-12-en-29-oic acid as white crystals, giving spectral data consisting with the literature.

(18R,20S)-3,11-Dioxo-olean-12-en-29-oic acid (2.0 g, 4.267 mmol, 1.0 equiv) was suspended in dry DCM (40 mL) and DMF (20 drops, syringe-needle) and oxalylchloride (0.49 mL, 5.12 mmol, 1.2 equiv) was added at 0° C. and the reaction mixture was allowed to come to RT and was stirred under TLC monitoring (sample from MeOH solution, $SiO_2$:He:EtOAc 2:1). The suspension turned a clear solution the reaction was complete after around 40 minutes. The reaction mixture was evaporated at RT, coevaporated from DCM once and redissolved in DCM. The clear solution was chilled to 0° C. and first TEA (2.379 mL, 17.1 mmol, 4.0 equiv) and then N-methylhydroxylamine was added in one portion. The reaction mixture had turned yellowish already at the addition of TEA and this colour was intensified during the reaction. Already after several minutes complete conversion was detected ($SiO_2$:Hex:EtOAC 2:1 and $NH_2$—$SiO_2$:DCM:MeOH 20:1). The reaction mixture was diluted with DCM and washed with 1N HCl, $NaHCO_3$ and brine, dried over $Na_2SO_4$ and evaporated to give a crude material, which was purified by column chromatography ($SiO_2$: 115 g, DCM:MeOH 45:1 to 35:1) and column chromatography on $SiO_2$—$NH_2$ (15 g, DCM to DCM:MeOH 50:1) to give pure (18R,20S)-N-hydroxy-N-methyl-3,11-dioxo-olean-12-en-29-amide free of starting material (1.48 g, 69.7%).

Optical rotation: $[\alpha]_D^{20}$=+164.4 (c=0.55 in $CHCl_3$)

$^1$H-NMR: δ 0.83 (s, 3H, H28), 1.00-1.08 (m, 1H, H16b), 1.07 (s, 3H, H23/24), 1.10 (s, 3H, H23/24), 1.16 (s, 3H, H26), 1.2 (s, 3H, H29), 1.21-1.36 (m, 3H, H5, H15b, H21b), 1.26 (s, 3H, H25), 1.33-1.46 (m, 2H, H1b, H22b), 1.37 (s, 3H, H27), 1.41-1.64 (m, 6H, H6a, H6b, H7a, H7b, H19b, H22a), 1.86 (td, J=13.6 Hz, J=4.3 Hz, 1H, H15a), 2.09 (td, J=13.6 Hz, J=4.3 Hz, 1H, H16a), 2.18-2.25 (m, 3H, H18, H19a, H21a), 2.37 (ddd, J=15.8 Hz J=6.5 Hz J=4.1 Hz, 1H, H2b), 2.45 (s, 1H, H9), 2.62 (ddd, J=15.8 Hz J=11.1 Hz J=7.1 Hz, 1H, H2a), 2.93 (ddd, J=13.5 Hz, J=7.1 Hz, J=4.1 Hz, 1H, H1a), 3.36 (s, 3H, NMe), 5.69 (s, 1H, H12)

$^{13}$C-NMR: δ 15.7 (q, C25), 18.5 (q, C26), 18.7 (t, C7), 21.4 (q, C23/24), 23.1 (q, C27), 26.3 (q, C29), 26.4 (q, C23/24), 26.5 (t, C15), 26.7 (t, C16), 28.6 (q, C28), 31.9 (s, C20), 32.1 (t, C6), 32.5 (t, C21), 34.2 (t, C2), 36.7 (s, C10), 37.7 (t, C22), 38.3 (q, NMe), 39.7 (t, C1), 42.5 (t, C19), 43.5 (s, C8/20), 43.6 (s, C8/20), 45.3 (s, C14), 47.8 (s, C4), 48.5 (d, C18), 55.4 (d, 5), 61.1 (d, C9), 128.1 (d, C12), 171.4 (s, C13), 174.0 (s, C30), 200.2 (s, C11), 217.4 (s, C3)

Example 9

Compound 9

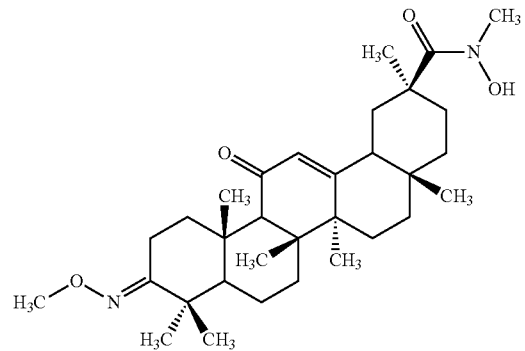

(18R,20S)-N-Hydroxy-N-methyl-3-(methoxyimino)-11-dioxo-olean-12-en-29-amide

A solution of (18R,20S)-N-hydroxy-N-methyl-3,11-dioxo-olean-12-en-29-amide (500 mg, 1.005 mmol, 1.0 equiv) and methoxylamine-hydrochloride (252 mg, 3.014 mmol, 3.0 equiv) in dry pyridine (5 mL) was stirred at RT under TLC monitoring (DCM:MeOH 40:1). Upon complete conversion (3 h), the reaction mixture was diluted with DCM and was washed with chilled 10% HCl, $NaHCO_3$, and brine, dried over $Na_2SO_4$, and evaporated to leave a crude material, which was purified by column chromatography ($SiO_2$: 25 g DCM:MeOH 60:1 to DCM:MeOH 50:1) to give (18R,20S)-N-hydroxy-N-methyl-3-(methoxyimino)-11-dioxo-olean-12-en-29-amide (536 mg, 101.3%) as white solid foam.

Optical rotation: $[\alpha]_D^{20}$=+96.7 (c=0.5 in $CHCl_3$)

$^1$H-NMR: δ 0.82 (s, 3H, H28), 0.96-1.05 (m, 3H, H1b, H5, H16b), 1.07 (s, 3H, H23/24), 1.12-1.24 (m, 1H, H15b), 1.14 (s, 3H, H26), 1.18 (s, 3H, H23/24), 1.19 (s, 3H, H29), 1.22 (s, 3H, H25), 1.23-1.40 (m, 2H, H21b, H22b), 1.34 (s, 3H, H27), 1.38-1.68 (m, 6H, H6a, H6b, H7a, H7b, H19b, H22a), 1.83 (td, J=13.5 Hz, J=4.1 Hz, 1H, H15a), 1.99-2.14 (m, 1H, H16a), 2.11-2.24 (m, 4H, H2b, H18, H19a, H21a), 2.38 (s, 1H, H9), 2.72-2.82 (m, 1H, H1a), 2.86-2.96 (m, 1H, H2a), 3.36 (s, 3H, NMe), 3.82 (s, 3H, OMe), 5.66 (s, 1H, H12)

$^{13}$C-NMR: δ 15.7 (q, C25), 17.7 (t, C2), 18.2 (t, C7), 18.6 (q, C26), 23.1 (q, C27), 23.4 (q, C23/24), 26.3 (q, C29), 26.5 (t, C15), 26.7 (t, C16), 27.3 (q, C23/24), 28.5 (q, C28), 31.9 (s, C17), 32.5, 32.7 (2×t, C6, C21), 37.0 (s, C10), 37.7 (t, 22), 38.3 (q, CNMe), 39.1 (t, C1), 40.1 (s, C4), 42.4 (t, C19), 43.4, 43.5 (2×s, C8, C20), 45.4 (s, C14), 48.5 (d, C18), 55.6 (d, C5), 61 (q, COMe), 61.4 (d, C9), 128.2 (d, C12), 165.6 (s, C3), 170.9 (s, C13), 173.7 (s, C30), 200.5 (s, C11)

Example 10

Compound 10

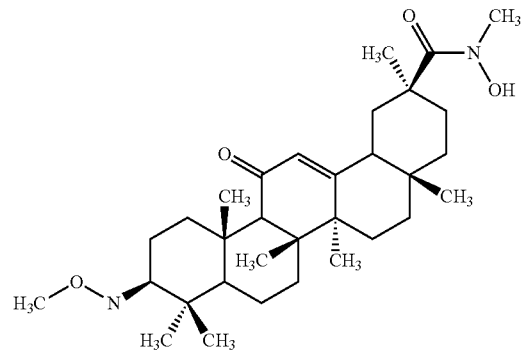

(3S,18R,20S)-N-Hydroxy-N-methyl-3-methoxamino-11-dioxo-olean-12-en-29-amide (18R,20S)-N-Hydroxy-N-methyl-3-(methoxyimino)-11-dioxo-olean-12-en-29-amide (275 mg, 0.522 mmol, 1.0 equiv) was dissolved in around dioxane:EtOH 2:1 (12 mL). This solution was chilled to 0° C. before $BH_3.tBu\text{-}NH_2$ (91 mg, 1.044 mmol, 2.0 equiv) was added at 0° C. and five minutes later 3N HCl was added dropwise via syringe. The reaction mixture was stirred at 0° C. for several hours. After sometime the reaction mixture became milky turbid but well stirrable. According to TLC almost all starting material was converted to target compounds. Addition of another equivalent of $BH_3.tBu\text{-}NH_2$ and HCl did not lead to further conversion. The reaction mixture was worked up by pouring on $NaHCO_3$, and extraction with EtOAc (TLC check), washing of the organic layers with brine, drying over $Na_2SO_4$ and evaporation. Drying in vacuo overnight gave around 280 mg of crude material, which was purified by column chromatography (MPLC, $SiO_2$: 30 g, DCM:Et2O 2:1) and recrystallization from DCM:MeOH to gain pure (3S,18R,20S)-N-hydroxy-N-methyl-3-methoxamino-11-dioxo-olean-12-en-29-amide (50 mg, 18.1%), which could be precipitated as hydrochloride salt by taking up in THF and precipitating with HCl in ether (1M, 2 equiv) and washing with $Et_2O$.

Optical rotation: $[\alpha]_D^{20}$=(c=0.5 in $CHCl_3$)

Example 11

Compound 11

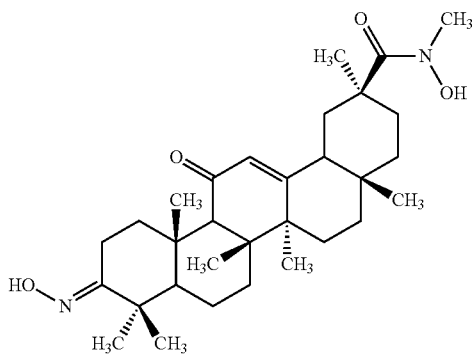

(18R,20S)-N-Hydroxy-3-imino-N-methyl-11-dioxo-olean-12-en-29-amide

A solution of (18R,20S)-N-hydroxy-N-methyl-3,11-dioxo-olean-12-en-29-amide (320 mg, 0.643 mmol, 1.0 equiv) and hydroxylamine-hydrochloride (223 mg, 3.215 mmol, 5.0 equiv) in dry pyridine (4 mL) was stirred at RT under TLC monitoring (DCM:MeOH 40:1) Upon complete conversion (3 h), the reaction mixture was diluted with DCM and washed with chilled 10% HCl, $NaHCO_3$, and brine, dried over $Na_2SO_4$, and evaporated to leave white solid as crude material, which was redissolved in MeOH and evaporated to give fine white solid, which was triturated from DCM to give pure (18R,20S)-N-hydroxy-3-imino-N-methyl-11-dioxo-olean-12-en-29-amide (320 mg, 97%) as white solid.

Optical rotation: $[\alpha]_D^{20}$=+110.8 (c=1.0 in $CHCl_3$)

$^1$H-NMR: δ 0.82 (s, 3H, H28), 0.97-1.16 (m, 3H, H1b, H5, H16b), 1.07 (s, 3H, H23/24), 1.15-1.27 (m, 2H, H15b, H21b), 1.15 (s, 3H, H26), 1.17 (s, 3H, H23/24), 1.2 (s, 3H, H29), 1.23 (s, 3H, H25), 1.31-1.40 (m, 2H, H6b, H22b), 1.35 (s, 3H, H27), 1.44-1.73 (m, 5H, H6a, H7a, H7b, H19b, H22a), 1.85 (td, J=13.6 Hz, J=4.4 Hz, 1H, H15a), 2.02-2.15 (m, 1H, H16a), 2.13-2.33 (m, 1H, H2b, H18, H19a, H21a), 2.41 (s, 1H, H9), 2.75-2.85 (m, 1H, H1a), 3 (dt, J=15.6 Hz, J=4.6 Hz, 1H, H2a), 3.26 (s, 3H, NMe), 5.70 (s, 1H, H12)

$^{13}$C-NMR: δ 15.6 (q, C25), 17.1 (t, C2), 18.1 (t, C7), 18.5 (q, C26), 22.9 (q, C27), 23.2 (q, C23/24), 25.9 (q, C29), 26.4 (t, C16), 26.6 (t, C15), 27.2 (q, C23/24), 28.5 (q, C28), 31.8 (s+t, C17, C21), 32.3 (t, C6), 37 (s, C10), 37.7 (t, C22), 38 (q, NMe), 38.9 (t, C1), 40.2 (s, C4), 42.1 (t, C19), 43.5 (s, C20), 44.1, 45.3 (2×s, C8, C14), 48.7 (d, C18), 55.4 (d, C5), 61.3 (d, C9), 127.7 (d, C12), 166.8 (s, C3), 171.9 (s, C13), 175.5 (s, C30), 201.1 (s, C11)

Example 12

Compound 12

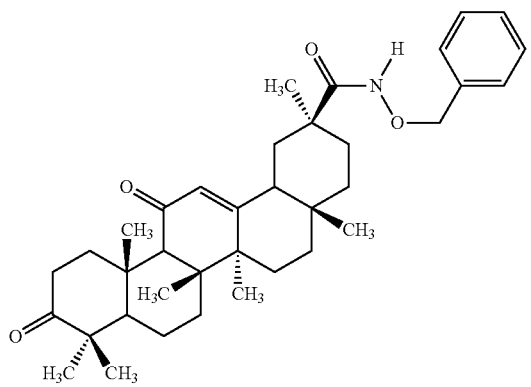

(18R,20S)-N-(Benzyloxy)-N-methyl-3,11-dioxo-olean-12-en-29-amide

Carboxylic acid was suspended in dry toluene and $SOCl_2$ was added at 0° C. and the reaction mixture was allowed to come to RT and was stirred for 3 h. According to TLC (DCM:MeOH 9:1, 5 min standing in MeOH) no starting material was converted. Since still a lot of undissolved material was observed first 3 mL of dry DCM were added and then the reaction mixture was heated to 60° C. for several hours. After around 2 h the reaction mixture clarified and according to TLC almost all starting material was converted to acid chloride (detected as methylester). The reaction was allowed to come to RT, was evaporated the residue was coevaporated from toluene at RT three times and the residue was dissolved in $CH_3CN$ (5 mL) and was stirred at 0° C. when first TEA and then a solution of $BnONH_2$ in $CH_3CN$ was added at 0° C. and the reaction mixture was allowed to come to RT and stirred for 40 h. The reaction mixture was poured on $NaHCO_3$/ice. The aqueous layer was extracted with DCM, the combined organic layers were washed with diluted chilled HCl, with $NaHCO_3$, water and brine, dried over $Na_2SO_4$ and evaporated to give crude material, which was purified by column chromatography ($SiO_2$: 20 g, DCM:MeOH 50:1)

$^1$H-NMR: δ 0.81 (s, 3H, H28), 0.97-1.05 (m, 1H, H16b), 1.07 (s, 3H, H23/24), 1.1 (s, 3H, H23/24), 1.12 (s, 3H, H29), 1.16 (s, 3H, H26), 1.15-1.23 (m, 1H, H15b), 1.27 (s, 3H, H25), 1.25-1.32 (m, 1H, H5), 1.31 (s, 3H, H27), 1.32-1.42 (m,

4H, H1b, H21b, H22a, H22b), 1.4-1.48 (m, 1H, H6b), 1.49-1.60 (m, 2H, H7a, H7b), 1.60-1.69 (m, 3H, H6a, H19a, H19b), 1.78-1.87 (m, 1H, H15a), 1.84-1.92 (m, 1H, H21a), 2.00 (dt, J=13.6 Hz, J=4.3 Hz, 1H, H16a), 2.05-2.13 (m, 1H, H18), 2.3-2.40 (m, 1H, H2b), 2.39 (s, 1H, H9), 2.57-2.68 (m, 1H, H2a), 2.90-3.00 (m, 1H, H1a), 4.94 (bs, 2H, PhCH2O), 5.50 (s, 1H, H12), 7.35-7.45 (m, 5H, 5×Ph-H), 8.31 (s, 1H, NH)

$^{13}$C-NMR: δ 15.6 (q, C25), 18.5 (q, C26), 18.7 (t, C7), 21.4 (q, C23/24), 23.3 (q, C27), 26.31 (t, C15/16), 26.35 (q, C23/24), 26.4 (t, C15/16), 28.4 (q, C28), 29.5 (q, C29), 31.2 (t, C21), 31.8 (s, C17), 32.1 (t, C6), 34.2 (t, C2), 36.7 (s, C10), 37.3 (t, C22), 39.8 (t, C1), 41.3 (t, C19), 43.0 (s, C20), 43.2 (s, C14), 45.1 (s, C8), 47.78 (s, C4), 47.84 (d, C18), 55.4 (d, C5), 61.0 (d, C9), 78.0 (t, PhCH2O), 128.4 (d, OBn), 128.7 (d, OBn), 128.9 (d, C12), 129.3 (d, OBn), 135.3 (s, OBn), 169.2 (s, C13), 173.6 (s, C30), 199.3 (s, C11), 217.2 (s, C3)

Example 13

Compound 13

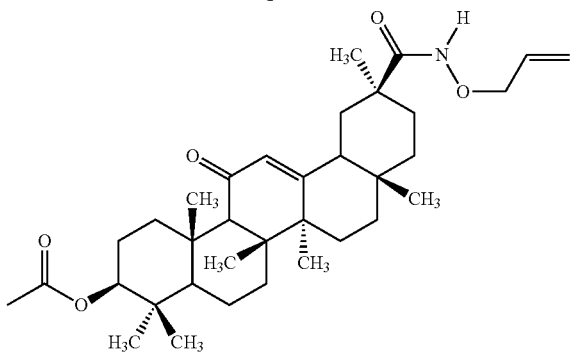

(3S,18R,20S)-3-(Acetyloxy)-N-(2-propen-1-yloxy)-11-oxo-olean-12-en-29-amide (3S,18R,20S)-3-(Acetyloxy)-11-oxo-olean-12-en-29-oic acid was reacted with O-(2-propen-1-yl)-hydroxylamine hydrochloride to (3S,18R,20S)-3-(acetyloxy)-N-(2-propen-1-yloxy)-11-oxo-olean-12-en-29-amide according to the general synthetic procedure for the preparation of the hydroxamic acids.

$^1$H NMR (200 MHz, CDCl$_3$): δ 9.48 (s, 1H), 5.93 (m, 1H), 5.65 (m, 1H), 5.26 (m, 2H), 4.43 (m, 1H), 4.34 (m, 2H), 2.70 (m, 1H), 2.40-0.65 (m, 20H), 2.00 (s, 3H), 1.30 (s, 3H), 1.1 (s, 6H), 1.07 (s, 3H), 0.82 (s, 6H), 0.76 (s, 3H)

$^{13}$C NMR (50 MHz, CDCl$_3$): δ 200.3, 173.5, 171.0, 169.8, 132.9, 128.3, 120.3, 80.6, 77.1, 61.7, 54.9, 53.4, 48.0, 45.4, 43.2, 42.8, 40.9, 38.8, 38.0, 37.3, 36.8, 32.6, 31.7, 31.2, 29.2, 28.4, 28.0, 26.4, 23.4, 23.2, 21.2, 18.6, 17.3, 16.6, 16.3

Example 14

Compound 14

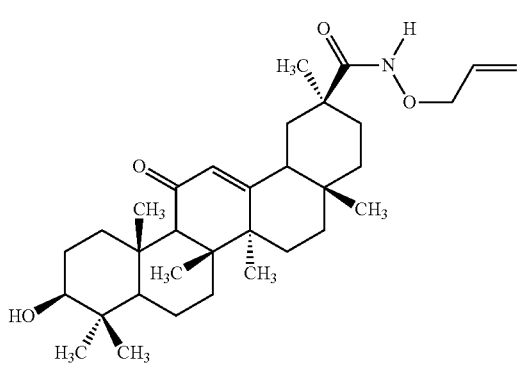

(3S,18R,20S)-3-Hydroxy-N-(2-propen-1-yloxy)-11-oxo-olean-12-en-29-amide (3S,18R,20S)-3-(Acetyloxy)-N-(2-propen-1-yloxy)-11-oxo-olean-12-en-29-amide was hydrolyzed to (3S,18R,20S)-3-hydroxy-N-(2-propen-1-yloxy)-11-oxo-olean-12-en-29-amide according to the general procedure for deprotection of 3-acetylated hydroxamic acids $^1$H NMR (200 MHz, CDCl$_3$): δ 9.05 (s, 1H), 6.00 (m, 1H), 5.67 (s, 1H), 5.34 (d, 1H), 5.28 (s, 1H), 4.38 (d, 2H), 3.21 (m, 1H), 2.75 (m, 1H), 2.72 (m, 1H), 2.33-0.65 (m, 20H), 1.34 (s, 3H), 1.14 (s, 3H), 1.11 (s, 6H), 0.98 (s, 3H), 0.80 (s, 3H), 0.79 (s, 3H)

$^{13}$C NMR (50 MHz, CDCl$_3$): δ 200.4, 173.8, 169.4, 132.7, 128.5, 120.6, 78.8, 64.5, 61.8, 55.0, 47.9, 45.4, 43.2, 42.9, 41.1, 39.2 (2C), 37.3, 37.1, 32.7, 31.4, 31.2, 29.4, 28.4, 28.1, 27.2, 26.4, 26.3, 23.3, 18.7, 17.5, 16.3, 15.6

Example 15

Compound 15

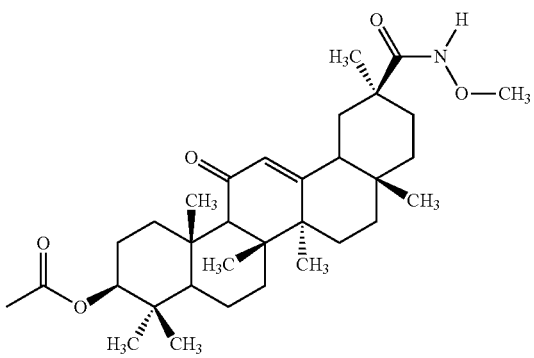

(3S,18R,20S)-3-(Acetyloxy)-N-methoxy-11-oxo-olean-12-en-29-amide (3S,18R,20S)-3-(Acetyloxy)-11-oxo-olean-12-en-29-oic acid was reacted with O-methyl-hydroxylamine hydrochloride to (3S,18R,20S)-3-(acetyloxy)-N-methoxy-11-oxo-olean-12-en-29-amide according to the general synthetic procedure for the preparation of the hydroxamic acids.

$^1$H NMR (200 MHz, CDCl$_3$): δ 9.80 (br, 1H), 5.67 (s, 1H), 5.67 and 5.28 (s, 1H), 4.47 (dd, 1H), 3.72 (s, 3H), 2.75 (m, 1H), 2.70-0.40 (m, 19H), 2.02 (s, 3H), 1.32 (s, 3H), 1.12 (s, 6H), 1.09 (s, 3H), 0.85 (s, 6H), 0.79 (s, 3H)

$^{13}$C NMR (50 MHz, CDCl$_3$): δ 200.3, 173.6, 171.1, 169.6, 128.4, 80.6, 63.9, 61.7, 55.0, 48.0, 45.4, 43.2, 42.6, 41.0, 38.8, 38.0, 37.3, 36.9, 32.6, 31.8, 31.1, 29.2, 28.4, 28.0, 26.4, 26.3, 23.5, 23.3, 21.3, 18.6, 17.3, 16.6, 16.3

Example 16

Compound 16

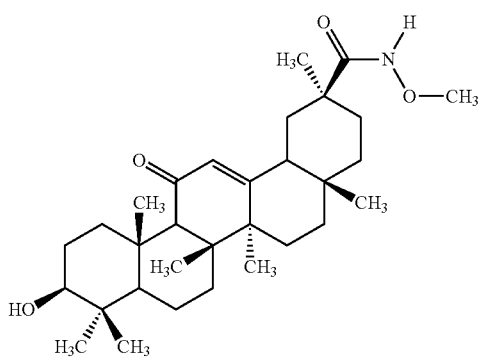

(3S,18R,20S)-3-Hydroxy-N-methoxy-11-oxo-olean-12-en-29-amide (3S,18R,20S)-3-(Acetyloxy)-N-methoxy-11-oxo-olean-12-en-29-amide was hydrolyzed to (3S,18R,20S)-3-hydroxy-N-methoxy-11-oxo-olean-12-en-29-amide according to the general procedure for deprotection of 3-acetylated hydroxamic acids $^1$H NMR (200 MHz, CDCl$_3$): δ 9.33 (br, 1H), 5.67 and 5.29 (2s, 1H), 3.73 (s, 3H), 3.20 (m, 1H), 2.74 (d, 1H), 2.40-0.60 (m, 21H), 1.34 (s, 3H), 1.14 (s, 3H), 1.10 (s, 6H), 0.98 (s, 3H), 0.80 (s, 3H), 0.78 (s, 3H)

$^{13}$C NMR (50 MHz, CDCl$_3$): δ 200.4, 173.6, 169.6, 128.4, 78.8, 64.0, 61.8, 55.0, 48.1, 45.4, 43.2, 42.5, 41.1, 39.2, 39.1, 37.3, 37.1, 32.7, 31.8, 31.1, 29.2, 28.5, 28.1, 27.2, 26.4 (2C), 23.3, 18.6, 17.4, 16.3, 15.6

Example 17

Compound 17

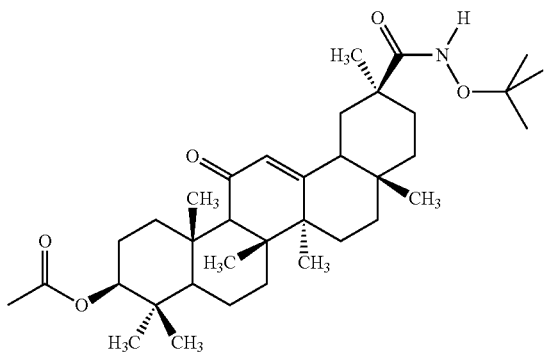

(3S,18R,20S)-3-(Acetyloxy)-N-(1,1-dimethylethoxy)-11-oxo-olean-12-en-29-amide (3S,18R,20S)-3-(Acetyloxy)-11-oxo-olean-12-en-29-oic acid was reacted with O-(1,1-dimethylethyl)-hydroxylamine hydrochloride to (3S,18R,20S)-3-(acetyloxy)-N-(1,1-dimethylethoxy)-11-oxo-olean-12-en-29-amide according to the general synthetic procedure for the preparation of the hydroxamic acids.

$^1$H NMR (200 MHz, CDCl$_3$): δ 9.08 (s, 1H), 5.69 and 5.24 (s, 1H), 4.42 (dd, 1H), 2.70 (m, 1H), 2.35-0.70 (m, 20H), 1.98 (s, 3H), 1.30 (s, 3H), 1.19 (s, 9H), 1.10 (s, 3H), 1.08 (s, 3H), 1.07 (s, 3H), 0.80 (s, 6H), 0.77 (s, 3H)

$^{13}$C NMR (50 MHz, CDCl$_3$): δ 200.3, 174.9, 171.0, 170.0, 128.4, 81.5, 80.5, 61.6, 54.9, 48.3, 45.4, 43.4, 43.3, 40.7, 38.8, 37.9, 37.5, 36.9, 32.6, 31.7, 31.5, 29.1, 28.6, 28.0, 26.7 (3C), 26.4, 26.3, 23.4, 23.2, 21.2, 18.5, 17.3, 16.6, 16.3

Example 18

Compound 18

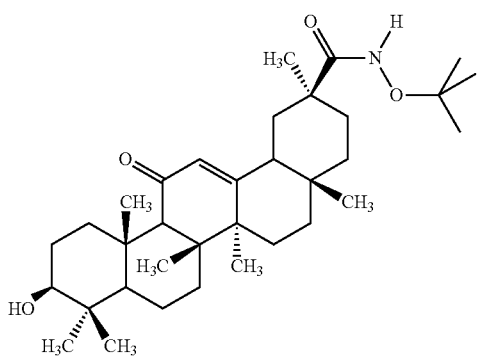

(3S,18R,20S)-3-Hydroxy-N-(1,1-dimethylethoxy)-11-oxo-olean-12-en-29-amide (3S,18R,20S)-3-Acetyloxy-N-(1,1-dimethylethoxy)-11-oxo-olean-12-en-29-amide was hydrolyzed to (3S,18R,20S)-3-hydroxy-N-(1,1-dimethylethoxy)-11-oxo-olean-12-en-29-amide according to the general procedure for deprotection of 3-acetylated hydroxamic acids $^1$H NMR (200 MHz, CDCl$_3$): δ 8.57 (br, 1H), 5.70 and 5.29 (2s, 1H), 3.20 (m, 1H), 2.74 (m, 1H), 2.38-0.60 (m, 21H), 1.35 (s, 3H), 1.25 (s, 9H), 1.15 (s, 3H), 1.11 (s, 6H), 0.98 (s, 3H), 0.81 (s, 3H), 0.78 (s, 3H)

$^{13}$C NMR (50 MHz, CDCl$_3$): δ 200.4, 174.4, 169.6, 128.5, 81.7, 78.8, 61.8, 55.0, 48.2, 45.4, 43.3 (2C), 41.1, 39.2, 39.1, 37.5, 37.1, 32.8, 31.8, 31.4, 29.3, 28.6, 28.1, 27.2, 26.7 (3C), 26.4 (2C), 23.3, 18.6, 17.4, 16.3, 15.5

Example 19

Compound 19

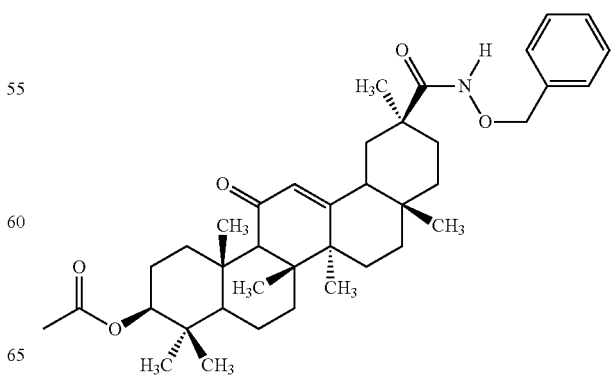

(3S,18R,20S)-3-(Acetyloxy)-N-(benzyloxy)-11-oxo-olean-12-en-29-amide (3S,18R,20S)-3-(Acetyloxy)-11-oxo-olean-12-en-29-oic acid was reacted with O-benzyl-hydroxylamine hydrochloride to (3S,18R,20S)-3-(acetyloxy)-N-(benzyloxy)-11-oxo-olean-12-en-29-amide according to the general synthetic procedure for the preparation of the hydroxamic acids.

$^1$H NMR (200 MHz, CDCl$_3$): δ 9.45 (s, 1H), 7.36-7.26 (m, 5H), 5.43 and 5.25 (s, 1H), 4.89 (s, 2H), 4.45 (dd, 1H), 2.70 (m, 1H), 2.30-0.70 (m, 20H), 1.99 (s, 3H), 1.27 (s, 3H), 1.10 (s, 3H), 1.08 (s, 3H), 1.07 (s, 3H), 0.83 (s, 6H), 0.75 (s, 3H)

$^{13}$C NMR (50 MHz, CDCl$_3$): δ 200.2, 173.5, 171.0, 169.4, 135.5, 129.1 (2C), 128.7, 128.5 (2C), 128.4, 80.6, 77.8, 61.6, 54.9, 47.8, 45.4, 43.1, 42.9, 40.7, 38.8, 38.0, 37.4, 36.8, 32.6, 31.7, 31.2, 29.2, 28.4, 28.0, 26.3 (2C), 23.4, 23.3, 21.3, 18.6, 17.3, 16.6, 16.4

Example 20

Compound 20

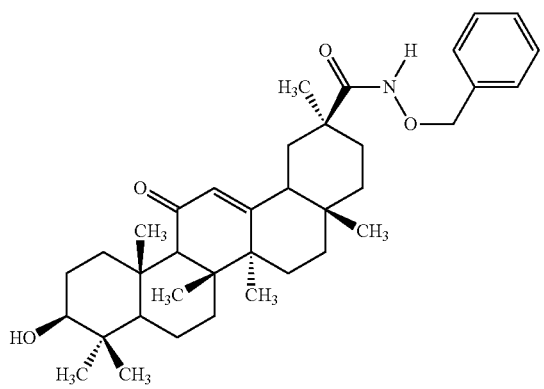

(3S,18R,20S)-3-Hydroxy-N-(benzyloxy)-11-oxo-olean-12-en-29-amide (3S,18R,20S)-3-Acetyloxy-N-(benzyloxy)-11-oxo-olean-12-en-29-amide was hydrolyzed to (3S,18R,20S)-3-hydroxy-N-(benzyloxy)-11-oxo-olean-12-en-29-amide according to the general procedure for deprotection of 3-acetylated hydroxamic acids $^1$H NMR (200 MHz, CDCl$_3$): δ 8.98 (m, 1H), 7.37 (m, 5H), 5.44 and 5.29 (2s, 1H), 4.92 (s, 2H), 3.15 (m, 1H), 2.72 (m, 1H), 2.30-0.59 (m, 21H), 1.31 (s, 3H), 1.11 (s, 9H), 0.96 (s, 3H), 0.78 (s, 3H), 0.76 (s, 3H)

$^{13}$C NMR (50 MHz, CDCl$_3$): δ 200.1, 175.2, 169.1, 135.6, 128.8 (5C), 128.6, 78.8, 77.7, 61.8, 55.0, 47.9, 45.4, 43.1, 42.8, 40.9, 39.4, 39.1, 37.3, 37.0, 32.7, 31.8, 31.1, 29.4, 28.3, 28.1, 27.1, 26.4, 26.3, 23.3, 18.6, 17.4, 16.3, 15.5

Example 21

Compound 21

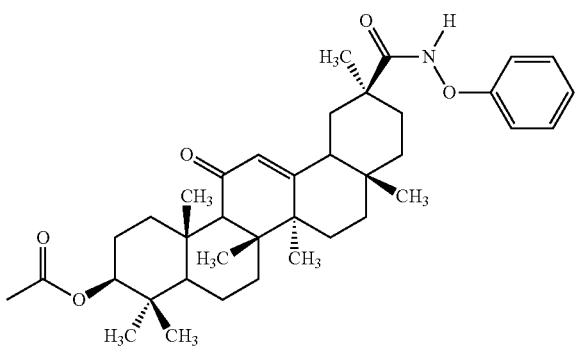

(3S,18R,20S)-3-(Acetyloxy)-N-phenoxy-11-oxo-olean-12-en-29-amide (3S,18R,20S)-3-(Acetyloxy)-11-oxo-olean-12-en-29-oic acid was reacted with O-phenyl-hydroxylamine hydrochloride to (3S,18R,20S)-3-(acetyloxy)-N-(phenoxy)-11-oxo-olean-12-en-29-amide according to the general synthetic procedure for the preparation of the hydroxamic acids.

$^1$H NMR (200 MHz, CDCl$_3$): δ 10.18 (s, 1H), 7.29-6.94 (m, 5H), 5.64 and 5.29 (s, 1H), 4.47 (dd, 1H), 2.78 (m, 1H), 2.36-0.75 (m, 20H), 2.02 (s, 3H), 1.33 (s, 3H), 1.25 (s, 3H), 1.10 (s, 3H), 1.00 (s, 3H), 0.85 (s, 6H), 0.77 (s, 3H)

$^{13}$C NMR (50 MHz, CDCl$_3$): δ 200.6, 174.6, 171.1, 170.0, 159.7, 129.4 (2C), 128.3, 122.7, 113.2 (2C), 80.6, 61.7, 55.0, 48.2, 45.4, 43.2, 41.0, 38.9, 38.0 (2C), 37.4, 36.9, 32.6, 31.8, 31.2, 29.1, 28.5, 28.0, 26.4 (2C), 23.5, 23.3, 21.3, 18.5, 17.3, 16.6, 16.4

Example 22

Compound 22

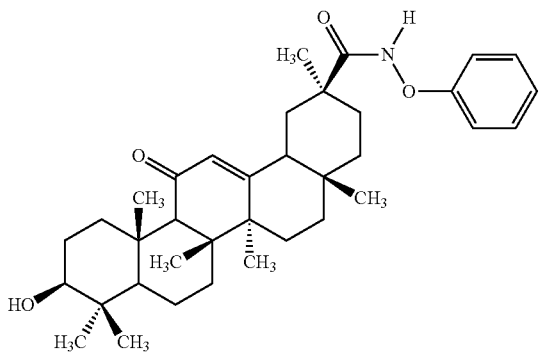

(3S,18R,20S)-3-Hydroxy-N-phenoxy-11-oxo-olean-12-en-29-amide (3S,18R,20S)-3-Acetyloxy-N-(phenoxy)-11-oxo-olean-12-en-29-amide was hydrolyzed to (3S,18R,20S)-3-hydroxy-N-(phenoxy)-11-oxo-olean-12-en-29-amide according to the general procedure for deprotection of 3-acetylated hydroxamic acids $^1$H NMR (200 MHz, Pyridine-d$_5$): δ 7.35 (m, 4H), 6.99 (m, 1H), 5.97 and 5.65 (2s, 1H), 3.58-0.75 (m, 24H), 1.39 (s, 3H), 1.30 (s, 3H), 1.24 (s, 3H), 1.10 (s, 3H), 1.06 (s, 6H), 0.82 (s, 3H)

$^{13}$C NMR (50 MHz, Pyridine-d$_5$): δ 200.0, 174.8, 169.0, 159.7, 130.4 (2C), 129.3, 123.2, 114.3 (2C), 78.4, 62.7, 55.8, 49.0, 46.0, 45.3, 44.0, 42.2, 40.3 (2C), 38.6, 38.1, 33.5, 32.6, 31.7, 29.7, 29.2 (2C), 28.6, 27.3 (2C), 23.9, 19.3, 18.4, 17.3, 17.0

Example 23

Compound 23

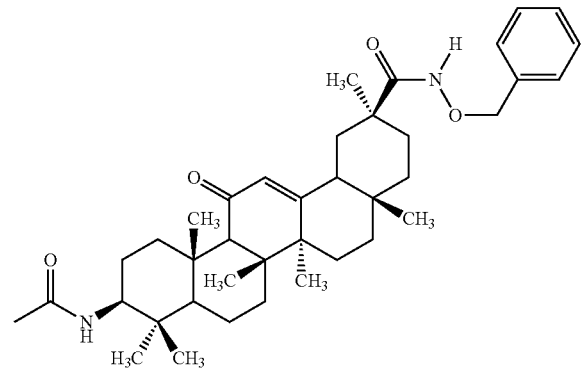

(3S,18R,20S)-3-(Acetamino)-N-benzyloxy-11-oxo-olean-12-en-29-amide

PCC (10.83 g, 50.26 mmol, 1.5 equiv) was added to a stirred solution of (3S, 18R, 20S)-3-hydroxy-11-oxo-olean-12-en-29-oic acid, diphenylmethylester in DCM (600 mL) and the reaction mixture was stirred at reflux under TLC monitoring (Hex:EtOAc 3:1). Upon complete conversion (2.5 h) the reaction mixture was cooled to RT within 30 min and was filtered through a bed of dry silica gel (350 g). Fractioned elution with Et$_2$O (500 mL) and evaporation of appropriate fractions gave (18R,20S)-3,11-dioxo-olean-12-en-29-oic acid, diphenylmethyl ester as white solid foam in a yield of 21.1 g (99.3%) after drying in vacuo. An analytical sample was prepared by recrystallization from Et$_2$O.

Optical rotation: [α]$_D^{20}$=+142.0 (c=1.0 in CHCl$_3$)
m.p.=172-174° C. (Et$_2$O)
Rf-value=0.35 (Hex:EtOAc 3:1)

$^1$H-NMR (CDCl$_3$): δ 0.68 (s, 3H, H28), 0.95-1.04 (m, 1H, H15$_b$), 1.07 (s, 3H, H23/24), 1.10 (s, 3H, H23/24), 1.13 (s, 3H, H26), 1.15-1.24 (m, 4H, H16$_b$), 1.17 (s, 3H, H29), 1.24-1.38 (m, 4H, H5, H21$_b$, H22$_b$, H22$_a$), 1.27 (s, 3H, H25), 1.37 (s, 3H, H27), 1.40-1.49 (m, 2H, H1$_b$, H6$_b$), 1.49-1.60 (m, 2H, H7$_b$, H7$_a$), 1.60-1.75 (m, 2H, H6$_a$, H19$_b$), 1.74-1.89 (td, 1H, H15$_a$), 1.94-2.13 (m, 4H, H16$_a$, H18, H19$_a$, H21$_a$), 2.30-2.41 (m, 1H, H2$_b$), 2.42 (s, 1H, H9), 2.56-2.70 (m, 1H, H2$_a$), 2.91-3.02 (m, 1H, H1$_a$), 5.55 (s, 1H, H12), 6.93 (s, 1H, Dpm O—CH-Ph$_2$), 7.24-7.42 (m, 10H, Dpm)

$^{13}$C-NMR (CDCl$_3$): δ 15.6 (q, C25), 18.5 (q, C26), 18.8 (t, C7), 21.4 (q, C27), 23.3 (q, C23/24), 26.36 (t, C15/16), 26.39 (q, C23/24), 26.5 (t, C15/16), 28.2 (q, C29), 28.3 (q, C28), 31.2 (t, C21), 31.8 (s, C17), 32.1 (t, C6), 34.2 (t, C2), 36.7 (s, C10), 37.5 (t, C22), 39.8 (t, C1), 41.2 (t, C19), 43.3 (s, C20), 44.0 (s, C8), 45.2 (s, C14), 47.8 (s, C4), 48.1 (d, C18), 55.4 (d, C5), 61.0 (d, C9), 76.6 (d, Dpm O—CH-Ph$_2$), 127.0 (2×d, Dpm), 127.3 (2×d, Dpm), 127.8 (d, Dpm), 128.1 (d, Dpm), 128.41 (d, C12), 128.46 (2×d, Dpm), 128.6 (2×d, Dpm), 140.06 (s, Dpm), 140.12 (s, Dpm), 169.3 (s, C13), 175.1 (s, C30), 199.3 (s, C11), 217.1 (s, C3)

A solution of (18R,20S)-3,11-dioxo-olean-12-en-29-oic acid, diphenylmethyl ester (21.12 g, 33.27 mmol, 1.0 equiv) and hydroxylamine-hydrochloride (12.25 g, 176.34 mmol, 5.3 equiv) in dry pyridine (160 mL) was stirred for 2 h at 50° C. under TLC (Hex:EtOAc 3:1) monitoring. Upon complete conversion (2 h) the reaction mixture was allowed to cool to RT, was diluted with DCM (500 mL) and washed with 2N HCl (4× á 370 mL), with NaHCO$_3$ and with brine, dried over Na$_2$SO$_4$ and was evaporated to give (18R,20S)-3-(hydroxyimino)-11-oxo-olean-12-en-29-oic acid, diphenylmethyl ester as white solid in a yield of 19.016 g (87.9%) after grinding and drying in vacuo.

Optical rotation: [α]$_D^{20}$=+85.2 (c=1.0 in CHCl$_3$)
Rf-value: 0.24 (Hex:EtOAc 3:1)

$^1$H-NMR (CDCl$_3$): δ 0.67 (s, 3H, H28), 0.93-1.07 (m, 2H, H5, H15$_b$), 1.07-1.14 (m, 1H, H1$_b$), 1.08 (s, 3H, H23/24), 1.12 (s, 3H, H26), 1.14-1.22 (m, 1H, H16$_b$), 1.17 (2×s, 6H, H23/24, H29), 1.22-1.42 (m, 3H, H21$_b$, H22$_b$, H22$_a$), 1.25 (s, 3H, H25), 1.34 (s, 3H, H27), 1.38-1.57 (m, 2H, H6$_b$, H7$_b$), 1.57-1.73 (m, 3H, H6$_a$, H7$_a$, H19$_b$), 1.73-1.89 (td, 1H, H15$_a$), 1.93-2.14 (m, 4H, H16$_a$, H18, H19$_a$, H21$_a$), 2.20-2.34 (m, 1H, H2$_b$), 2.36 (s, 1H, H9), 2.82-2.94 (m, 1H, H1$_a$), 3.00-3.13 (m, 1H, H2$_a$), 5.53 (s, 1H, C12), 6.93 (s, 1H, Dpm O—CH-Ph$_2$), 7.23-7.43 (m, 10H, Dpm)

$^{13}$C-NMR (CDCl$_3$): δ 15.7 (q, C25), 17.1 (t, C2), 18.2 (t, C7), 18.6 (q, C26), 23.24 (q, C27), 23.27 (q, C23/24), 26.36 (t, C16), 26.43 (t, C15), 27.1 (q, C23/24), 28.2 (q, C29), 28.3 (q, C28), 31.2 (t, C21), 31.7 (s, C17), 32.4 (t, C6), 37.0 (s, C10), 37.5 (t, C22), 39.1 (t, C1), 40.4 (s, C4), 41.1 (t, C19), 43.2 (s, C20), 44.0 (s, C8), 45.3 (s, C14), 48.1 (d, C18), 55.6 (d, C5), 61.3 (d, C9), 76.6 (d, Dpm O—CH-Ph$_2$), 127.0 (2×d, Dpm), 127.3 (2×d, Dpm), 127.8 (d, Dpm), 128.1 (d, Dpm), 128.4 (3×d, C12, 2×Dpm), 128.6 (2×d, Dpm), 140.06 (s, Dpm), 140.12 (s, Dpm), 166.9 (s, C3), 169.0 (s, C13), 175.2 (s, C30), 199.6 (s, C11)

NaOAc (8.23 g, 100.3 mmol, 16.3 equiv) was added portion wise to a TiCl$_3$ solution ((12% in 5-10% HCl, 31.63 g, 24.6 mmol, 4.0 equiv) and was stirred until a clear solution was obtained. This solution was bubbled with argon for several minutes before it was added dropwise within 15 min under an atmosphere of argon to a suspension of (18R,20S)-3-(hydroxyimino)-11-oxo-olean-12-en-29-oic acid diphenylmethyl ester (4.0 g, 6.16 mmol, 1.0 equiv) and BH$_3$.tBNH$_2$ ((1.34 g, 15.39 mmol, 2.5 equiv) in EtOH (150 mL) at –9° C. (ice/EtOH), which had been bubbled with argon for approximately 30 min under mechanical stirring. After 4 h the reaction mixture was allowed to come to RT and was stirred at RT overnight. The reaction mixture was diluted with DCM, NH$_4$Cl was added and the phases were shaken and separated. The aqueous layer was extracted with DCM and the combined organic layers were washed with NH$_4$Cl, NaHCO$_3$, water and brine.

After drying over Na$_2$SO$_4$ the mixture was evaporated to give crude material which had to be purified by column chromatography (SiO$_2$; 680 g, CHCl$_3$:MeOH 8:1+0.1% AcOH to CHCl$_3$:MeOH 4:1+0.1% AcOH. All amine containing fractions were pooled and treated with saturated NaHCO$_3$, brine, drying over Na$_2$SO$_4$ and evaporation to give pure n-amine (3S,18R,20S)-3-(amino)-11-oxo-olean-12-en-29-oic acid, diphenylmethyl ester (2.32 g, 59.3%) as white solid foam.

Optical rotation: $[\alpha]_D^{20}$=+129.8 (c=1.0, CHCl$_3$)

Rf-value=0.23 (CHCl$_3$:MeOH 9:1+0.1% AcOH)

$^1$H-NMR (CDCl$_3$): δ 0.66 (s, 3H, H28), 0.69-0.77 (m, 2H, H5, H16$_b$), 0.84 (s, 3H, H23/24), 0.91-1.07 (m, 3H, H1$_b$, H7$_b$, H16$_a$), 1.04 (s, 3H, H23/24), 1.09 (s, 3H, H26), 1.13 (s, 3H, H25), 1.17 (s, 3H, H29), 1.22-1.53 (m, 4H, H6$_b$, H21$_b$, H22$_b$, H22$_a$), 1.36 (s, 3H, H27), 1.55-1.73 (m, 5H, H2$_b$, H2$_a$, H6$_a$, H7$_a$, C19$_b$), 1.73-1.87 (td, 1H, H15$_b$), 1.92-2.10 (m, 4H, H15$_a$, H18, H19$_a$, H21$_a$), 2.33 (s, 1H, H9), 2.50-2.59 (m, 1H, H3), 2.75-2.86 (m, 1H, H1$_a$), 5.51 (s, 1H, H12), 6.93 (s, 1H, Dpm O—CH-Ph$_2$), 7.22-7.42 (m, 10H, Dpm)

$^{13}$C-NMR (CDCl$_3$): δ 16.05 (q, C25), 16.13 (q, C23/24), 17.7 (t, C7), 18.7 (q, C26), 23.3 (q, C27), 26.4 (3×t, C2, C15, C16), 28.2 (2×q, C28, C29), 28.5 (q, C23/C24), 31.2 (t, C21), 31.7 (s, C17), 32.7 (t, C6), 37.2 (s, C10), 37.5 (t, C22), 38.0 (s, C4), 39.6 (t, C1), 41.1 (t, C19), 43.2 (s, C20), 44.0 (s, C8), 45.2 (s, C14), 48.0 (d, C18), 55.4 (d, C5), 60.0 (d, C3), 61.7 (d, C9), 76.6 (d, Dpm O—CH-Ph2), 127.0 (2×d, Dpm), 127.3 (2×d, Dpm), 127.8 (d, Dpm), 128.1 (d, Dpm), 128.4 (2×d, Dpm), 128.5 (d, C12), 128.6 (2×d, Dpm), 140.07 (s, Dpm), 140.11 (s, Dpm), 168.7 (s, C13), 175.2 (s, C30), 199.9 (s, C11)

To a solution of (3S,18R,20S)-3-(amino)-11-oxo-olean-12-en-29-oic acid, diphenylmethyl ester (440 mg, 0.692 mmol, 1.0 equiv) in dry DCM (10 mL) TEA (0.49 g, 4.8 mmol, 7.0 equiv) followed by acetic anhydride (350 mg, 3.46 mmol, 5.0 equiv) were added at 0° C. The reaction mixture was stirred at 0° C. monitored by TLC (Hex:EtOAc 1:2, CHCl$_3$:MeOH 9:1+AcOH). After 1 h the reaction mixture was diluted with EtOAc, washed with diluted HCl twice, with NaHCO$_3$ and brine, dried over Na$_2$SO$_4$ and evaporated to give crude material as white solid which was recrystallized from DCM/EtOAc to give white crystals (395 mg, 84.2%), pure (3S,18R,20S)-3-(acetamino)-11-oxo-olean-12-en-29-oic acid, diphenylmethyl ester.

Optical rotation: $[\alpha]_D^{20}$=+101.2 (c=1.0 in CHCl$_3$)

m.p.=162-165° C. (EtOAc/DCM)

Rf-value=0.22 (Hex:EtOAc 1:2)

$^1$H-NMR (CDCl$_3$): δ 0.66 (s, 3H, H28), 0.79 (s, 3H, H23/24), 0.81-0.93 (m, 1H, H5), 0.91 (s, 3H, H23/24), 0.93-1.07 (m, 2H, H7$_b$, H16$_b$), 1.09 (s, 3H, H26), 1.10-1.16 (m, 1H, H1$_b$), 1.13 (s, 3H, H25), 1.17 (s, 3H, H29), 1.22-1.27 (1H, H16$_a$), 1.27-1.34 (m, 3H, H21$_b$, H22$_b$, H22$_a$), 1.36 (s, 3H, H27), 1.38-1.45 (m, 1H, H6$_b$), 1.45-1.56 (2H, H2$_b$, H2$_a$), 1.56-1.60 (m, 1H, H7$_a$), 1.60-1.69 (m, 2H, H6$_a$, H19$_b$), 1.69-1.85 (1H, H15$_b$), 1.63-2.10 (m, 4H, H15$_a$, H18, H19$_a$, H21$_a$), 2.00 (s, 3H, Ac—CH$_3$), 2.36 (d, 1H, H9) 2.73-2.82 (m, 1H, H1$_a$), 3.65-3.77 (1H, H3), 5.50 (s, 1H, H12), 6.93 (s, 1H, Dpm O—CH-Ph$_2$), 7.22-7.42 (m, 10H, Dpm)

$^{13}$C-NMR (CDCl$_3$): δ 16.2 (q, C25), 16.6 (q, C23/24), 17.7 (t, C7), 18.6 (q, C26), 23.2 (q, C27), 23.7 (q, Ac—CH$_3$), 25.4 (t, C2), 26.4 (t, C16), 26.4 (t, C15), 28.2 (q, C29), 28.3 (q, C28), 28.4 (q, C23/24), 31.1 (t, C21), 31.7 (s, C17), 32.7 (t, C6), 36.9 (s, C10), 37.5 (t, C22), 38.0 (s, C4), 39.7 (t, C1), 41.1 (t, C19), 43.2 (s, C20), 44.0 (s, C8), 45.3 (s, C14), 48.1 (d, C18), 55.4 (d, C5), 56.4 (d, C3), 61.7 (d, C9), 76.6 (d, Dpm O—CH-Ph2), 126.9 (2×d, Dpm), 127.2 (2×d, Dpm), 127.8 (d, Dpm), 128.1 (d, Dpm), 128.2 (d, C12), 128.4 (2×d, Dpm), 128.6 (2×d, Dpm), 140.07 (s, Dpm), 140.13 (s, Dpm), 168.9 (s, Ac—CO), 169.6 (s, C13), 175.2 (s, C30), 200.0 (s, C11)

(3S,18R,20S)-3-(Acetamino)-11-oxo-olean-12-en-29-oic acid, diphenylmethyl ester (250 mg, 0.37 mmol, 1.0 equiv) was dissolved in MeOH:EtOAc:AcOH 50:50:1 (10 mL) The atmosphere was exchanged to argon, before Pd/C (25 mg, 10%) was added. The atmosphere was exchanged to H$_2$ and the reaction was stirred at RT monitored by TLC (Hex:EtOAc 1:2). Upon complete conversion the reaction atmosphere was exchanged to argon, the reaction mixture was filtered through an hydrophobic filter and washed with MeOH:EtOAc 1:1. The solvents were evaporated and the crude material was purified by column chromatography (SiO$_2$: 10 g, 50 mL Hex: EtOAc 5:1 to Hex:MeOH 5:1) to give pure (3S,18R,20S)-3-(acetamino)-11-oxo-olean-12-en-29-oic acid (0.136 g, 72.1%).

Optical rotation: $[\alpha]_D^{20}$=+113.0 (c=1.0 in CHCl$_3$:MeOH 3:1)

Rf-value=0.48 (Hex:EtOAc 1:5)

1H-NMR (CDCl$_3$): δ 0.82 (s, 3H, H25), 0.83 (s, 3H, H28), 0.85-0.94 (m, 1H, H5), 0.89 (s, 3H, H23/24), 0.99-1.17 (m, 2H, H1b, H16$_b$), 1.14 (2×s, 6H, H23/24, H26), 1.17-1.28 (m, 1H, H15$_b$), 1.20 (s, 3H, H29), 1.30-1.54 (m, 6H, H2$_b$, H6$_b$, H7$_b$, H21$_b$, H22$_a$, H22$_b$), 1.41 (s, 3H, H27), 1.55-1.74 (m, 4H, H2$_a$, H6$_a$, H7$_a$, H19$_b$), 1.79-2.15 (m, 4H, H15$_a$, H16$_a$, H19$_a$, H21$_a$); 1.99 (s, 3H, Ac—CH3), 2.15-2.26 (m, 1H, H18), 2.44 (s, 1H, H9), 2.69-2.80 (m, 1H, H1$_a$), 3.58-3.70 (m, 1H, H3), 5.65 (s, 1H, H12)

13C-NMR (CDCl3): δ 15.8 (q, C23/24), 16.0 (q, C25), 17.3 (t, C7), 18.2 (q, C26), 22.3 (q, Ac—CH3), 22.8 (q, C27), 24.6 (t, C2), 26.0 (2×t, C15, C16), 27.9-28.1 (3×q, C23/24, C28, C29), 30.6 (t, C21), 31.5 (s, C17), 32.2 (t, C6), 36.6 (s, C10), 37.3 (t, C22), 37.9 (s, C4), 39.4 (t, C1), 40.7 (t, C19), 43.0 (s, C20), 43.3 (s, C8), 45.1 (s, C14), 48.6 (d, C18), 55.0 (d, C5), 56.3 (d, C3), 61.4 (d, C9), 127.6 (d, C12), 170.8 (2×s, Ac—CO, C13), 179.0 (s, C30), 201.0 (s, C11)

(3S,18R,20S)-3-(Acetamino)-11-oxo-olean-12-en-29-oic acid (200 mg, 0.39 mmol, 1.0 equiv) was stirred in a mixture of SOCl$_2$ (5.7 mL, 78.2 mmol, 200 equiv) and toluene (5.7 mL) overnight. Upon complete conversion according to TLC (SiO$_2$, DCM:MeOH 8:1) the excess SOCl$_2$ was evaporated and the residue was coevaporated from toluene twice. A solution of NH$_2$OBn (58 mg 0.47 mmol, 1.2 equiv) and TEA (108 μL, 0.78 mmol, 2.0 equiv) in acetonitrile was stirred at 0° C. for 30 min, before it was added in one portion to a solution of acid chloride in acetonitrile (2 mL). The reaction mixture was stirred at RT monitored by TLC (SiO$_2$:DCM:Et$_2$O 1:1). After 1.5 h complete conversion was observed and solvents were evaporated, the residue was taken up in DCM and washed with water, NaHCO$_3$ and brine, dried over Na$_2$SO$_4$ and evaporated. The crude material was purified by flash column chromatography (SiO$_2$: 25 g, 150 mL DCM:Et$_2$O 5:1, 450 mL, DCM:MeOH 20:1, fractions á 25 mL) to give pure (3S, 18R,20S)-3-(acetamino)-N-benzyloxy-11-oxo-olean-12-en-29-amide (0.224 g, 92.9%).

Optical rotation: $[\alpha]_D^{20}$=+108.9 (c=1.0 in CHCl$_3$:MeOH 3:1)

Rf-value=0.45 (DCM:MeOH 5:1)

$^1$H-NMR (CDCl$_3$): δ 0.70 (s, 3H, H28), 0.72 (s, 3H, C23/24), 0.73-0.79 (m, 1H, H5), 0.81 (s, 3H, H23/24), 0.86-0.99 (m, 2H, H16b, H1b), 1.04 (s, 6H, H26, H29), 1.05 (s, 3H, H25), 1.07-1.14 (m, 1H, H15b), 1.14-1.39 (m, 6H, H6b, H7b, H16a, H21b, H22a, H22b), 1.26 (s, 3H, H27), 1.39-1.60 (m, 5H, H2a, H2b, H6a, H7a, H19b), 1.63-1.79 (m, 2H, H15a, H19a), 1.83-1.93 (m, 1H, H21a), 1.94 (s, 3H, Ac—CH3), 1.97-2.06 (m, 1H, H18), 2.26 (s, 1H, H9), 2.63-2.73 (m, 1H, H1a), 2.64-2.74 (m, 1H, H3), 4.89 (s, 2H, CH$_2$-Ph), 5.43 (s, 1H, H12), 7.24-7.38 (m, 5H, Aromat), 8.83 (s, 1H, NH)

$^{13}$C-NMR (CDCl$_3$): δ 16.2 (q, C25), 16.6 (q, C23/24), 17.6 (t, C7), 18.6 (q, C26), 23.3 (q, C27), 23.4 (q, Ac—CH3), 25.3 (t, C2), 26.3 (2×t, C15, C16), 28.3 (q, C28), 28.6 (q, C23/24), 29.4 (q, C29), 31.2 (t, C21), 31.7 (s, C17), 32.6 (t, C6), 36.9 (s, C10), 37.3 (t, C22), 38.1 (s, C4), 39.8 (t, C1), 40.8 (t, C19), 42.8 (s, C20), 43.1 (s, C8), 45.3 (s, C14), 47.7 (d, C18), 55.5 (d, C5), 56.7 (d, C3), 61.7 (d, C9), 77.7 (t, CH$_2$-Ph), 128.5 (d, C12), 128.6 (2×d, Ar—C3, Ar—C5), 128.8 (d, Ar—C4), 129.2 (d, Ar—C2, Ar—C6), 135.4 (s, Ar—C1), 169.0 (s, C13), 170.0 (s, Ac—CO), 173.5 (s, C30), 200.0 (s, C11)

Example 24

Compound 24

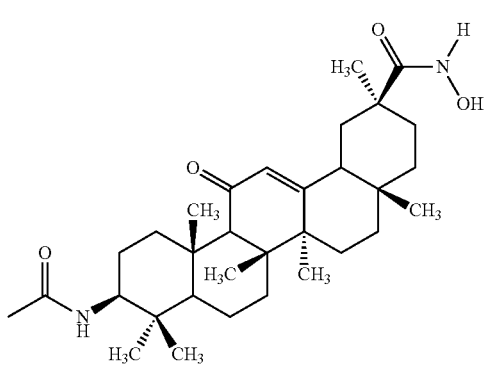

(3S,18R,20S)-3-(Acetamino)-N-hydroxy-11-oxo-olean-12-en-29-amide (3S,18R,20S)-3-(Acetamino)-N-benzyloxy-11-oxo-olean-12-en-29-amide (90 mg, 0.15 mmol, 1.0 equiv) was dissolved in THF (2 mL). The atmosphere was exchanged to argon, before Pd/C (18 mg, 20%) was added. The atmosphere was exchanged to $H_2$ and the reaction was stirred at RT, monitored by TLC (DCM:MeOH 5:1). Upon complete conversion the reaction atmosphere was exchanged to argon, the reaction mixture was filtered over Celite® and washed with THF. Solvents were removed in vacuo and the residue was purified by flash column chromatography (SiO$_2$: 6 g, 40 mL DCM:MeOH 20:1, 70 mL DCM:MeOH 10:1, fractions a 6 mL). Target compound containing fractions were pooled and washed with NaHCO$_3$ and brine, dried over Na$_2$SO$_4$ and evaporated and dried to give to give pure (3S,18R,20S)-3-(acetamino)-N-hydroxy-11-oxo-olean-12-en-29-amide (0.037 g, 47.5%).

Optical rotation: $[\alpha]_D^{20}$=+112.1 (c=1.0 in CHCl$_3$:MeOH 3:1)

Rf-value=0.37 (DCM:MeOH 5:1)

$^1$H-NMR (CDCl$_3$): δ 0.67-0.77 (m, 1H, H5), 0.72 (s, 3H, H23/24), 0.75 (s, 3H, H23/24), 0.81 (s, 3H, H23/24), 0.82-0.92 (m, 1H, H1b), 0.92-0.99 (m, 1H, H16b), 1.03 (s, 3H, H26), 1.04 (s, 3H, H25), 1.05-1.17 (m, 1H, H15b), 1.08 (s, 3H, H29), 1.16-1.41 (m, 5H, H6b, H7b, H21b, H22a, H22b), 1.31 (s, 3H, H27), 1.41-1.68 (m, 5H, H2a, H2b, H6a, H7a, H19b), 1.68-1.81 (m, 1H, H15a), 1.86-2.10 (m, 3H, H16a, H19a, H21a), 2.00 (s, 3H, Ac—CH3), 2.12-2.23 (m, 1H, H18), 2.28 (s, 1H, H9), 2.64-2.74 (m, 1H, H1a), 3.50-3.61 (m, 1H, H3), 5.76 (s, 1H, H12), 10.37 (s, 1H, NH)

$^{13}$C-NMR (CDCl$_3$): δ 16.2 (q, C25), 16.6 (q, C23/24); 17.7 (t, C7); 18.6 (q, C26); 23.5 (2xs, C27, Ac CH3), 25.3 (t, C2), 26.4 (2xt, C15, C16), 28.4 (q, C28), 28.7 (q, C23/24), 29.4 (q, C29), 31.1 (t, C21), 31.7 (t, C17), 32.7 (t, C6), 37.0 (s, C10), 37.4 (t, C22), 38.2 (s, C4), 40.2 (2xt, C1, C19), 42.3 (s, C20), 43.2 (s, C8), 45.4 (s, C14), 47.6 (d, C18), 55.8 (d, C5), 56.8 (d, C3), 61.8 (d, C9), 129.1 (d, C12), 168.9 (s, C13), 169.8 (s, C13), 173.2 (s, C30), 200.1 (s, C11)

Example 25

Compound 25

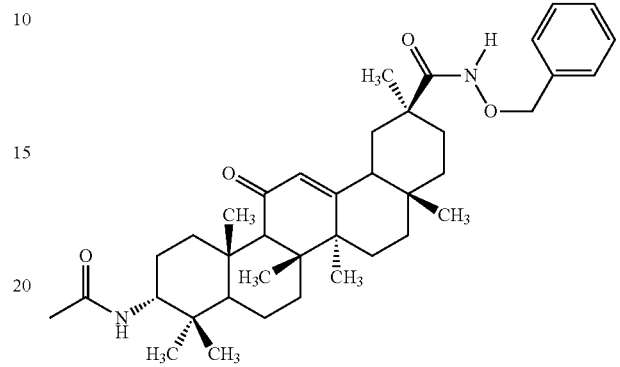

(3R,18R,20S)-3-(Acetamino)-N-benzyloxy-11-oxo-olean-12-en-29-amide

NaOAc (8.23 g, 100.3 mmol, 16.3 equiv) was added portion wise to a TiCl$_3$ solution ((12% in 5-10% HCl, 31.63 g, 24.6 mmol, 4.0 equiv) and was stirred until a clear solution was obtained. This solution was bubbled with argon for several minutes before it was added dropwise within 15 min under an atmosphere of argon to a suspension of (18R,20S)-3-(hydroxyimino)-11-oxo-olean-12-en-29-oic acid diphenylmethyl ester (4.0 g, 6.16 mmol, 1.0 equiv) and BH$_3$.tBNH$_2$ ((1.34 g, 15.39 mmol, 2.50 equiv) in EtOH (150 mL) at −9° C. (ice/EtOH), which had been bubbled with argon for approximately 30 min under mechanical stirring. After 4 h the reaction mixture was allowed to come to RT and was stirred at RT overnight. The reaction mixture was diluted with DCM, NH$_4$Cl was added and the phases were shaken and separated. The aqueous layer was extracted with DCM and the combined organic layers were washed with NH$_4$Cl, NaHCO$_3$, water and brine. After drying over Na$_2$SO$_4$ the mixture was evaporated to give crude material which had to be purified by column chromatography (SiO$_2$; 680 g, CHCl$_3$:MeOH 8:1+ 0.1% AcOH to CHCl$_3$:MeOH 4:1+0.1% AcOH. All amine containing fractions were pooled and treated with saturated NaHCO$_3$, brine, drying over Na$_2$SO$_4$ and evaporation give pure (3R,18R,20S)-3-(acetamino)-N-benzyloxy-11-oxo-olean-12-en-29-amide (0.726 g, 18.5%) as white solid foam Optical rotation: $[\alpha]_D^{20}$=+111.6 (c=1.0 in CHCl$_3$)

Rf-value=0.33 (CHCl$_3$:MeOH 9:1+0.1% AcOH)

$^1$H-NMR (CDCl$_3$): δ 0.67 (s, 3H, H28), 0.87-0.93 (d, 6H, H23, H24), 0.93-1.02 (m, 1H, H2$_b$), 1.09 (s, 3H, H26), 1.15 (s, 3H, H25), 1.12-1.16 (m, 1H, H15$_b$), 1.17 (s, 3H, H29), 1.21-1.27 (m, 1H, H3), 1.39 (s, 3H, H27), 1.27-1.41 (m, 6H, H1$_b$, H6$_b$, H16$_b$, H21$_b$, H22$_b$, H22$_a$), 1.41-1.52 (m, 2H, H7$_b$, H7$_a$), 1.53-1.77 (m, 3H, H1$_a$, H16$_a$, H19$_b$), 1.76-1.86 (m, 1H, H15$_a$), 1.93-2.15 (m, 4H, H2$_a$, H18, H19$_a$, H21$_a$), 2.46 (s, 1H, H9), 2.47-2.56 (m, 1H, H6$_a$), 2.62-2.96 (m, 1H, H5), 5.52 (s, 1H, H12), 6.93 (s, 1H, DpmO—CH-Ph$_2$), 7.22-7.43 (m, 10H, Dpm)

$^{13}$C-NMR (CDCl$_3$): δ 16.5 (q, C25), 17.4 (t, C7), 18.7 (q, C26), 23.5 (q, C23/24), 23.6 (q, C27), 25.6 (t, C16), 26.4 (2xt, C2, C15), 28.3 (2xq, C28, C29), 28.8 (q, C23/24), 31.2 (t,

C21), 31.7 (s, C17), 32.7 (t, C6), 33.6 (t, C1), 36.8 (s, C4), 37.4 (s, C10), 37.5 (t, C22), 41.1 (t, C19), 43.2 (s, C20), 44.0 (s, C8), 45.5 (s, C14), 48.0 (2×d, C3, C18), 56.2 (d, C5), 61.8 (d, C9), 76.6 (d, Dpm O—CH-Ph$_2$), 127.0 (2×d, Dpm), 127.3 (2×d, Dpm), 127.8 (d, Dpm), 128.1 (d, Dpm), 128.4 (2×d, Dpm), 128.58 (d, C12), 128.63 (2×d, Dpm), 140.10 (s, Dpm), 140.13 (s, Dpm), 168.8 (s, C13), 175.2 (s, C30), 200.3 (s, C11)

To a solution of (3R,18R,20S)-3-(amino)-11-oxo-olean-12-en-29-oic acid, diphenylmethyl ester (500 mg, 0.79 mmol, 1.0 equiv) in dry DCM (10 mL) TEA (0.76 mL, 5.5 mmol, 7.0 equiv) followed by acetic anhydride (0.37 mL, 3.93 mmol, 5.0 equiv) were added at 0° C. The reaction mixture was stirred at 0° C. monitored by TLC (Hex:EtOAc 1:2, CHCl$_3$: MeOH 9:1+AcOH). After 1 h the reaction mixture was diluted with EtOAc, washed with diluted HCl twice, with NaHCO$_3$ and brine, dried over Na$_2$SO$_4$ and evaporated to give crude material which was purified by column chromatography (SiO$_2$: 60 g, Hex:EtOAc 1:3) to give pure (3R,18R,20S)-3-(acetamino)-11-oxo-olean-12-en-29-oic acid, diphenylmethyl ester as white solid (509 mg, 95.5%).

Optical rotation: $[\alpha]_D^{20}$=+99.0 (c=1.0 in CHCl$_3$)

Rf-value=0.20 (Hex:EtOAc 1:2)

$^1$H-NMR (CDCl$_3$): δ 0.68 (s, 3H, H28), 0.72-0.79 (m, 1H, H5), 0.88 (s, 3H, H23/24), 0.94-0.99 (m, 4H, H1$_b$, H23/24), 0.99-1.04 (m, 1H, H16$_b$), 1.10 (s, 3H, H26), 1.12-1.22 (m, 7H, H15$_b$, H25, H29), 1.23-1.26 (m, 1H, H22$_b$), 1.28-1.38 (m, 3H, H2$_b$, H21$_b$, H22$_a$), 1.38-1.44 (m, 2H, H2$_a$, H6$_b$), 1.41 (s, 3H, H27), 1.45-1.57 (m, 2H, H7$_b$, H7$_a$), 1.59-1.73 (m, 2H, H6$_a$, H19$_b$), 1.74-1.89 (m, 1H, 15$_a$), 1.95-2.12 (m, 4H, H16$_a$, H18, H19$_a$, H21$_a$), 2.03 (s, 3H, Ac—CH$_3$), 2.38 (d, 1H, H9), 2.66-2.77 (m, 1H, H1$_a$), 3.82-3.89 (m, 1H, H3), 5.51 (s, 1H, H12), 6.93 (s, 1H, Dpm O—CH-Ph$_2$), 7.24-7.42 (m, 10H, Dpm)

$^{13}$C-NMR (CDCl$_3$): δ 16.4 (q, C25), 17.3 (t, C7), 18.7 (q, C26), 13.1 (q, C23/24), 23.2 (t, C2), 23.6 (q, C27), 23.8 (q, Ac—CH$_3$), 26.4 (t, C16), 26.4 (t, C15), 28.2 (q, C29), 28.3 (q, C28), 28.4 (q, C23/24), 31.2 (t, C21), 31.7 (s, C17), 32.6 (t, C6), 35.0 (t, C1), 36.6 (s, C4), 37.3 (s, C10), 37.5 (t, C22), 41.2 (t, C19), 43.2 (s, C20), 44.0 (s, C8), 45.5 (s, C14), 48.0 (d, C18), 51.2 (d, C5), 53.6 (d, C3), 61.8 (d, C9), 76.6 (d, -Dpm-O—CH-Ph2), 127.0 (2×d, Dpm), 127.2 (2×d, Dpm), 127.9 (d, Dpm), 128.1 (d, Dpm), 128.5 (3×d, 2×Dpm, C12), 128.6 (2×d, Dpm), 140.07 (s, Dpm), 140.11 (s, Dpm), 169.0 (s, Ac—CO), 169.2 (s, C13), 175.2 (s, C30), 199.7 (s, C11)

(3R,18R,20S)-3-(Acetamino)-11-oxo-olean-12-en-29-oic acid, diphenylmethyl ester (250 mg, 0.37 mmol, 1.0 equiv) was dissolved in MeOH:EtOAc:AcOH 50:50:1 (6 mL) The atmosphere was exchanged to argon, before Pd/C (25 mg, 10%) was added. The atmosphere was exchanged to H$_2$ and the reaction was stirred at RT monitored by TLC (Hex:EtOAc 1:2). Upon complete conversion the reaction atmosphere was exchanged to argon, the reaction mixture was filtered over Celite® and washed with MeOH:EtOAc 1:1. The solvents were evaporated and the crude material was purified by column chromatography (SiO$_2$: 10 g, 50 mL Hex:EtOAc 1:1 to Hex:MeOH 5:1) to give pure (3R,18R,20S)-3-(acetamino)-11-oxo-olean-12-en-29-oic acid (0.187 g, 98.9%) as white solid.

Optical rotation: $[\alpha]_D^{20}$=+95.0 (c=1.0 in CHCl$_3$:MeOH)

Rf-value=0.27 (DCM:MeOH 8:1)

$^1$H-NMR (CDCl$_3$): δ 0.84 (s, 3H, H28), 0.86 (s, 3H, H23/24), 0.93-1.29 (m, 4H, H1$_b$, H5, H15$_b$, H16$_b$), 0.98 (s, 3H, H23/24), 1.15 (s, 3H, H26), 1.16 (s, 3H, H25), 1.19 (s, 3H, H29), 1.28-1.59 (m, 8H, H2$_a$, H2$_b$, H6$_b$, H7$_a$, H7$_b$, H21$_b$, H22$_a$, H22$_b$), 1.46 (s, 3H, H27), 1.58-1.76 (m, 2H, H6$_a$, H19$_b$), 1.84-2.15 (m, 4H, H10$_a$, 15a, 19a, 21a), 2.02 (s, 3H, Ac—CH$_3$), 2.15-2.27 (m, 1H, H18), 2.56 (s, 1H, H9), 2.62 (s, 1H, H1$_a$), 3.79 (s, 1H, H9), 5.66 (s, 1H, H12)

$^{13}$C-NMR (CDCl$_3$): δ 16.1 (q, C25), 17.0 (t, C7), 18.3 (q, C26), 22.2 (q, Ac—CH$_3$), 22.8 (q, C27), 22.9 (t, C2), 23.0 (q, C23/24), 26.0 (t, C15), 26.1 (t, C16), 27.8 (q, C23/24), 28.1 (q, C29), 28.2 (q, C28), 30.7 (t, C21), 31.5 (s, C17), 32.1 (t, C6), 33.9 (t, C1), 36.0 (s, C4), 36.9 (s, C10), 37.4 (t, C22), 40.9 (t, C19), 43.1 (s, C20), 43.4 (s, C8), 45.4 (s, C14), 48.1 (d, C18), 49.6 (d, C5), 53.6 (d, C3), 61.2 (d, C9), 127.7 (d, C12), 170.6 (s, Ac—CO), 171.0 (s, C13), 179.2 (s, C30), 201.2 (s, C11)

(3R,18R,20S)-3-(Acetamino)-11-oxo-olean-12-en-29-oic acid (100 mg, 0.20 mmol, 1.0 equiv was stirred in a mixture of SOCl$_2$ (2.8 mL, 39.1 mmol, 200.0 equiv) and toluene (2.8 mL) overnight. Upon complete conversion was observed according to TLC (SiO$_2$, DCM:MeOH 8:1) excess SOCl$_2$ was evaporated and the residue was coevaporated from toluene twice. A solution of NH$_2$OBn (29 mg 0.23 mmol, 1.20 equiv) and TEA (54 μL, 0.40 mmol, 2.0 equiv) in acetonitrile was stirred at 0° C. for 1 h, before it was added in one portion to a solution of acid chloride in acetonitrile (2 mL). The reaction mixture was stirred at RT monitored by TLC (SiO$_2$, DCM: Et$_2$O 1:1). After 1.5 h complete was observed and solvents were evaporated, the residue was taken up in DCM and washed with water, NaHCO$_3$ and brine, dried over Na$_2$SO$_4$ and evaporated. The crude material was purified by flash column chromatography (SiO$_2$: 10 g, 100 mL DCM:Et$_2$O 5:1, 160 mL DCM:MeOH 30:1, 200 mL DCM:MeOH 10:1, fractions a 20 mL to give (3R,18R,20S)-3-(acetamino)-N-benzyloxy-11-oxo-olean-12-en-29-amide (0.102 g, 84.6%).

Optical rotation: $[\alpha]_D^{20}$=+89.6 (c=1.0 in CHCl$_3$:MeOH 3:1)

Rf-value=0.41 (DCM:MeOH 5:1)

$^1$H-NMR (CDCl$_3$): δ 0.68-0.77 (m, 1H, H5), 0.72 (s, 3H, H28), 0.80 (s, 3H, H23/24), 0.86-1.00 (m, H, H2b, H16b), 0.90 (s, 3H, H25), 1.00-1.16 (m, 1H, H15b), 1.06 (s, 6H, H26, H29), 1.09 (s, 3H, H23/24), 1.16-1.50 (m, 7H, H2a, H2b, H6b, H7a, H7b, H22a, H22b), 1.31 (s, 3H, H27), 1.50-1.82 (m, 5H, H6a, H16a, H19a, H19b, H21b), 1.82-2.08 (m, 3H, H15a, H18, H21a), 1.97 (s, 3H, Ac—CH3), 2.32 (s, 1H, H9), 2.54-2.65 (td, 1H, H2a), 3.72-3.81 (m, 1H, H3), 4.88 (s, 2H, CH2-Ph), 5.43 (s, 1H, H12), 7.22-7.38 (m, 5H, Aromat), 8.71 (s, 1H, NH)

$^{13}$C-NMR (CDCl$_3$): δ 16.5 (q, C25), 17.2 (t, C7), 18.6 (q, C26), 23.1 (q, C23/24), 23.6 (t, 2×q, C2, Ac—CH3, C27), 26.3 (2×t, C15, C16), 28.4 (2×q, C23/24, C28), 29.4 (q, C29), 31.2 (t, C21), 31.7 (s, C17), 32.4 (t, C6), 34.8 (t, C1), 36.5 (s, C4), 37.2 (s, C10), 37.3 (t, C22), 41.1 (t, C19), 42.9 (s, C20), 43.2 (s, C8), 45.5 (s, C14), 47.8 (d, C18), 51.0 (d, C5), 53.8 (d, C3), 61.7 (d, C9), 77.9 (t, CH2-Ph), 128.4 (d, C12), 128.6 (2×d, Ar—C3, Ar—C5), 128.8 (d, Ar—C4), 129.2 (d,

Ar—C2, Ar—C6), 135.3 (s, Ar—C1), 169.2 (s, Ac—CO), 169.5 (s, C13), 173.5 (s, C30), 200.0 (s, C11)

Example 26

Compound 26

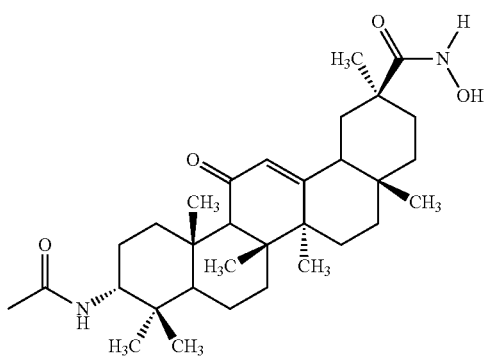

(3R,18R,20S)-3-(Acetamino)-N-hydroxy-11-oxo-olean-12-en-29-amide (3R,18R,20S)-3-(Acetamino)-N-benzyloxy-11-oxo-olean-12-en-29-amide (90 mg, 0.15 mmol, 1.0 equiv) was dissolved in THF (2 mL). The atmosphere was exchanged to argon, before Pd/C (18 mg, 20%) was added. The atmosphere was exchanged to $H_2$ and the reaction was stirred at RT monitored by TLC (DCM:MeOH 5:1). Upon complete conversion the reaction atmosphere was exchanged to argon, the reaction mixture was filtered over Celite® and washed with THF. Solvents were removed in vacuo and the residue was purified by flash column chromatography ($SiO_2$: 6 g, 40 mL DCM:$Et_2O$ 1:1+AcOH, 200 mL DCM:MeOH 20:1 to DCM:MeOH 5:1, fractions á 6 mL). Target compound containing fractions were pooled and washed with $NaHCO_3$ and brine, dried over $Na_2SO_4$ and evaporated and dried to give to give pure (3R,18R,20S)-3-(acetamino)-N-hydroxy-11-oxo-olean-12-en-29-amide (0.031 g, 40.0%).

Optical rotation: $[\alpha]_D^{20}$=+87.8 (c=1.0 in $CHCl_3$:MeOH 3:1)

Rf-value=0.29 (DCM:MeOH 5:1)

$^1$H-NMR (CDCl3): δ 0.71-0.93 (m, 2H, H5, H16b), 0.82 (s, 3H, H28), 0.87 (s, 3H, H23/24), 0.93-1.09 (m, 2H, H1b, H15b), 0.97 (s, 3H, H23/24), 1.09-1.30 (m, 2H, H16a, H21b), 1.13 (s, 3H, H26), 1.15 (s, 3H, H25), 1.19 (s, 3H, H29), 1.30-1.58 (m, 7H, H2a, H2b, H6b, H7a, H7b, H22a, H22b), 1.41 (s, 3H, H27), 1.58-1.76 (m, 2H, H6a, H19b), 1.77-1.95 (m, 2H, H15a, H19a), 1.94-2.13 (m, 1H, H21a), 2.03 (s, 3H, Ac—CH3), 2.15-2.32 (m, 1H, H18), 2.41 (s, 1H, H9), 2.57-2.71 (m, 1H, H1a), 3.78-3.89 (m, 1H, H3), 5.78 (s, 1H, H12)

$^{13}$C-NMR (CDCl$_3$): δ 16.5 (q, C25), 17.2 (t, C7), 18.6 (q, C26), 23.1 (q, C23/24), 23.6 (2×q, Ac—CH3, C27), 26.4 (3×t, C2, C15, C16), 28.4 (2×q, C23/24, C28), 29.5 (q, C29), 30.9 (t, C21), 31.8 (s, C17), 32.4 (t, C6), 34.8 (t, C1), 36.5 (s, C4), 37.2 (s, C10, t, C22), 40.8 (t, C19), 42.3 (s, C20), 43.3 (s, C8), 45.6 (s, C14), 47.7 (d, C18), 51.0 (d, C5), 53.7 (d, C3), 61.7 (d, C9), 128.5 (d, C12), 169.7 (s, Ac—CO), 169.9 (s, C13), 173.7 (s, C30), 200.7 (s, C11)

Example 27

Compound 27

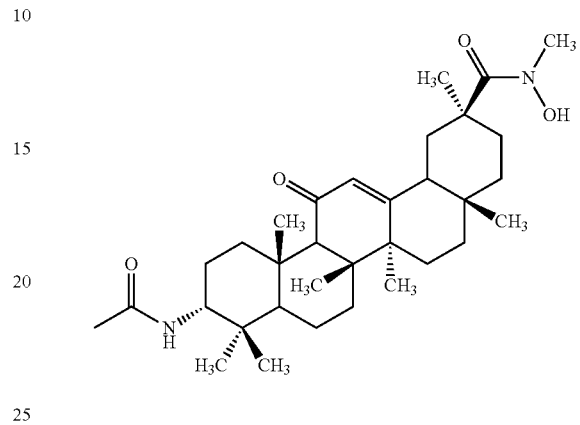

(3R,18R,20S)-3-(Acetamino)-N-hydroxy-N-methyl-11-oxo-olean-12-en-29-amide (3R,18R,20S)-3-(Acetamino)-11-oxo-olean-12-en-29-oic acid (50 mg, 0.098 mmol, 1.0 equiv) was stirred in a mixture of $SOCl_2$ (1.4 mL, 19.5 mmol, 200.0 equiv) and toluene (1.4 mL) at reflux temperature. After 2 h complete conversion was observed according to TLC ($SiO_2$, DCM:MeOH 5:1). The excess $SOCl_2$ was evaporated and the residue was coevaporated from toluene twice and the residue was dissolved in dry DCM (4 mL). MeNHOH.HCl (12 mg 0.15 mmol, 1.20 equiv) and TEA (54 μL, 0.39 mmol, 5.0 equiv) were added. The reaction mixture was stirred at RT monitored by TLC ($SiO_2$, DCM:MeOH 5:1). After 1 h complete conversion was observed and solvents were evaporated, the residue was taken up in DCM and washed with 2N HCl, water, $NaHCO_3$ and brine, dried over $Na_2SO_4$ and evaporated. The crude material was purified by flash column chromatography ($SiO_2$: 5 g, DCM:MeOH 30:1, 200 mL DCM:MeOH 10:1, to give pure (3R,18R,20S)-3-(acetamino)-N-hydroxy-N-methyl-11-oxo-olean-12-en-29-amid (0.038 g, 71.2%) as orange solid.

Optical rotation: $[\alpha]_D^{20}$=+96.4 (c=1.0 in $CHCl_3$:MeOH 3:1)

Rf-value=0.74 (DCM:MeOH 5:1)

1H-NMR (CDCl3): δ 8.59 (s, NH/OH), 6.02 (s, NH/OH), 5.68 (s, 1H, H12), 3.88-3.79 (d, 1H, J=7.6 Hz, H3), 3.36 (s, 3H, N-Me), 2.73-2.62 (d, 1H, J=13.1 Hz, H1a), 2.41 (s, 1H, H9), 2.27-1.96 (m, 4H, H18, H21a, H19a, H16a), 2.04 (s, 3H, Ac—CH3), 1.92-1.77 (m, 1H, H15a), 1.76-1.25 (m, 11H, H7a, H19b, H6a, H22a, H7b, H6b, H22b, H21b, H15b, H2a, H2b), 1.41 (s, 3H, H27), 1.21 (s, 3H, H29), 1.16 (s, 3H, H25), 1.13 (s, 3H, H26), 1.09-0.94 (m, 2H, H16b, H1b), 0.98 (s, 3H, H23/24), 0.87 (s, 3H, H23/24), 0.82 (s, 3H, H28), 0.84-0.75 (m, 1H, H5)

13C-NMR (CDCl3): δ 200.4 (s, C11), 173.8 (s, C30), 170.5 (s, Ac—CO), 169.6 (s, C13), 128.3 (d, C12), 61.8 (d, C9), 53.8 (d, C3), 51.1 (d, C5), 48.4 (d, C18), 45.5 (s, C14), 43.5 (s, C8), 43.4 (s, C20), 42.6 (t, C19), 38.3 (q, N-Me), 37.7 (t, C22), 37.3 (s, C4), 36.5 (s, C10), 34.9 (t, C1), 32.6 (t, C7), 32.5 (s, C17), 31.8 (t, C21), 28.5 (q, C28), 28.4 (q, C23/24), 26.7 (t, C16), 26.4 (2×t, C2, C15), 26.3 (q, C29), 23.6 (q, Ac—CH3), 23.4 (q, C27), 23.2 (q, C23/24), 18.7 (q, C26), 17.3 (t, C6), 16.5 (q, C25)

Example 28

Compound 28

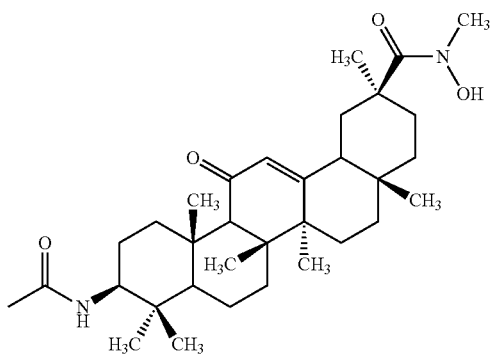

(3S,18R,20S)-3-(Acetamino)-N-hydroxy-N-methyl-11-oxo-olean-12-en-29-amide (3S,18R,20S)-3-(Acetamino)-11-oxo-olean-12-en-29-oic acid (300 mg, 0.59 mmol, 1.0 equiv) was stirred in a mixture of SOCl$_2$ (8.5 mL, 117 mmol, 200 equiv) and toluene (8.5 mL) at reflux temperature. After 3 h and complete conversion according to TLC (SiO$_2$, DCM:MeOH 5:1) the excess SOCl$_2$ was evaporated and the residue was coevaporated from toluene twice and the residue was dissolved in dry DCM (12 mL). MeNHOH.HCl (73 mg 0.88 mmol, 1.5 equiv) and TEA (325 µL, 2.35 mmol, 4.0 equiv) were added. The reaction mixture was stirred at RT monitored by TLC (SiO$_2$, DCM:MeOH 5:1). After 1 h complete conversion was observed and solvents were evaporated, the residue was taken up in DCM and washed with water, NaHCO$_3$ and brine, dried over Na$_2$SO$_4$ and evaporated. The crude material was purified by flash column chromatography (SiO$_2$: 85 g, DCM:MeOH 20:1) to give pure (3S,18R,20S)-3-(acetamino)-N-hydroxy-N-methyl-11-oxo-olean-12-en-29-amide (0.255 g, 80.4%) as white solid.

Optical rotation: $[\alpha]_D^{20}$=+115.2 (c=1.0 in CHCl$_3$:MeOH 3:1)

Rf-value=0.49 (DCM:MeOH 9:1+AcOH)

1H-NMR (CDCl$_3$:MeOD 5:1): δ 8.34 (s, NH/OH), 5.68 (s, 1H, H12), 3.74-3.62 (m, 1H, H3), 3.35 (s, 3H, N-Me), 2.80-2.70 (td, 1H, J 13.3, J=2.4 Hz, H1a), 2.39 (s, 1H, H9), 2.26-2.05 (m, 4H, H21a, H19a, H18, H16a), 2.03 (s, 3H, Ac—CH3), 1.90-1.75 (dt, 1H, J 13.6, J=4.0 Hz, H15a), 1.75-1.45 (m, 7H, H7a, H19b, H2a, H6a, H22a, H1b, H2b), 1.45-1.23 (m, 5H, H7b, H6b, H22b, H21b, H15b), 1.36 (s, 3H, H27), 1.21 (s, 3H, H29), 1.13 (s, 3H, H23/24), 1.11 (s, 3H, H26), 1.07-0.96 (m, 1H, H16b), 0.93-0.83 (m, 1H, H5), 0.90 (s, 3H, H23/24), 0.81 (s, 3H, H28), 0.80 (s, 3H, H25)

13C-NMR (CDCl$_3$:MeOD 5:1): δ 200.6 (s, C11), 174.0 (s, C30), 170.5 (s, C13), 170.0 (s, Ac—CO), 128.2 (d, C12), 61.7 (d, C9), 56.7 (d, C3), 55.5 (d, C5), 48.5 (d, C18), 45.3 (s, C14), 43.6 (s, C8), 43.3 (s, C20), 42.3 (t, C19), 39.7 (t, C1), 38.3 (q, N-Me), 38.0 (s, C4), 37.7 (t, C22), 36.9 (s, C10), 32.7 (t, C7), 32.5 (s, C17), 31.8 (t, C21), 28.5 (2×q, C23/24, C28), 26.7 (t, C16), 26.4 (t, C15), 26.3 (q, C29), 25.3 (t, C2), 23.6 (q, Ac—CH3), 23.0 (q, C27), 18.6 (q, C26), 17.7 (t, C6), 16.6 (q, C25), 16.3 (q, C23/24)

Example 29

Compound 29

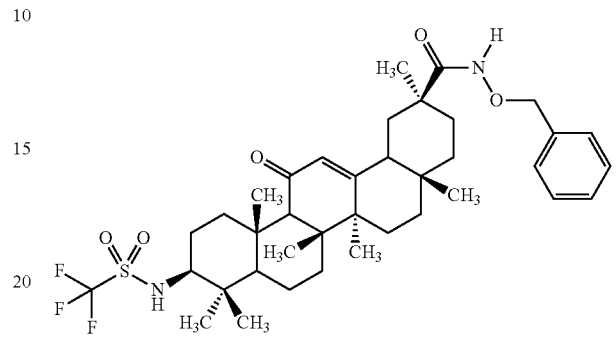

(3S,18R,20S)-N-Benzyloxy-11-oxo-3-{(trifluoromethyl)sulfonyl]amino}-olean-12-en-29-amide To a solution of (3S,18R,20S)-3-(amino)-11-oxo-olean-12-en-29-oic acid, diphenylmethyl ester (2.0 g, 3.15 mmol, 1.0 equiv) and TEA (1.31 mL, 9.44 mmol, 3.0 equiv) in dry DCM (50 mL) a prechilled solution of Tf$_2$O (626 µL, 3.77 mmol, 1.20 equiv) in dry DCM (10 mL) was added at −10° C. Upon complete addition the reaction mixture was stirred at −10° C. and was monitored by TLC (Hex:EtOAc 2:1, CHCl$_3$:MeOH 9:1+AcOH). Upon complete conversion, the reaction mixture was directly rotated onto SiO$_2$ and purified by column chromatography (Hex:EtOAc 7:1) to give (3S,18R,20S)-11-oxo-3-{(trifluoromethyl)sulfonyl]amino}-olean-12-en-29-oic acid, diphenylmethyl ester as white solid foam (2.0 g, 82.6%).

Rf-value=0.46 (Hex:EtOAc 2:1)

1H-NMR (CDCl3): δ 7.41-7.25 (m, 5H, Dpm), 6.93 (s, 1H, Dpm), 5.51 (s, 1H, H12), 4.07 (s, NH), 3.25-3.11 (dd, 1H, J 12.6, J=4.1 Hz, H3), 2.89-2.71 (td, 1H, J 13.4, J=3.4 Hz, H1a), 2.38 (s, 1H, H9), 2.09-1.94 (m, 4H, H21a, H16a, H19a, H18), 1.84-1.59 (m, 6H, H15a, H19b, H7a, H2a, H2b, H6a), 1.50-1.23 (m, 5H, H6b, H7b, H21b, H22a, H22b), 1.38 (s, 3H, H27), 1.20 (s, 3H, H29), 1.19-0.95 (m, 3H, H15b, H1b, H16b), 1.14 (s, 3H, H25), 1.10 (s, 3H, H26), 1.02 (s, 3H, H23/24), 0.85-0.79 (m, 1H, H5), 0.83 (s, 3H, H23/24), 0.67 (s, 3H, H28)

13C-NMR (CDCl3): δ 200.4 (s, C11), 175.4 (s, C30), 170.0 (s, C13), 139.8 (s, Dpm), 139.7 (s, Dpm), 128.3 (2×d, Dpm), 128.2 (2×d, Dpm), 127.9 (2×d, C12, Dpm), 127.6 (d, Dpm), 127.0 (2×d, Dpm), 126.7 (2×d, Dpm), 76.7 (d, Dpm), 63.9 (d, C3), 61.4 (d, C9), 55.3 (d, C5), 47.9 (d, C18), 45.1 (s, C14), 43.8 (s, C8), 43.0 (s, C20), 40.8 (t, C19), 39.7 (t, C1), 38.4 (s, C4), 37.2 (t, C22), 36.6 (s, C10), 32.4 (t, C7), 31.5 (s, C17), 30.8 (t, C21), 27.99 (q, C23/24), 27.96 (q, C29), 27.8 (q, C28), 26.1 (t, C16), 26.0 (t, C15), 25.3 (t, C2), 22.9 (q, C27), 18.3 (q, C26), 17.7 (t, C6), 16.0 (q, C23/24), 15.9 (q, C25)

(3S,18R,20S)-11-oxo-3-{(trifluoromethyl)sulfonyl]amino}-olean-12-en-29-oic acid, diphenylmethyl ester (2.0 g, 2.6 mmol, 1.0 equiv) was dissolved in MeOH:AcOH 100:1 (40 mL), the atmosphere was exchanged to argon, before Pd/C (200 mg, 10%) was added. The atmosphere was exchanged to H₂ and the reaction was stirred at RT monitored by TLC (Hex:EtOAc 2:1). Upon complete conversion the reaction atmosphere was exchanged to argon, the reaction mixture was filtered through a short bed of Celite®, evaporated and purified by column chromatography (SiO₂: 40 g, Hex:EtOAc with 0.1% AcOH) to give (3S,18R,20S)-11-oxo-3-{(trifluoromethyl)-sulfonyl]amino}-olean-12-en-29-oic acid as white solid (1.15 g, 97.6%).

Optical rotation: $[\alpha]_D^{20}$=+96.4 (c=1.0 in CHCl₃:MeOH 3:1)

Rf-value=0.40 (CHCl₃:MeOH 9:1+AcOH)

1H-NMR (CDCl₃): δ 5.66 (s, 1H, H12), 4.32 (s, NH), 3.18-3.08 (dd, 1H, J 12.7, J=4.4 Hz, H3), 2.84-2.74 (td, 1H, J 13.4, J=3.3 Hz, H1a), 2.41 (s, 1H, H9), 2.26-2.16 (dd, 1H, J 13.5, J=3.8 Hz, H18), 2.14-1.74 (m, 4H, H16a, H21a, H19a, H15a), 1.73-1.56 (m, 5H, H7a, H2a, H2b, H6a, H19b), 1.56-1.30 (m, 5H, H6b, H7b, H22a, H22b, H21b), 1.39 (s, 3H, H27), 1.30-1.22 (m, 1H, H15b), 1.19 (s, 3H, H29), 1.14 (s, 6H, H25, H26), 1.11-0.97 (m, 2H, H1b, H16b), 1.03 (s, 3H, H23/24), 0.87-0.76 (m, 1H, H5), 0.83 (s, 6H, H23/24, H28)

13C-NMR (CDCl₃): δ 200.8 (s, C11), 179.0 (s, C30), 171.0 (s, C13), 127.7 (d, C12), 63.8 (d, C3), 61.4 (d, C9), 55.3 (d, C5), 48.1 (d, C18), 45.1 (s, C14), 43.4 (s, C8), 43.1 (s, C20), 40.8 (t, C19), 39.6 (t, C1), 38.4 (s, C4), 37.4 (t, C22), 36.5 (s, C10), 32.3 (t, C7), 31.5 (s, C17), 30.7 (t, C21), 28.1 (q, C23/24), 28.0 (q, C29), 27.9 (q, C28), 26.1 (t, C16), 26.0 (t, C15), 25.3 (t, C2), 22.9 (q, C27), 18.2 (q, C26), 17.7 (t, C6), 15.9 (q, C23/24), 15.8 (q, C25)

((3S,18R,20S)-11-oxo-3-{(trifluoromethyl)sulfonyl]amino}-olean-12-en-29-oic acid (500 mg, 0.83 mmol, 1.0 equiv) was stirred in a mixture of SOCl₂ (12 mL, 166 mmol, 200 equiv) and toluene (12 mL) at reflux temperature. After 2 h and complete conversion according to TLC (SiO₂, DCM:MeOH 9:1+AcOH) the excess SOCl₂ was evaporated and the residue was coevaporated from toluene twice and the residue was dissolved in dry DCM (20 mL). NH₂OBn (123 mg 1.0 mmol, 1.2 equiv) and TEA (230 μL, 1.66 mmol, 5.0 equiv) were added. The reaction mixture was stirred at RT monitored by TLC (SiO₂:CHCl₃:MeOH 9:1+AcOH, Hex:EtOAc 2:1). After 1 h complete conversion was observed and solvents were evaporated, the residue was taken up in DCM and washed with water, NaHCO₃ and brine, dried over Na₂SO₄ and evaporated. The crude material was purified by flash column chromatography (SiO₂: 30 g, Hex:EtOAc and CHCl₃:MeOH+AcOH) to give (3S,18R,20S)-N-benzyloxy-11-oxo-3-{(trifluoromethyl)sulfonyl]amino}-olean-12-en-29-amide (0.476 g, 81.0%) as white solid.

Optical rotation: $[\alpha]_D^{20}$=+106.4 (c=1.0 in CHCl₃:MeOH 3:1)

Rf-value=0.67 (DCM:MeOH 9:1+AcOH)

ESI-MS (negative mode): O₃₇H₅₃F₃N₂O₅S (MM=706.92): m/z=705.4 (M-H)

¹H-NMR (CDCl₃:MeOD 5:1): δ 7.48-7.29 (m, 5H, Bn), 5.49 (s, 1H, H12), 4.91 (s, 2H, Bn), 4.09 (s, NH), 3.17-3.08 (m, 1H, H3), 2.86-2.75 (m, 1H, H1a), 2.38 (s, 1H, H9), 2.09-1.83 (m, 3H, H18, H16a, H21a), 1.93-1.71 (m, 2H, H15a, H19a), 1.71-1.55 (m, 5H, H7a, H6a, H2a, H2b, H19b), 1.55-1.38 (m, 2H, H6b, H7b), 1.38-1.25 (m, 3H, H22a, H22b, H21b), 1.35 (s, 3H, H27), 1.25-1.06 (m, 1H, H15b), 1.14 (s, 3H, H25), 1.12 (s, 3H, H26), 1.11 (s, 3H, H29), 1.06-0.96 (m, 2H, H1b, H16b), 1.02 (s, 3H, H23/24), 0.87-0.73 (m, 1H, H5), 0.83 (s, 3H, H23/24), 0.76 (s, 3H, H28)

¹³C-NMR (CDCl₃:MeOD 5:1): δ 200.9 (s, C11), 173.7 (s, C30), 170.7 (s, C13), 135.3 (s, Bn), 128.9 (2×d, Bn), 128.4 (d, Bn), 128.2 (2×d, Bn), 127.8 (d, C12), 77.4 (t, Bn), 63.8 (d, C3), 61.4 (d, C9), 55.3 (d, C5), 47.5 (d, C18), 45.1 (s, C14), 43.0 (s, C8), 42.4 (s, C20), 40.5 (t, C19), 39.7 (t, C1), 38.4 (s, C4), 37.0 (t, C22), 36.6 (s, C10), 32.3 (t, C7), 31.3 (s, C17), 30.6 (t, C21), 28.7 (q, C23/24), 28.1 (q, C29), 28.0 (q, C28), 26.1 (2×t, C15, C16), 25.3 (t, C2), 23.0 (q, C27), 18.3 (q, C26), 17.7 (t, C6), 16.0 (q, C23/24), 15.9 (q, C25)

Example 30

Compound 30

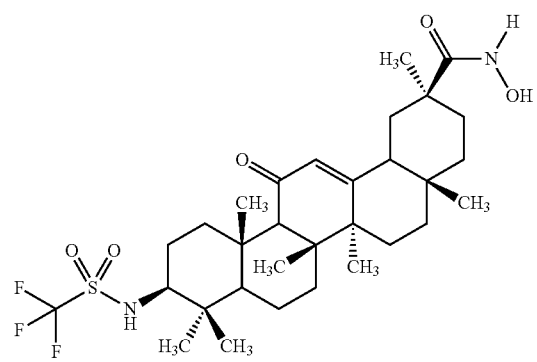

(3S,18R,20S)-N-Hydroxy-11-oxo-3-{(trifluoromethyl)sulfonyl]amino}-olean-12-en-29-amide ((3S,18R,20S)-N-Benzyloxy-11-oxo-3-{(trifluoromethyl)sulfonyl]amino}-olean-12-en-29-amide (375 mg, 0.53 mmol, 1.0 equiv) was dissolved in THF (7.5 mL). The atmosphere was exchanged to argon, before Pd/C (75 mg, 20%) was added. The atmosphere was exchanged to H₂ and the reaction was stirred at RT monitored by TLC (CHCl₃:MeOH 9:1+AcOH). Upon complete conversion the reaction atmosphere was exchanged to argon, the reaction mixture was filtered over Celite® and washed with THF. Solvents were removed in vacuo and the residue was purified by flash column chromatography (SiO₂: 85 g, DCM:MeOH 9:1-FAcOH to DCM:MeOH 5:1). Target compound containing fractions were pooled and washed with NaHCO₃ and brine, dried over Na₂SO₄ and evaporated and dried to give pure target compound (0.149 g, 45.4%) as orange solid.

Optical rotation: $[\alpha]_D^{20}$=+96.2 (c=1.0 in CHCl₃:MeOH 3:1)

Rf-value=0.43 (DCM:MeOH 9:1+AcOH)

1H-NMR (CDCl₃:MeOD 5:1): δ 5.60 (s, 1H, H12), 3.93 (s, NH/OH), 3.09-3.00 (m, 1H, H3), 2.77-2.66 (m, 1H, H1a), 2.31 (s, 1H, H9), 2.16-1.69 (m, 6H, H18, H16a, H21a, H19a, H2a, H2b), 1.65-1.50 (m, 4H, H19b, H7a, H6a, H15a), 1.42-1.17 (m, 5H, H6b, H7b, H22a, H22b, H21b), 1.30 (s, 3H, H27), 1.17-1.10 (m, 1H, H15b), 1.10-0.89 (m, 2H, H16b, H1b), 1.07 (s, 3H, H29), 1.05 (s, 6H, H25, H26), 0.94 (s, 3H, H23/24), 0.78-0.69 (m, 1H, H5), 0.75 (s, 3H, H23/24), 0.74 (s, 3H, H28)

13C-NMR (CDCl₃:MeOD 5:1): δ 201.2 (s, C11), 173.5 (s, C30), 171.0 (s, C13), 128.0 (d, C12), 64.0 (d, C3), 61.7 (d, C9), 55.5 (d, C5), 47.9 (d, C18), 45.4 (s, C14), 43.3 (s, C8), 42.3 (s, C20), 40.8 (t, C19), 39.9 (t, C1), 38.6 (s, C4), 37.2 (t, C22), 36.8 (s, C10), 32.5 (t, C7), 31.6 (s, C17), 30.7 (t, C21), 29.1 (q, C29), 28.3 (q, C28), 28.2 (q, C23/24), 26.3 (t, C16), 25.5 (t, C15), 25.0 (t, C2), 23.2 (q, C27), 18.5 (q, C26), 17.9 (t, C6), 16.2 (q, C23/24), 16.1 (q, C25)

Example 31

Compound 31

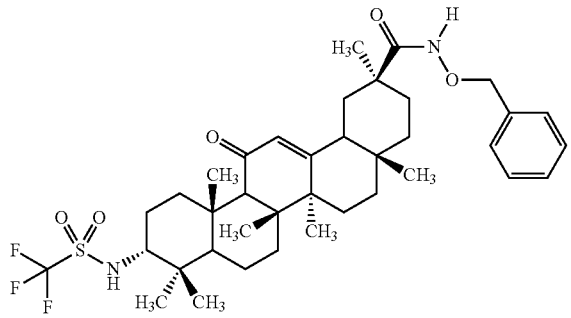

(3R,18R,20S)-N-Benzyloxy-11-oxo-3-{(trifluoromethyl)sulfonyl]amino}-olean-12-en-29-amide To a solution of (3R,18R,20S)-3-(amino)-11-oxo-olean-12-en-29-oic acid, diphenylmethyl ester (534 mg, 0.84 mmol, 1.0 equiv) and TEA (350 µL, 2.52 mmol, 3.0 equiv) in dry DCM (25 mL) a prechilled solution of Tf$_2$O (170 µL, 1.01 mmol, 1.2 equiv) in dry DCM (7 mL) was added at −10° C. Upon complete addition the reaction mixture was stirred at −10° C. and was monitored by TLC (Hex:EtOAc 2:1, CHCl$_3$:MeOH 9:1+AcOH). Upon complete conversion, the reaction mixture was directly rotated onto SiO$_2$ and purified by column chromatography (Hex:EtOAc 10:1) to give pure (3R,18R,20S)-[1-oxo-3-{(trifluoromethyl)sulfonyl]amino}-olean-12-en-29-oic acid, diphenylmethyl ester as white solid (0.427 g, 66.3%).

Rf-value=0.51 (Hex:EtOAc 2:1)

1H-NMR (CDCl3): δ 7.42-7.23 (m, 10H, Dpm), 6.93 (s, 1H, Dpm), 5.46-5.27 (s, 1H, H12), 5.56-5.47 (d, 10.02 Hz, NH), 3.41-3.32 (td, 1H, J 9.9, J=2.8 Hz, H3), 2.84-2.73 (td, 1H, J 14.5, J=3.0 Hz, H1a), 2.39 (s, 1H, H9), 2.21-1.94 (m, 5H, H2a, H21a, H19a, H16a, H18), 1.85-1.45 (m, 5H, H15a, H19b, H7a, H2b, H6a), 1.45-1.22 (m, 5H, H6b, H7b, H22a, H22b, H21b), 1.39 (s, 3H, H27), 1.22-1.12 (m, 1H, H15b), 1.18 (s, 3H, H29), 1.15 (s, 3H, H25), 1.09 (s, 3H, H26), 1.05-0.92 (m, 2H, H1b, H16b), 1.00 (s, 3H, H23/24), 0.99 (s, 3H, H23/24), 0.83-0.74 (m, 1H, H5), 0.66 (s, 3H, H28)

13C-NMR (CDCl3): δ 199.7 (s, C11), 175.2 (s, C30), 169.4 (s, C13), 140.15 (s, Dpm), 140.09 (s, Dpm), 128.6 (2×d, Dpm), 128.5 (2×d, Dpm), 128.3 (d, C12), 128.1 (d, Dpm), 127.8 (d, Dpm), 127.3 (2×d, Dpm), 127.0 (2×d, Dpm), 76.6 (d, Dpm), 61.8 (d, C3), 61.5 (d, C9), 50.3 (d, C5), 48.1 (d, C18), 45.4 (s, C14), 44.0 (s, C8), 43.3 (s, C20), 41.1 (t, C19), 37.5 (t, C22), 37.0 (s, C4), 37.0 (s, C10), 34.1 (t, C1), 32.4 (t, C7), 31.7 (s, C17), 31.2 (t, C21), 28.9 (q, C23/24), 28.3 (q, C28), 28.2 (q, C29), 26.3 (2×t, C15, C16), 23.8 (t, C2), 23.5 (q, C27), 23.0 (q, C23/24), 18.6 (q, C26), 17.2 (t, C6), 16.5 (q, C25)

((3R,18R,20S)-11-oxo-3-{(trifluoromethyl)sulfonyl]amino}-olean-12-en-29-oic acid, diphenylmethyl ester (430 mg, 0.56 mmol, 1.0 equiv) was dissolved in MeOH:AcOH 100:1 (45 mL), the atmosphere was exchanged to argon, before Pd/C (43 mg, 10%) was added. The atmosphere was exchanged to H$_2$ and the reaction was stirred at RT monitored by TLC (Hex:EtOAc 2:1, CHCl$_3$:MeOH 9:1+AcOH). Upon complete conversion the reaction atmosphere was exchanged to argon, the reaction mixture was filtered through a short bed of Celite®, evaporated and purified by column chromatography (SiO$_2$: 10 g, Hex:EtOAc 3:1 to Hex:EtOAc 2:1 with 0.1% AcOH) to give pure (3R,18R,20S)-11-oxo-3-{(trifluoromethyl)sulfonyl]amino}-olean-12-en-29-oic acid as white solid (332 mg, 98.5%).

Optical rotation: $[\alpha]_D^{20}$=+82.0 (c=1.0 in CHCl$_3$:MeOH 3:1)

Rf-value=0.41 (CHCl$_3$:MeOH 9:1+AcOH)

1H-NMR (CDCl3): δ 5.66 (s, 1H, 12), 3.84 (s, NH), 3.36-3.29 (t, 1H, J=2.8 Hz, H3), 2.68-2.56 (td, 1H, J 14.2, J=3.7 Hz, H1a), 2.58 (s, 1H, H9), 2.25-2.16 (dd, 1H, J 13.6, J=3.6 Hz, H18), 2.16-1.94 (m, 3H, H2a, H16a, H21a), 1.94-1.75 (m, 2H, H19a, H15a), 1.75-1.50 (m, 4H, H7a, H19b, H2b, H6a), 1.47-1.28 (m, 5H, H22a, H22b, H7b, H6b, H21b), 1.42 (s, 3H, H27), 1.28-1.10 (m, 2H, H15b, H1b), 1.19 (s, 3H, H29), 1.16 (s, 3H, H25), 1.14 (s, 3H, H26), 1.10-0.95 (m, 2H, H16b, H5), 0.99 (s, 3H, H23/24), 0.98 (s, 3H, H23/24), 0.83 (s, 3H, H28)

13C-NMR (CDCl3): δ 201.1 (s, C11), 179.1 (s, C30), 170.8 (s, C13), 127.8 (d, C12), 61.4 (d, C3), 61.0 (d, C9), 48.9 (d, C5), 48.2 (d, C18), 45.4 (s, C14), 43.5 (s, C8), 43.2 (s, C20), 41.0 (t, C19), 37.5 (t, C22), 36.74 (s, C4), 36.67 (s, C10), 33.3 (t, C1), 32.2 (t, C7), 31.6 (s, C17), 30.8 (t, C21), 28.5 (q, C23/24), 28.2 (q, C28), 28.1 (q, C29), 26.2 (t, C16), 26.1 (t, C15), 23.9 (t, C2), 22.9 (q, C27), 22.7 (q, C23/24), 18.4 (q, C26), 17.0 (t, C6), 16.3 (q, C25) ((3R,18R,20S)-11-oxo-3-{(trifluoromethyl)sulfonyl]amino}-olean-12-en-29-oic acid (150 mg, 0.25 mmol, 1.0 equiv) was stirred in a mixture of SOCl$_2$ (4 mL, 50 mmol, 200 equiv) and toluene (4 mL) at reflux temperature. After 2 h and complete conversion according to TLC (SiO$_2$, DCM:MeOH 9:1+AcOH, Hex:EtOAC 2:1) the excess SOCl$_2$ was evaporated and the residue was coevaporated from toluene twice and the residue was dissolved in dry DCM (10 mL). NH$_2$OBn (37.0 mg, 0.3 mmol, 1.20 equiv) and TEA (69 µL, 0.50 mmol, 5.0 equiv) were added. The reaction mixture was stirred at RT monitored by TLC (SiO$_2$:CHCl$_3$:MeOH 9:1+AcOH, Hex:EtOAc 2:1). After 2 h complete conversion was observed and solvents were evaporated, the residue was taken up in DCM and washed with water, NaHCO$_3$ and brine, dried over Na$_2$SO$_4$ and evaporated. The crude material was purified by flash column chromatography (SiO$_2$: 20 g, Hex:EtOAc 3:1 to Hex:EtOAc 1:1 with 0.1% AcOH) to give pure (3R,18R,20S)-N-benzyloxy-11-oxo-3-{(trifluoromethyl)sulfonyl]amino}-olean-12-en-29-amide (0.157 g, 89.2%) as orange solid.

Rf-value=0.68 (CHCl$_3$:MeOH 9:1+AcOH)

1H-NMR (CDCl$_3$:MeOD 5:1): δ 7.46-7.32 (m, 5H, Bn), 5.48 (s, 1H, H12), 4.91 (s, 2H, Bn), 4.17 (s, NH/OH), 3.36-3.31 (m, 1H, H3), 2.66-2.57 (m, 1H, H1a), 2.59 (s, 1H, H9), 2.16-2.08 (m, 1H, H2a), 2.08-1.96 (m, 2H, H18, H16a), 1.96-1.88 (m, 1H, H21a), 1.88-1.69 (m, 3H, H15a, H19a, H7a), 1.69-1.49 (m, 3H, H19b, H2b, H6a), 1.42-1.38 (m, 2H, H6b, H7b), 1.39 (s, 3H, H27), 1.34-1.27 (m, 3H, H22a, H22b, H21b), 1.25-1.15 (m, 2H, H15b, H1b), 1.16 (s, 3H, H25), 1.12 (s, 3H, H26), 1.11 (s, 3H, H29), 1.10-1.01 (m, 2H, H5, H16b), 0.99 (s, 3H, H23/24), 0.98 (s, 3H, H23/24), 0.77 (s, 3H, H28)

13C-NMR (CDCl$_3$:MeOD 5:1): δ 201.4 (s, C11), 173.7 (s, C30), 170.8 (s, C13), 135.3 (s, Bn), 128.9 (2×d, Bn), 128.4 (d, Bn), 128.2 (2×d, Bn), 127.7 (d, C12), 77.3 (t, Bn), 61.3 (d, C3), 60.9 (d, C9), 48.5 (d, C5), 47.5 (d, C18), 45.2 (s, C14), 43.1 (s, C8), 42.4 (s, C20), 40.5 (t, C19), 37.0 (t, C22), 36.7 (s, C4), 36.5 (s, C10), 33.1 (t, C1), 32.0 (t, C7), 31.3 (s, C17), 30.5 (t, C21), 28.7 (q, C29), 28.3 (q, C23/24), 28.0 (q, C28), 26.02 (t, C16), 25.98 (t, C15), 23.8 (t, C2), 22.8 (q, C27), 22.6 (q, C23/24), 18.3 (q, C26), 16.9 (t, C6), 16.2 (q, C25)

Example 32

Compound 32

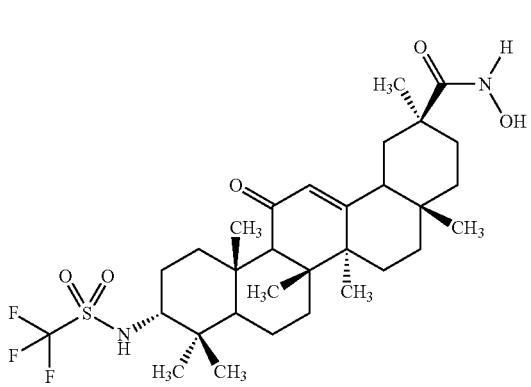

(3R,18R,20S)-N-Hydroxy-11-oxo-3-{(trifluoromethyl)sulfonyl]amino}-olean-12-en-29-amide (3R,18R,20S)-N-Benzyloxy-11-oxo-3-{(trifluoromethyl)sulfonyl]amino}-olean-12-en-29-amide (142 mg, 0.20 mmol, 1.0 equiv) was dissolved in THF (2.8 mL). The atmosphere was exchanged to argon, before Pd/C (28 mg, 20%) was added. The atmosphere was exchanged to $H_2$ and the reaction was stirred at RT monitored by TLC (CHCl$_3$:MeOH 9:1+AcOH). Upon complete conversion the reaction atmosphere was exchanged to argon, the reaction mixture was filtered over Celite® and washed with THF. Solvents were removed in vacuo and the residue was purified by flash column chromatography (SiO$_2$: 20 g, Hex:EtOAc 3:1 to DCM:MeOH 5:1). Target compound containing fractions were pooled and washed with NaHCO$_3$ and brine, dried over Na$_2$SO$_4$ and evaporated and dried to give pure (3R,18R,20S)-N-hydroxy-11-oxo-3-{(trifluoromethyl)sulfonyl]amino}-olean-12-en-29-amide (0.057 g, 64.0%) as orange solid.

Optical rotation: $[\alpha]_D^{20}$=+89.9 (c=1.0 in CHCl$_3$:MeOH 3:1)

Rf-value=0.44 (CHCl$_3$:MeOH 9:1+AcOH)

1H-NMR (CDCl$_3$:MeOD 5:1): δ 5.68 (s, 1H, H12), 4.02 (s, NH/OH), 3.35-3.30 (m, 1H, H3), 2.67-2.56 (m, 1H, H1a), 2.61 (s, 1H, H9), 2.34-2.00 (m, 3H, H18, H2a, H16a), 1.99-1.78 (m, 3H, H21a, H15a, H19a), 1.75-1.62 (m, 2H, H7a, H19b), 1.61-1.50 (m, 2H, H2b, H6a), 1.47-1.37 (m, 4H, H7b, H6b, H22a, H22b), 1.42 (s, 3H, H27), 1.27-1.01 (m, 5H, H15b, H1b, H21b, H16b, H5), 1.15 (s, 6H, H25, H29), 1.13 (s, 3H, H26), 0.99 (s, 3H, H23/24), 0.98 (s, 3H, H23/24), 0.83 (s, 3H, H28)

13C-NMR (CDCl$_3$:MeOD 5:1): δ 201.4 (s, C11), 173.5 (s, C30), 170.8 (s, C13), 127.7 (d, C12), 61.4 (d, C3), 60.9 (d, C9), 48.7 (d, C5), 47.8 (d, C18), 45.3 (s, C14), 43.2 (s, C8), 42.1 (s, C20), 40.7 (t, C19), 37.0 (t, C22), 36.7 (s, C4), 36.6 (s, C10), 33.2 (t, C1), 32.2 (t, C7), 31.4 (s, C17), 30.5 (t, C21), 28.9 (q, C29), 28.4 (q, C23/24), 28.1 (q, C28), 26.1 (2xt, C15, C16), 23.9 (t, C2), 22.8 (q, C27), 22.6 (q, C23/24), 18.4 (q, C26), 17.0 (t, C6), 16.2 (q, C25)

Example 33

Compound 33

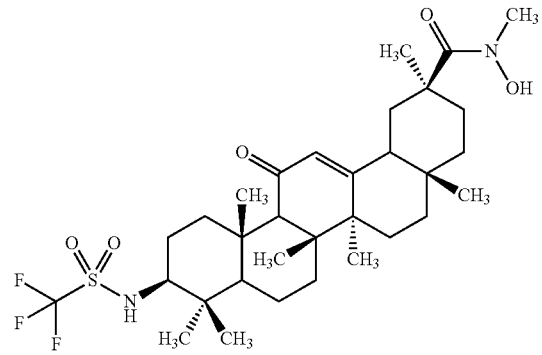

(3S,18R,20S)-N-Hydroxy-N-methyl-11-oxo-3-{(trifluoromethyl)sulfonyl]amino}-olean-12-en-29-amide ((3S,18R,20S)-11-oxo-3-{(trifluoromethyl)sulfonyl]amino}-olean-12-en-29-oic acid (300 mg, 0.50 mmol, 1.0 equiv) was stirred in a mixture of SOCl$_2$ (7.2 mL, 99.7 mmol, 200 equiv) and toluene (7.2 mL) at reflux temperature. After 3 h and complete conversion according to TLC (SiO$_2$, DCM:MeOH 9:1+AcOH) the excess SOCl$_2$ was evaporated and the residue was coevaporated from toluene twice and the residue was dissolved in dry DCM (25 mL). MeNHOH.HCl (62 mg, 0.75 mmol, 1.2 equiv) and TEA (276 μL, 2.0 mmol, 4.0 equiv) were added. The reaction mixture was stirred at RT monitored by TLC (SiO$_2$:CHCl$_3$:MeOH 9:1+AcOH). After 2 h complete conversion was observed and solvents were evaporated, the residue was taken up in DCM and washed with 2N HCl, water, NaHCO$_3$ and brine, dried over Na$_2$SO$_4$ and evaporated. The crude material was purified by flash column chromatography (SiO$_2$: 30 g, DCM:MeOH 40:1 to 30:1) to give pure (3S,18R,20S)-N-hydroxy-N-methyl-11-oxo-3-{(trifluoromethyl)sulfonyl]amino}-olean-12-en-29-amide (257 g, 81.4%) as white solid.

Optical rotation: $[\alpha]_D^{20}$=+97.1 (c=1.0 in CHCl$_3$:MeOH 3:1)

Rf-value=0.30 (DCM:MeOH 9:1+AcOH)

1H-NMR (CDCl3): δ 7.21 (s, NH/OH), 5.81 (s, 1H, H12), 3.70 (s, NH/OH), 3.33 (s, 3H, N-Me), 3.24-3.14 (m, 1H, H3), 2.88-2.80 (m, 1H, H1a), 2.40 (s, 1H, H9), 2.30-2.22 (d, 1H, J=13.6 Hz, H19a), 2.17-2.04 (m, 3H, H21a, H18, H16a), 1.98-1.88 (m, 1H, H2a), 1.87-1.57 (m, 6H, H2b, H15a, H19b, H7a, H6a, H22a), 1.48-1.34 (m, 3H, H7b, H6b, H22b), 1.37 (s, 3H, H27), 1.29-1.16 (m, 2H, H21b, H15b), 1.21 (s, 3H, H29), 1.13-0.99 (m, 2H, H1b, H16b), 1.10 (s, 3H, H25), 1.08 (s, 3H, H26), 1.04 (s, 3H, H23/24), 0.87-0.80 (m, 1H, H5), 0.82 (s, 3H, H28), 0.75 (s, 3H, H23/24)

13C-NMR (CDCl3): δ 201.7 (s, C11), 174.6 (s, C30), 172.8 (s, C13), 127.4 (d, C12), 64.4 (d, C3), 61.5 (d, C9), 55.5 (d, C5), 49.1 (d, C18), 45.5 (s, C14), 43.8 (s, C8), 43.4 (s, C20), 42.0 (t, C19), 39.7 (t, C1), 38.8 (s, C4), 38.3 (q, N-Me), 37.5 (t, C22), 36.9 (s, C10), 33.3 (t, C7), 32.6 (t, C21), 31.8 (s, C17), 28.52 (q, C23/24), 28.48 (q, C28), 26.7 (t, C16), 26.5 (t,

C15), 25.9 (q, C29), 25.7 (t, C2), 23.0 (q, C27), 18.5 (q, C26), 18.0 (t, C6), 16.5 (q, C23/24), 16.0 (q, C25)

Example 34

Compound 34

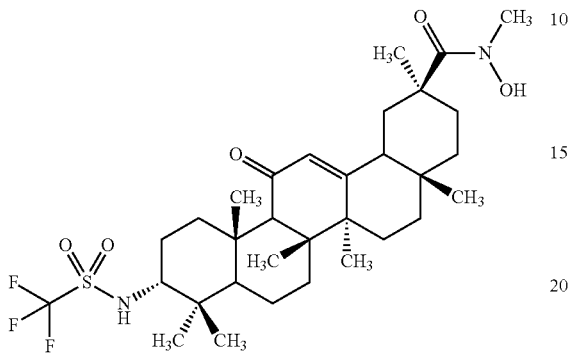

(3R,18R,20S)-N-Hydroxy-N-methyl-11-oxo-3-{(trifluoromethyl)sulfonyl]amino}-olean-12-en-29-amide ((3R,18R,20S)-11-oxo-3-{(trifluoromethyl)sulfonyl]amino}-olean-12-en-29-oic acid (150 mg, 0.25 mmol, 1.0 equiv) was stirred in a mixture of SOCl$_2$ (4 mL, 50 mmol, 200 equiv) and toluene (4 mL) at reflux temperature. After 2 h and complete conversion according to TLC (SiO$_2$, DCM:MeOH 9:1+AcOH, Hex:EtOAC 2:1) the excess SOCl$_2$ was evaporated and the residue was coevaporated from toluene twice and the residue was dissolved in dry DCM (10 mL). MeN-HOH.HCl (31 mg 0.37 mmol, 1.2 equiv) and TEA (138 µL, 1.0 mmol, 4.0 equiv) were added. The reaction mixture was stirred at RT monitored by TLC (SiO$_2$:CHCl$_3$:MeOH 9:1+ AcOH). After 1 h complete conversion was observed and solvents were evaporated, the residue was taken up in DCM and washed with 2N HCl, water, NaHCO$_3$ and brine, dried over Na$_2$SO$_4$ and evaporated. The crude material was purified by flash column chromatography (SiO$_2$: 30 g, DCM:MeOH 50:1 to 30:1) to give pure (3R,18R,20S)-N-hydroxy-N-methyl-11-oxo-3-{(trifluoromethyl)sulfonyl]amino}-olean-12-en-29-amide (0.096 g, 61.0%) as orange solid.

Optical rotation: $[\alpha]_D^{20}$=+81.9 (c=1.0 in CHCl$_3$:MeOH 3:1)

Rf-value=0.61 (CHCl$_3$:MeOH 9:1+AcOH)

1H-NMR (CDCl$_3$:MeOD 5:1): δ 5.70 (s, 1H, H12), 3.67 (s, NH/OH), 3.36-3.32 (td, 1H, J=3.1 Hz, H3), 3.25 (s, N-Me), 2.67-2.57 (m, 1H, H1a), 2.58 (s, 1H, H9), 2.31-2.03 (m, 5H, H19a, H21a, H18, H2a, H16a), 1.91-1.61 (m, 3H, H15a, H7a, H19b), 1.61-1.50 (m, 2H, H6a, H2b), 1.50-1.37 (m, 4H, H22a, H7b, H6b, H22b), 1.41 (s, 3H, H27), 1.37-1.25 (m, 1H, H21b), 1.25-1.08 (m, 2H, H15b, H1b), 1.21 (s, 3H, H29), 1.16 (s, 3H, H25), 1.13 (s, 3H, H26), 1.08-0.96 (m, 2H, H16b, H5), 0.99 (s, 3H, H23/24), 0.98 (s, 3H, H23/24), 0.82 (s, 3H, H28)

13C-NMR (CDCl$_3$:MeOD 5:1): δ 201.6 (s, C11), 175.6 (s, C30), 171.9 (s, C13), 127.6 (d, C12), 61.4 (d, C3), 61.0 (d, C9), 48.9 (d, C5), 48.5 (d, C18), 45.4 (s, C14), 44.1 (s, C8), 43.4 (s, C20), 42.1 (t, C19), 37.8 (q, N-Me), 37.7 (t, C22), 36.8 (s, C4), 36.7 (s, C10), 33.3 (t, C1), 32.3 (t, C7), 31.9 (s, C17), 31.6 (t, C21), 28.5 (q, C23/24), 28.3 (q, C28), 26.5 (t, C16), 26.3 (t, C15), 25.7 (q, C29), 23.9 (t, C2), 22.8 (q, C27), 22.7 (q, C23/24), 18.5 (q, C26), 17.1 (t, C6), 16.3 (q, C25)

Example 35

Compound 35

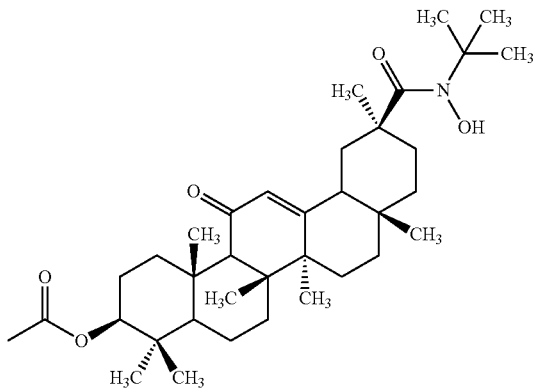

(3S,18R,20S)-3-(Acetyloxy)-N-hydroxy-N-(dimethyl ethyl)-11-oxo-olean-12-en-29-amide (3S,18R,20S)-3-(Acetyloxy)-11-oxo-olean-12-en-29-oic acid was reacted with N-(1,1-dimethylethyl)-hydroxylamine hydrochloride to (3S,18R,20S)-3-(acetyloxy)-N-hydroxy-N-(1,1-dimethylethyl)-11-oxo-olean-12-en-29-amide according to the general synthetic procedure for the preparation of the hydroxamic acids.

$^1$H NMR (200 MHz, CDCl$_3$): δ 6.95 (br, 1H), 5.92 (s, 1H), 5.20 (s, 1H), 4.32 (m, 1H), 2.91 (m, 1H), 2.37-0.72 (m, 19H), 2.01 (s, 3H), 1.33 (s, 3H), 1.18 (s, 3H), 1.14 (s, 9H), 1.12 (s, 3H), 1.09 (s, 3H), 0.84 (s, 6H), 0.77 (s, 3H).

$^{13}$C NMR (200 MHz, CDCl$_3$): δ 199.9, 176.1, 170.9, 168.8, 128.6, 8.5, 61.7, 55.7, 54.9, 48.1, 54.3, 44.0, 43.1, 4.7, 38.7, 39.0, 37.6, 36.9, 32.6, 31.8, 31.1, 28.7, 28.4, 28.0, 26.7 (3C), 26.3 (2C), 23.5, 23.3, 21.3, 18.6, 17.3, 16.6, 16.4.

Example 36

Compound 36

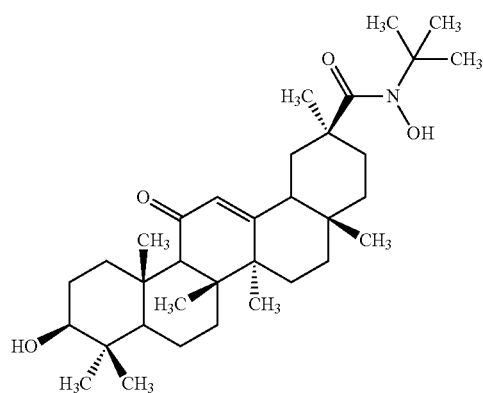

(3S,18R,20S)-3-Hydroxy-N-hydroxy-N-(dimethylethyl)-11-oxo-olean-12-en-29-amide (3S,18R,20S)-3-Acetyloxy-N-hydroxy-N-(1,1-dimethylethyl)-11-oxo-olean-12-en-29-amide was hydrolyzed to (3S,18R,20S)-3-hydroxy-N-hydroxy-N-(dimethyl-ethyl)-11-oxo-olean-12-en-29-amide according to the general procedure for deprotection of 3-acetylated hydroxamic acids $^1$H NMR (200 MHz, CDCl$_3$): δ 7.27 (s, 1H), 7.00 (br, 1H), 5.65 (s, 1H), 5.28 (s, 1H), 3.20 (m, 1H), 2.76 (m, 1H), 2.40-0.75 (m, 19H), 1.36 (s, 3H), 1.20 (s, 3H), 1.16 (s, 9H), 1.11 (s, 6H), 0.99 (s, 3H), 0.80 (s, 3H), 0.79 (s, 3H).

$^{13}$C NMR (200 MHz, CDCl$_3$): δ 200.09, 176.15, 168.78, 128.67, 78.67, 61.80, 55.77, 54.90, 48.11, 45.36, 44.01, 43.18, 40.76, 39.11, 37.67, 37.06, 32.73, 31.80, 31.08, 28.78, 28.42, 28.09, 27.28, 26.67 (3C), 26.39, 26.40, 26.35, 23.43, 18.65, 17.47, 16.33, 15.58.

Example 37

Further Compounds

The following compounds can be synthesized according to the above synthetic procedure.

(3S,18R,20S)-3-Amino-N-hydroxy-11-oxo-olean-12-en-29-amide
(3S,18R,20S)-3-(Acetamino)-N-hydroxy-11-oxo-olean-12-en-29-amide
(3S,18R,20S)-3-(Acetoxy)-N-methoxy-11-oxo-olean-12-en-29-amide
(3S,18R,20S)-3-Hydroxy-N-methoxy-11-oxo-olean-12-en-29-amide
(3S,18R,20S)-3-Amino-N-methoxy-11-oxo-olean-12-en-29-amide
(3S,18R,20S)-3-(Acetamino)-N-methoxy-11-oxo-olean-12-en-29-amide
(3S,18R,20S)-3-(Acetoxy)-N-hydroxy-N-methyl-11-oxo-olean-12-en-29-amide
(3S,18R,20S)-3-Hydroxy-N-hydroxy-N-methyl-11-oxo-olean-12-en-29-amide
(3S,18R,20S)-3-Amino-N-hydroxy-N-methyl-11-oxo-olean-12-en-29-amide
(3S,18R,20S)-3-(Acetamino)-N-hydroxy-N-methyl-11-oxo-olean-12-en-29-amide
(3S,18R,20S)-3-(Acetoxy)-N-methoxy-N-methyl-11-oxo-olean-12-en-29-amide
(3S,18R,20S)-3-Hydroxy-N-methoxy-N-methyl-11-oxo-olean-12-en-29-amide
(3S,18R,20S)-3-Amino-N-methoxy-N-methyl-11-oxo-olean-12-en-29-amide
(3S,18R,20S)-3-(Acetamino)-N-methoxy-N-methyl-11-oxo-olean-12-en-29-amide
(3S,18R,20S)-3-(Acetoxy)-N-hydroxy-olean-12-en-29-amide
(3S,18R,20S)-3-Hydroxy-N-hydroxy-olean-12-en-29-amide
(3S,18R,20S)-3-Amino-N-hydroxy-olean-12-en-29-amide
(3S,18R,20S)-3-(Acetamino)-N-hydroxy-olean-12-en-29-amide
(3S,18R,20S)-3-(Acetoxy)-N-methoxy-olean-12-en-29-amide
(3S,18R,20S)-3-Hydroxy-N-methoxy-olean-12-en-29-amide
(3S,18R,20S)-3-Amino-N-methoxy-olean-12-en-29-amide
(3S,18R,20S)-3-(Acetamino)-N-methoxy-olean-12-en-29-amide
(3S,18R,20S)-3-(Acetoxy)-N-hydroxy-N-methyl-olean-12-en-29-amide
(3S,18R,20S)-3-Hydroxy-N-hydroxy-N-methyl-olean-12-en-29-amide
(3S,18R,20S)-3-Amino-N-hydroxy-N-methyl-olean-12-en-29-amide
(3S,18R,20S)-3-(Acetamino)-N-hydroxy-N-methyl-olean-12-en-29-amide
(3S,18R,20S)-3-(Acetoxy)-N-methoxy-N-methyl-olean-12-en-29-amide
(3S,18R,20S)-3-Hydroxy-N-methoxy-N-methyl-olean-12-en-29-amide
(3S,18R,20S)-3-Amino-N-methoxy-N-methyl-olean-12-en-29-amide
(3S,18R,20S)-3-(Acetamino)-N-methoxy-N-methyl-olean-12-en-29-amide
(3S,18R,20S)-3-(Acetoxy)-N-hydroxy-11-oxo-olean-29-amide
(3S,18R,20S)-3-Hydroxy-N-hydroxy-11-oxo-olean-29-amide
(3S,18R,20S)-3-Amino-N-hydroxy-11-oxo-olean-29-amide
(3S,18R,20S)-3-(Acetamino)-N-hydroxy-11-oxo-olean-29-amide
(3S,18R,20S)-3-(Acetoxy)-N-methoxy-11-oxo-olean-29-amide
(3S,18R,20S)-3-Hydroxy-N-methoxy-11-oxo-olean-29-amide
(3S,18R,20S)-3-Amino-N-methoxy-11-oxo-olean-29-amide
(3S,18R,20S)-3-(Acetamino)-N-methoxy-11-oxo-olean-29-amide
(3S,18R,20S)-3-(Acetoxy)-N-hydroxy-N-methyl-11-oxo-olean-29-amide
(3S,18R,20S)-3-Hydroxy-N-hydroxy-N-methyl-11-oxo-olean-29-amide
(3S,18R,20S)-3-Amino-N-hydroxy-N-methyl-11-oxo-olean-29-amide
(3S,18R,20S)-3-(Acetamino)-N-hydroxy-N-methyl-11-oxo-olean-29-amide
(3S,18R,20S)-3-(Acetoxy)-N-methoxy-N-methyl-11-oxo-olean-29-amide
(3S,18R,20S)-3-Hydroxy-N-methoxy-N-methyl-11-oxo-olean-29-amide
(3S,18R,20S)-3-Amino-N-methoxy-N-methyl-11-oxo-olean-29-amide
(3S,18R,20S)-3-(Acetamino)-N-methoxy-N-methyl-11-oxo-olean-29-amide
(3S,18R,20S)-3-(Acetoxy)-N-hydroxy-olean-29-amide
(3S,18R,20S)-3-Hydroxy-N-hydroxy-olean-29-amide
(3S,18R,20S)-3-Amino-N-hydroxy-olean-29-amide
(3S,18R,20S)-3-(Acetamino)-N-hydroxy-olean-29-amide
(3S,18R,20S)-3-(Acetoxy)-N-methoxy-olean-29-amide
(3S,18R,20S)-3-Hydroxy-N-methoxy-olean-29-amide
(3S,18R,20S)-3-Amino-N-methoxy-olean-29-amide
(3S,18R,20S)-3-(Acetamino)-N-methoxy-olean-29-amide
(3S,18R,20S)-3-(Acetoxy)-N-hydroxy-N-methyl-olean-29-amide
(3S,18R,20S)-3-Hydroxy-N-hydroxy-N-methyl-olean-29-amide
(3S,18R,20S)-3-Amino-N-hydroxy-N-methyl-olean-29-amide
(3S,18R,20S)-3-(Acetamino)-N-hydroxy-N-methyl-olean-29-amide
(3S,18R,20S)-3-(Acetoxy)-N-methoxy-N-methyl-olean-29-amide
(3S,18R,20S)-3-Hydroxy-N-methoxy-N-methyl-olean-29-amide (3S,18R,20S)-3-Amino-N-methoxy-N-methyl-olean-29-amide
(3S,18R,20S)-3-(Acetamino)-N-methoxy-N-methyl-olean-29-amide
(18R,20S)-N-Hydroxy-3,11-dioxo-olean-12-en-29-amide
(18R,20S)-3-(Hydroxyimino)-N-hydroxy-11-oxo-olean-12-en-29-amide
(18R,20S)-3-Imino-N-hydroxy-11-oxo-olean-12-en-29-amide
(18R,20S)-3-(Methoxyimino)-N-hydroxy-11-oxo-olean-12-en-29-amide
(18R,20S)-N-Methoxy-3,11-dioxo-olean-12-en-29-amide
(18R,20S)-3-(Hydroxyimino)-N-methoxy-11-oxo-olean-12-en-29-amide
(18R,20S)-3-Imino-N-methoxy-11-oxo-olean-12-en-29-amide
(18R,20S)-3-(Methoxyimino)-N-methoxy-11-oxo-olean-12-en-29-amide
(18R,20S)-N-Hydroxy-N-methyl-3,11-dioxo-olean-12-en-29-amide
(18R,20S)-3-(Hydroxyimino)-N-hydroxy-N-methyl-11-oxo-olean-12-en-29-amide
(18R,20S)-3-Imino-N-hydroxy-N-methyl-11-oxo-olean-12-en-29-amide
(18R,20S)-3-(Methoxyimino)-N-hydroxy-N-methyl-11-oxo-olean-12-en-29-amide
(18R,20S)-N-Methoxy-N-methyl-3,11-dioxo-olean-12-en-29-amide
(18R,20S)-3-(Hydroxyimino)-N-methoxy-N-methyl-11-oxo-olean-12-en-29-amide
(18R,20S)-3-Imino-N-methoxy-N-methyl-11-oxo-olean-12-en-29-amide
(18R,20S)-3-(Methoxyimino)-N-methoxy-N-methyl-11-oxo-olean-12-en-29-amide
(3S,18R,20S)-3-(Succinyloxy)-N-hydroxy-11-oxo-olean-12-en-29-amide
(3S,18R,20S)-3-(Succinylamino)-N-hydroxy-11-oxo-olean-12-en-29-amide
(3S,18R,20S)-3-(Trifluoromethylsulfonamino)-N-hydroxy-11-oxo-olean-12-en-29-amide
(3S,18R,20S)-3-(Methylsulfonamino)-N-hydroxy-11-oxo-olean-12-en-29-amide
(3R,18R,20S)-3-(Acetoxy)-N-hydroxy-11-oxo-olean-12-en-29-amide
(3R,18R,20S)-3-Hydroxy-N-hydroxy-11-oxo-olean-12-en-29-amide
(3R,18R,20S)-3-Amino-N-hydroxy-11-oxo-olean-12-en-29-amide
(3R,18R,20S)-3-(Acetamino)-N-hydroxy-11-oxo-olean-12-en-29-amide
(3R,18R,20S)-3-(Succinyloxy)-N-hydroxy-11-oxo-olean-12-en-29-amide
(3R,18R,20S)-3-(Succinylamino)-N-hydroxy-11-oxo-olean-12-en-29-amide
(3R,18R,20S)-3-(Trifluoromethylsulfonamino)-N-hydroxy-11-oxo-olean-12-en-29-amide
(3R,18R,20S)-3-(Methylsulfonamino)-N-hydroxy-11-oxo-olean-12-en-29-amide
(3S,18S,20S)-3-(Acetoxy)-N-hydroxy-11-oxo-olean-12-en-29-amide
(3S,18S,20S)-3-Hydroxy-N-hydroxy-11-oxo-olean-12-en-29-amide
(3S,18S,20S)-3-Amino-N-hydroxy-11-oxo-olean-12-en-29-amide
(3S,18S,20S)-3-(Acetamino)-N-hydroxy-11-oxo-olean-12-en-29-amide
(3R,18S,20S)-3-(Acetoxy)-N-hydroxy-11-oxo-olean-12-en-29-amide
(3R,18S,20S)-3-Hydroxy-N-hydroxy-11-oxo-olean-12-en-29-amide
(3R,18S,20S)-3-Amino-N-hydroxy-11-oxo-olean-12-en-29-amide
(3R,18S,20S)-3-(Acetamino)-N-hydroxy-11-oxo-olean-12-en-29-amide
(3S,11R,18S,20S)-3-(Acetoxy)-11-hydroxy-N-hydroxy-11-oxo-olean-12-en-29-amide
(3S,11R,18S,20S)-3-Hydroxy-11-hydroxy-N-hydroxy-11-oxo-olean-12-en-29-amide
(3S,11R,18S,20S)-3-Amino-11-hydroxy-N-hydroxy-11-oxo-olean-12-en-29-amide
(3S,11R,18S,20S)-3-(Acetamino)-11-hydroxy-N-hydroxy-11-oxo-olean-12-en-29-amide
(3S,11R,18S,20S)-3-(Acetoxy)-11-amino-N-hydroxy-11-oxo-olean-12-en-29-amide
(3S,11R,18S,20S)-3-Hydroxy-11-amino-N-hydroxy-11-oxo-olean-12-en-29-amide
(3S,11R,18S,20S)-3-Amino-11-amino-N-hydroxy-11-oxo-olean-12-en-29-amide
(3S,11R,18S,20S)-3-(Acetamino)-11-amino-N-hydroxy-11-oxo-olean-12-en-29-amide
(3S,11S,18S,20S)-3-(Acetoxy)-11-hydroxy-N-hydroxy-11-oxo-olean-12-en-29-amide
(3S,11S,18S,20S)-3-Hydroxy-11-hydroxy-N-hydroxy-11-oxo-olean-12-en-29-amide
(3S,11S,18S,20S)-3-Amino-11-hydroxy-N-hydroxy-11-oxo-olean-12-en-29-amide
(3S,11S,18S,20S)-3-(Acetamino)-11-hydroxy-N-hydroxy-11-oxo-olean-12-en-29-amide
(3S,11S,18S,20S)-3-(Acetoxy)-11-amino-N-hydroxy-11-oxo-olean-12-en-29-amide
(3S,11S,18S,20S)-3-Hydroxy-11-amino-N-hydroxy-11-oxo-olean-12-en-29-amide
(3S,11S,18S,20S)-3-Amino-11-amino-N-hydroxy-11-oxo-olean-12-en-29-amide
(3S,11S,18S,20S)-3-(Acetamino)-11-amino-N-hydroxy-11-oxo-olean-12-en-29-amide
(3S,11R,18S,20S)-3-(Acetoxy)-11-hydroxy-11-methyl-N-hydroxy-11-oxo-olean-12-en-29-amide
(3S,11R,18S,20S)-3-Hydroxy-11-hydroxy-11-methyl-N-hydroxy-11-oxo-olean-12-en-29-amide
(3S,11R,18S,20S)-3-Amino-11-hydroxy-11-methyl-N-hydroxy-11-oxo-olean-12-en-29-amide
(3S,11R,18S,20S)-3-(Acetamino)-11-hydroxy-11-methyl-N-hydroxy-11-oxo-olean-12-en-29-amide
(3S,11R,18S,20S)-3-(Acetoxy)-11-amino-11-methyl-N-hydroxy-11-oxo-olean-12-en-29-amide
(3S,11R,18S,20S)-3-Hydroxy-11-amino-11-methyl-N-hydroxy-11-oxo-olean-12-en-29-amide
(3S,11R,18S,20S)-3-Amino-11-amino-11-methyl-N-hydroxy-11-oxo-olean-12-en-29-amide
(3S,11R,18S,20S)-3-(Acetamino)-11-amino-11-methyl-N-hydroxy-11-oxo-olean-12-en-29-amide
(3S,11S,18S,20S)-3-(Acetoxy)-11-hydroxy-11-methyl-N-hydroxy-11-oxo-olean-12-en-29-amide
(3S,11S,18S,20S)-3-Hydroxy-11-hydroxy-11-methyl-N-hydroxy-11-oxo-olean-12-en-29-amide
(3S,11S,18S,20S)-3-Amino-11-hydroxy-11-methyl-N-hydroxy-11-oxo-olean-12-en-29-amide
(3S,11S,18S,20S)-3-(Acetamino)-11-hydroxy-11-methyl-N-hydroxy-11-oxo-olean-12-en-29-amide
(3S,11S,18S,20S)-3-(Acetoxy)-11-amino-11-methyl-N-hydroxy-11-oxo-olean-12-en-29-amide (3S,11S,18S,20S)-3-Hydroxy-11-amino-11-methyl-N-hydroxy-11-oxo-olean-12-en-29-amide
(3S,11S,18S,20S)-3-Amino-11-amino-11-methyl-N-hydroxy-11-oxo-olean-12-en-29-amide
(3S,11S,18S,20S)-3-(Acetamino)-11-amino-11-methyl-N-hydroxy-11-oxo-olean-12-en-29-amide
(3S,11R,18S,20S)-3-(Acetoxy)-11-hydroxy-11-ethynyl-N-hydroxy-11-oxo-olean-12-en-29-amide
(3S,11R,18S,20S)-3-Hydroxy-11-hydroxy-11-ethynyl-N-hydroxy-11-oxo-olean-12-en-29-amide
(3S,11R,18S,20S)-3-Amino-11-hydroxy-11-ethynyl-N-hydroxy-11-oxo-olean-12-en-29-amide
(3S,11R,18S,20S)-3-(Acetamino)-11-hydroxy-11-ethynyl-N-hydroxy-11-oxo-olean-12-en-29-amide
(3S,11R,18S,20S)-3-(Acetoxy)-11-amino-11-ethynyl-N-hydroxy-11-oxo-olean-12-en-29-amide
(3S,11R,18S,20S)-3-Hydroxy-11-amino-11-ethynyl-N-hydroxy-11-oxo-olean-12-en-29-amide
(3S,11R,18S,20S)-3-Amino-11-amino-11-ethynyl-N-hydroxy-11-oxo-olean-12-en-29-amide
(3S,11R,18S,20S)-3-(Acetamino)-11-amino-11-ethynyl-N-hydroxy-11-oxo-olean-12-en-29-amide
(3S,11S,18S,20S)-3-(Acetoxy)-11-hydroxy-11-ethynyl-N-hydroxy-11-oxo-olean-12-en-29-amide
(3S,11S,18S,20S)-3-Hydroxy-11-hydroxy-11-ethynyl-N-hydroxy-11-oxo-olean-12-en-29-amide
(3S,11S,18S,20S)-3-Amino-11-hydroxy-11-ethynyl-N-hydroxy-11-oxo-olean-12-en-29-amide
(3S,11S,18S,20S)-3-(Acetamino)-11-hydroxy-11-ethynyl-N-hydroxy-11-oxo-olean-12-en-29-amide
(3S,11S,18S,20S)-3-(Acetoxy)-11-amino-11-ethynyl-N-hydroxy-11-oxo-olean-12-en-29-amide
(3S,11S,18S,20S)-3-Hydroxy-11-amino-11-ethynyl-N-hydroxy-11-oxo-olean-12-en-29-amide
(3S,11S,18S,20S)-3-Amino-11-amino-11-ethynyl-N-hydroxy-11-oxo-olean-12-en-29-amide
(3S,11S,18S,20S)-3-(Acetamino)-11-amino-11-ethynyl-N-hydroxy-11-oxo-olean-12-en-29-amide
(3S,18R,20S)-3-(Succinyloxy)-N-methoxy-11-oxo-olean-12-en-29-amide
(3S,18R,20S)-3-(Succinylamino)-N-methoxy-11-oxo-olean-12-en-29-amide
(3S,18R,20S)-3-(Trifluoromethylsulfonamino)-N-methoxy-11-oxo-olean-12-en-29-amide
(3S,18R,20S)-3-(Methylsulfonamino)-N-methoxy-11-oxo-olean-12-en-29-amide
(3R,18R,20S)-3-(Acetoxy)-N-methoxy-11-oxo-olean-12-en-29-amide
(3R,18R,20S)-3-Hydroxy-N-methoxy-11-oxo-olean-12-en-29-amide
(3R,18R,20S)-3-Amino-N-methoxy-11-oxo-olean-12-en-29-amide
(3R,18R,20S)-3-(Acetamino)-N-methoxy-11-oxo-olean-12-en-29-amide
(3R,18R,20S)-3-(Succinyloxy)-N-methoxy-11-oxo-olean-12-en-29-amide
(3R,18R,20S)-3-(Succinylamino)-N-methoxy-11-oxo-olean-12-en-29-amide
(3R,18R,20S)-3-(Trifluoromethylsulfonamino)-N-methoxy-11-oxo-olean-12-en-29-amide
(3R,18R,20S)-3-(Methylsulfonamino)-N-methoxy-11-oxo-olean-12-en-29-amide
(3S,18S,20S)-3-(Acetoxy)-N-methoxy-11-oxo-olean-12-en-29-amide
(3S,18S,20S)-3-Hydroxy-N-methoxy-11-oxo-olean-12-en-29-amide
(3S,18S,20S)-3-Amino-N-methoxy-11-oxo-olean-12-en-29-amide
(3S,18S,20S)-3-(Acetamino)-N-methoxy-11-oxo-olean-12-en-29-amide
(3R,18S,20S)-3-(Acetoxy)-N-methoxy-11-oxo-olean-12-en-29-amide
(3R,18S,20S)-3-Hydroxy-N-methoxy-11-oxo-olean-12-en-29-amide
(3R,18S,20S)-3-Amino-N-methoxy-11-oxo-olean-12-en-29-amide
(3R,18S,20S)-3-(Acetamino)-N-methoxy-11-oxo-olean-12-en-29-amide
(3S,11R,18S,20S)-3-(Acetoxy)-11-hydroxy-N-methoxy-11-oxo-olean-12-en-29-amide
(3S,11R,18S,20S)-3-Hydroxy-11-hydroxy-N-methoxy-11-oxo-olean-12-en-29-amide
(3S,11R,18S,20S)-3-Amino-11-hydroxy-N-methoxy-11-oxo-olean-12-en-29-amide
(3S,11R,18S,20S)-3-(Acetamino)-11-hydroxy-N-methoxy-11-oxo-olean-12-en-29-amide
(3S,11R,18S,20S)-3-(Acetoxy)-11-amino-N-methoxy-11-oxo-olean-12-en-29-amide
(3S,11R,18S,20S)-3-Hydroxy-11-amino-N-methoxy-11-oxo-olean-12-en-29-amide
(3S,11R,18S,20S)-3-Amino-11-amino-N-methoxy-11-oxo-olean-12-en-29-amide
(3S,11R,18S,20S)-3-(Acetamino)-11-amino-N-methoxy-11-oxo-olean-12-en-29-amide
(3S,11S,18S,20S)-3-(Acetoxy)-11-hydroxy-N-methoxy-11-oxo-olean-12-en-29-amide
(3S,11S,18S,20S)-3-Hydroxy-11-hydroxy-N-methoxy-11-oxo-olean-12-en-29-amide
(3S,11S,18S,20S)-3-Amino-11-hydroxy-N-methoxy-11-oxo-olean-12-en-29-amide
(3S,11S,18S,20S)-3-(Acetamino)-11-hydroxy-N-methoxy-11-oxo-olean-12-en-29-amide
(3S,11S,18S,20S)-3-(Acetoxy)-11-amino-N-methoxy-11-oxo-olean-12-en-29-amide
(3S,11S,18S,20S)-3-Hydroxy-11-amino-N-methoxy-11-oxo-olean-12-en-29-amide
(3S,11S,18S,20S)-3-Amino-11-amino-N-methoxy-11-oxo-olean-12-en-29-amide
(3S,11S,18S,20S)-3-(Acetamino)-11-amino-N-methoxy-11-oxo-olean-12-en-29-amide
(3S,11R,18S,20S)-3-(Acetoxy)-11-hydroxy-11-methyl-N-methoxy-11-oxo-olean-12-en-29-amide
(3S,11R,18S,20S)-3-Hydroxy-11-hydroxy-11-methyl-N-methoxy-11-oxo-olean-12-en-29-amide
(3S,11R,18S,20S)-3-Amino-11-hydroxy-11-methyl-N-methoxy-11-oxo-olean-12-en-29-amide
(3S,11R,18S,20S)-3-(Acetamino)-11-hydroxy-11-methyl-N-methoxy-11-oxo-olean-12-en-29-amide
(3S,11R,18S,20S)-3-(Acetoxy)-11-amino-11-methyl-N-methoxy-11-oxo-olean-12-en-29-amide
(3S,11R,18S,20S)-3-Hydroxy-11-amino-11-methyl-N-methoxy-11-oxo-olean-12-en-29-amide
(3S,11R,18S,20S)-3-Amino-11-amino-11-methyl-N-methoxy-11-oxo-olean-12-en-29-amide
(3S,11R,18S,20S)-3-(Acetamino)-11-amino-11-methyl-N-methoxy-11-oxo-olean-12-en-29-amide
(3S,11S,18S,20S)-3-(Acetoxy)-11-hydroxy-11-methyl-N-methoxy-11-oxo-olean-12-en-29-amide
(3S,11S,18S,20S)-3-Hydroxy-11-hydroxy-11-methyl-N-methoxy-11-oxo-olean-12-en-29-amide
(3S,11S,18S,20S)-3-Amino-11-hydroxy-11-methyl-N-methoxy-11-oxo-olean-12-en-29-amide (3S,11S,18S,20S)-3-(Acetamino)-11-hydroxy-11-methyl-N-methoxy-11-oxo-olean-12-en-29-amide
(3S,11S,18S,20S)-3-(Acetoxy)-11-amino-11-methyl-N-methoxy-11-oxo-olean-12-en-29-amide
(3S,11S,18S,20S)-3-Hydroxy-11-amino-11-methyl-N-methoxy-11-oxo-olean-12-en-29-amide
(3S,11S,18S,20S)-3-Amino-11-amino-11-methyl-N-methoxy-11-oxo-olean-12-en-29-amide
(3S,11S,18S,20S)-3-(Acetamino)-11-amino-11-methyl-N-methoxy-11-oxo-olean-12-en-29-amide
(3S,11R,18S,20S)-3-(Acetoxy)-11-hydroxy-11-ethynyl-N-methoxy-11-oxo-olean-12-en-29-amide
(3S,11R,18S,20S)-3-Hydroxy-11-hydroxy-11-ethynyl-N-methoxy-11-oxo-olean-12-en-29-amide
(3S,11R,18S,20S)-3-Amino-11-hydroxy-11-ethynyl-N-methoxy-11-oxo-olean-12-en-29-amide
(3S,11R,18S,20S)-3-(Acetamino)-11-hydroxy-11-ethynyl-N-methoxy-11-oxo-olean-12-en-29-amide
(3S,11R,18S,20S)-3-(Acetoxy)-11-amino-11-ethynyl-N-methoxy-11-oxo-olean-12-en-29-amide
(3S,11R,18S,20S)-3-Hydroxy-11-amino-11-ethynyl-N-methoxy-11-oxo-olean-12-en-29-amide
(3S,11R,18S,20S)-3-Amino-11-amino-11-ethynyl-N-methoxy-11-oxo-olean-12-en-29-amide
(3S,11R,18S,20S)-3-(Acetamino)-11-amino-11-ethynyl-N-methoxy-11-oxo-olean-12-en-29-amide
(3S,11S,18S,20S)-3-(Acetoxy)-11-hydroxy-11-ethynyl-N-methoxy-11-oxo-olean-12-en-29-amide
(3S,11S,18S,20S)-3-Hydroxy-11-hydroxy-11-ethynyl-N-methoxy-11-oxo-olean-12-en-29-amide
(3S,11S,18S,20S)-3-Amino-11-hydroxy-11-ethynyl-N-methoxy-11-oxo-olean-12-en-29-amide
(3S,11S,18S,20S)-3-(Acetamino)-11-hydroxy-11-ethynyl-N-methoxy-11-oxo-olean-12-en-29-amide
(3S,11S,18S,20S)-3-(Acetoxy)-11-amino-11-ethynyl-N-methoxy-11-oxo-olean-12-en-29-amide
(3S,11S,18S,20S)-3-Hydroxy-11-amino-11-ethynyl-N-methoxy-11-oxo-olean-12-en-29-amide
(3S,11S,18S,20S)-3-Amino-11-amino-11-ethynyl-N-methoxy-11-oxo-olean-12-en-29-amide
(3S,11S,18S,20S)-3-(Acetamino)-11-amino-11-ethynyl-N-methoxy-11-oxo-olean-12-en-29-amide
(3S,18R,20S)-3-(Succinyloxy)-N-hydroxy-N-methyl-11-oxo-olean-12-en-29-amide
(3S,18R,20S)-3-(Succinylamino)-N-hydroxy-N-methyl-11-oxo-olean-12-en-29-amide
(3S,18R,20S)-3-(Trifluoromethylsulfonamino)-N-hydroxy-N-methoxy-11-oxo-olean-12-en-29-amide
(3S,18R,20S)-3-(Methylsulfonamino)-N-hydroxy-N-methyl-11-oxo-olean-12-en-29-amide
(3R,18R,20S)-3-(Acetoxy)-N-hydroxy-N-methyl-11-oxo-olean-12-en-29-amide
(3R,18R,20S)-3-Hydroxy-N-hydroxy-N-methyl-11-oxo-olean-12-en-29-amide
(3R,18R,20S)-3-Amino-N-hydroxy-N-methyl-11-oxo-olean-12-en-29-amide
(3R,18R,20S)-3-(Acetamino)-N-hydroxy-N-methyl-11-oxo-olean-12-en-29-amide
(3R,18R,20S)-3-(Succinyloxy)-N-hydroxy-N-methyl-11-oxo-olean-12-en-29-amide
(3R,18R,20S)-3-(Succinylamino)-N-hydroxy-N-methyl-11-oxo-olean-12-en-29-amide
(3R,18R,20S)-3-(Trifluoromethylsulfonamino)-N-hydroxy-N-methyl-11-oxo-olean-12-en-29-amide
(3R,18R,20S)-3-(Methylsulfonamino)-N-hydroxy-N-methyl-11-oxo-olean-12-en-29-amide
(3S,18S,20S)-3-(Acetoxy)-N-hydroxy-N-methyl-11-oxo-olean-12-en-29-amide
(3S,18S,20S)-3-Hydroxy-N-hydroxy-N-methyl-11-oxo-olean-12-en-29-amide
(3S,18S,20S)-3-Amino-N-hydroxy-N-methyl-11-oxo-olean-12-en-29-amide
(3S,18S,20S)-3-(Acetamino)-N-hydroxy-N-methyl-11-oxo-olean-12-en-29-amide
(3R,18S,20S)-3-(Acetoxy)-N-hydroxy-N-methyl-11-oxo-olean-12-en-29-amide
(3R,18S,20S)-3-Hydroxy-N-hydroxy-N-methyl-11-oxo-olean-12-en-29-amide
(3R,18S,20S)-3-Amino-N-hydroxy-N-methyl-11-oxo-olean-12-en-29-amide
(3R,18S,20S)-3-(Acetamino)-N-hydroxy-N-methyl-11-oxo-olean-12-en-29-amide
(3S,11R,18S,20S)-3-(Acetoxy)-11-hydroxy-N-hydroxy-N-methyl-11-oxo-olean-12-en-29-amide
(3S,11R,18S,20S)-3-Hydroxy-11-hydroxy-N-hydroxy-N-methyl-11-oxo-olean-12-en-29-amide
(3S,11R,18S,20S)-3-Amino-11-hydroxy-N-hydroxy-N-methyl-11-oxo-olean-12-en-29-amide
(3S,11R,18S,20S)-3-(Acetamino)-11-hydroxy-N-hydroxy-N-methyl-11-oxo-olean-12-en-29-amide
(3S,11R,18S,20S)-3-(Acetoxy)-11-amino-N-hydroxy-N-methyl-11-oxo-olean-12-en-29-amide
(3S,11R,18S,20S)-3-Hydroxy-11-amino-N-hydroxy-N-methyl-11-oxo-olean-12-en-29-amide
(3S,11R,18S,20S)-3-Amino-11-amino-N-hydroxy-N-methyl-11-oxo-olean-12-en-29-amide
(3S,11R,18S,20S)-3-(Acetamino)-11-amino-N-hydroxy-N-methyl-11-oxo-olean-12-en-29-amide
(3S,11S,18S,20S)-3-(Acetoxy)-11-hydroxy-N-hydroxy-N-methyl-11-oxo-olean-12-en-29-amide
(3S,11S,18S,20S)-3-Hydroxy-11-hydroxy-N-hydroxy-N-methyl-11-oxo-olean-12-en-29-amide
(3S,11S,18S,20S)-3-Amino-11-hydroxy-N-hydroxy-N-methyl-11-oxo-olean-12-en-29-amide
(3S,11S,18S,20S)-3-(Acetamino)-11-hydroxy-N-hydroxy-N-methyl-11-oxo-olean-12-en-29-amide
(3S,11S,18S,20S)-3-(Acetoxy)-11-amino-N-hydroxy-N-methyl-11-oxo-olean-12-en-29-amide
(3S,11S,18S,20S)-3-Hydroxy-11-amino-N-hydroxy-N-methyl-11-oxo-olean-12-en-29-amide
(3S,11S,18S,20S)-3-Amino-11-amino-N-hydroxy-N-methyl-11-oxo-olean-12-en-29-amide
(3S,11S,18S,20S)-3-(Acetamino)-11-amino-N-hydroxy-N-methyl-11-oxo-olean-12-en-29-amide
(3S,11R,18S,20S)-3-(Acetoxy)-11-hydroxy-11-methyl-N-hydroxy-N-methyl-11-oxo-olean-12-en-29-amide
(3S,11R,18S,20S)-3-Hydroxy-11-hydroxy-11-methyl-N-hydroxy-N-methyl-11-oxo-olean-12-en-29-amide
(3S,11R,18S,20S)-3-Amino-11-hydroxy-11-methyl-N-hydroxy-N-methyl-11-oxo-olean-12-en-29-amide
(3S,11R,18S,20S)-3-(Acetamino)-11-hydroxy-11-methyl-N-hydroxy-N-methyl-11-oxo-olean-12-en-29-amide
(3S,11R,18S,20S)-3-(Acetoxy)-11-amino-11-methyl-N-hydroxy-N-methyl-11-oxo-olean-12-en-29-amide
(3S,11R,18S,20S)-3-Hydroxy-11-amino-11-methyl-N-hydroxy-N-methyl-11-oxo-olean-12-en-29-amide
(3S,11R,18S,20S)-3-Amino-11-amino-11-methyl-N-hydroxy-N-methyl-11-oxo-olean-12-en-29-amide
(3S,11R,18S,20S)-3-(Acetamino)-11-amino-11-methyl-N-hydroxy-N-methyl-11-oxo-olean-12-en-29-amide
(3S,11S,18S,20S)-3-(Acetoxy)-11-hydroxy-11-methyl-N-hydroxy-N-methyl-11-oxo-olean-12-en-29-amide (3S,11S,18S,20S)-3-Hydroxy-11-hydroxy-11-methyl-N-hydroxy-N-methyl-11-oxo-olean-12-en-29-amide
(3S,11S,18S,20S)-3-Amino-11-hydroxy-11-methyl-N-hydroxy-N-methyl-11-oxo-olean-12-en-29-amide
(3S,11S,18S,20S)-3-(Acetamino)-11-hydroxy-11-methyl-N-hydroxy-N-methyl-11-oxo-olean-12-en-29-amide
(3S,11S,18S,20S)-3-(Acetoxy)-11-amino-11-methyl-N-hydroxy-N-methyl-11-oxo-olean-12-en-29-amide
(3S,11S,18S,20S)-3-Hydroxy-11-amino-11-methyl-N-hydroxy-N-methyl-11-oxo-olean-12-en-29-amide
(3S,11S,18S,20S)-3-Amino-11-amino-11-methyl-N-hydroxy-N-methyl-11-oxo-olean-12-en-29-amide
(3S,11S,18S,20S)-3-(Acetamino)-11-amino-11-methyl-N-hydroxy-N-methyl-11-oxo-olean-12-en-29-amide
(3S,11R,18S,20S)-3-(Acetoxy)-11-hydroxy-11-ethynyl-N-hydroxy-N-methyl-11-oxo-olean-12-en-29-amide
(3S,11R,18S,20S)-3-Hydroxy-11-hydroxy-11-ethynyl-N-hydroxy-N-methyl-11-oxo-olean-12-en-29-amide
(3S,11R,18S,20S)-3-Amino-11-hydroxy-11-ethynyl-N-hydroxy-N-methyl-11-oxo-olean-12-en-29-amide
(3S,11R,18S,20S)-3-(Acetamino)-11-hydroxy-11-ethynyl-N-hydroxy-N-methyl-11-oxo-olean-12-en-29-amide
(3S,11R,18S,20S)-3-(Acetoxy)-11-amino-11-ethynyl-N-hydroxy-N-methyl-11-oxo-olean-12-en-29-amide
(3S,11R,18S,20S)-3-Hydroxy-11-amino-11-ethynyl-N-hydroxy-N-methyl-11-oxo-olean-12-en-29-amide
(3S,11R,18S,20S)-3-Amino-11-amino-11-ethynyl-N-hydroxy-N-methyl-11-oxo-olean-12-en-29-amide
(3S,11R,18S,20S)-3-(Acetamino)-11-amino-11-ethynyl-N-hydroxy-N-methyl-11-oxo-olean-12-en-29-amide
(3S,11S,18S,20S)-3-(Acetoxy)-11-hydroxy-11-ethynyl-N-hydroxy-N-methyl-11-oxo-olean-12-en-29-amide
(3S,11S,18S,20S)-3-Hydroxy-11-hydroxy-11-ethynyl-N-hydroxy-N-methyl-11-oxo-olean-12-en-29-amide
(3S,11S,18S,20S)-3-Amino-11-hydroxy-11-ethynyl-N-hydroxy-N-methyl-11-oxo-olean-12-en-29-amide
(3S,11S,18S,20S)-3-(Acetamino)-11-hydroxy-11-ethynyl-N-hydroxy-N-methyl-11-oxo-olean-12-en-29-amide
(3S,11S,18S,20S)-3-(Acetoxy)-11-amino-11-ethynyl-N-hydroxy-N-methyl-11-oxo-olean-12-en-29-amide
(3S,11S,18S,20S)-3-Hydroxy-11-amino-11-ethynyl-N-hydroxy-N-methyl-11-oxo-olean-12-en-29-amide
(3S,11S,18S,20S)-3-Amino-11-amino-11-ethynyl-N-hydroxy-N-methyl-11-oxo-olean-12-en-29-amide
(3S,11S,18S,20S)-3-(Acetamino)-11-amino-11-ethynyl-N-hydroxy-N-methyl-11-oxo-olean-12-en-29-amide
(3S,18R,20S)-3-(Succinyloxy)-N-methoxy-N-methyl-11-oxo-olean-12-en-29-amide
(3S,18R,20S)-3-(Succinylamino)-N-methoxy-N-methyl-11-oxo-olean-12-en-29-amide
(3S,18R,20S)-3-(Trifluoromethylsulfonamino)-N-methoxy-N-methyl-11-oxo-olean-12-en-29-amide
(3S,18R,20S)-3-(Methylsulfonamino)-N-methoxy-N-methyl-11-oxo-olean-12-en-29-amide
(3R,18R,20S)-3-(Acetoxy)-N-methoxy-N-methyl-11-oxo-olean-12-en-29-amide
(3R,18R,20S)-3-Hydroxy-N-methoxy-N-methyl-11-oxo-olean-12-en-29-amide
(3R,18R,20S)-3-Amino-N-methoxy-N-methyl-11-oxo-olean-12-en-29-amide
(3R,18R,20S)-3-(Acetamino)-N-methoxy-N-methyl-11-oxo-olean-12-en-29-amide
(3R,18R,20S)-3-(Succinyloxy)-N-methoxy-N-methyl-11-oxo-olean-12-en-29-amide
(3R,18R,20S)-3-(Succinylamino)-N-methoxy-N-methyl-11-oxo-olean-12-en-29-amide
(3R,18R,20S)-3-(Trifluoromethylsulfonamino)-N-methoxy-N-methyl-11-oxo-olean-12-en-29-amide
(3R,18R,20S)-3-(Methylsulfonamino)-N-methoxy-N-methyl-11-oxo-olean-12-en-29-amide
(3S,18S,20S)-3-(Acetoxy)-N-methoxy-N-methyl-11-oxo-olean-12-en-29-amide
(3S,18S,20S)-3-Hydroxy-N-methoxy-N-methyl-11-oxo-olean-12-en-29-amide
(3S,18S,20S)-3-Amino-N-methoxy-N-methyl-11-oxo-olean-12-en-29-amide
(3S,18S,20S)-3-(Acetamino)-N-methoxy-N-methyl-11-oxo-olean-12-en-29-amide
(3R,18S,20S)-3-(Acetoxy)-N-methoxy-N-methyl-11-oxo-olean-12-en-29-amide
(3R,18S,20S)-3-Hydroxy-N-methoxy-N-methyl-11-oxo-olean-12-en-29-amide
(3R,18S,20S)-3-Amino-N-methoxy-N-methyl-11-oxo-olean-12-en-29-amide
(3R,18S,20S)-3-(Acetamino)-N-methoxy-N-methyl-11-oxo-olean-12-en-29-amide
(3S,11R,18S,20S)-3-(Acetoxy)-11-hydroxy-N-methoxy-N-methyl-11-oxo-olean-12-en-29-amide
(3S,11R,18S,20S)-3-Hydroxy-11-hydroxy-N-methoxy-N-methyl-11-oxo-olean-12-en-29-amide
(3S,11R,18S,20S)-3-Amino-11-hydroxy-N-methoxy-N-methyl-11-oxo-olean-12-en-29-amide
(3S,11R,18S,20S)-3-(Acetamino)-11-hydroxy-N-methoxy-N-methyl-11-oxo-olean-12-en-29-amide
(3S,11R,18S,20S)-3-(Acetoxy)-11-amino-N-methoxy-N-methyl-11-oxo-olean-12-en-29-amide
(3S,11R,18S,20S)-3-Hydroxy-11-amino-N-methoxy-N-methyl-11-oxo-olean-12-en-29-amide
(3S,11R,18S,20S)-3-Amino-11-amino-N-methoxy-N-methyl-11-oxo-olean-12-en-29-amide
(3S,11R,18S,20S)-3-(Acetamino)-11-amino-N-methoxy-N-methyl-11-oxo-olean-12-en-29-amide
(3S,11S,18S,20S)-3-(Acetoxy)-11-hydroxy-N-methoxy-N-methyl-11-oxo-olean-12-en-29-amide
(3S,11S,18S,20S)-3-Hydroxy-11-hydroxy-N-methoxy-N-methyl-11-oxo-olean-12-en-29-amide
(3S,11S,18S,20S)-3-Amino-11-hydroxy-N-methoxy-N-methyl-11-oxo-olean-12-en-29-amide
(3S,11S,18S,20S)-3-(Acetamino)-11-hydroxy-N-methoxy-N-methyl-11-oxo-olean-12-en-29-amide
(3S,11S,18S,20S)-3-(Acetoxy)-11-amino-N-methoxy-N-methyl-11-oxo-olean-12-en-29-amide
(3S,11S,18S,20S)-3-Hydroxy-11-amino-N-methoxy-N-methyl-11-oxo-olean-12-en-29-amide
(3S,11S,18S,20S)-3-Amino-11-amino-N-methoxy-N-methyl-11-oxo-olean-12-en-29-amide
(3S,11S,18S,20S)-3-(Acetamino)-11-amino-N-methoxy-N-methyl-11-oxo-olean-12-en-29-amide
(3S,11R,18S,20S)-3-(Acetoxy)-11-hydroxy-11-methyl-N-methoxy-N-methyl-11-oxo-olean-12-en-29-amide
(3S,11R,18S,20S)-3-Hydroxy-11-hydroxy-11-methyl-N-methoxy-N-methyl-11-oxo-olean-12-en-29-amide
(3S,11R,18S,20S)-3-Amino-11-hydroxy-11-methyl-N-methoxy-N-methyl-11-oxo-olean-12-en-29-amide
(3S,11R,18S,20S)-3-(Acetamino)-11-hydroxy-11-methyl-N-methoxy-N-methyl-11-oxo-olean-12-en-29-amide
(3S,11R,18S,20S)-3-(Acetoxy)-11-amino-11-methyl-N-methoxy-N-methyl-11-oxo-olean-12-en-29-amide
(3S,11R,18S,20S)-3-Hydroxy-11-amino-11-methyl-N-methoxy-N-methyl-11-oxo-olean-12-en-29-amide
(3S,11R,18S,20S)-3-Amino-11-amino-11-methyl-N-methoxy-N-methyl-11-oxo-olean-12-en-29-amide (3S,11R,18S,20S)-3-(Acetamino)-11-amino-11-methyl-N-methoxy-N-methyl-11-oxo-olean-12-en-29-amide
(3S,11S,18S,20S)-3-(Acetoxy)-11-hydroxy-11-methyl-N-methoxy-N-methyl-11-oxo-olean-12-en-29-amide
(3S,11S,18S,20S)-3-Hydroxy-11-hydroxy-11-methyl-N-methoxy-N-methyl-11-oxo-olean-12-en-29-amide
(3S,11S,18S,20S)-3-Amino-11-hydroxy-11-methyl-N-methoxy-N-methyl-11-oxo-olean-12-en-29-amide
(3S,11S,18S,20S)-3-(Acetamino)-11-hydroxy-11-methyl-N-methoxy-N-methyl-11-oxo-olean-12-en-29-amide
(3S,11S,18S,20S)-3-(Acetoxy)-11-amino-11-methyl-N-methoxy-N-methyl-11-oxo-olean-12-en-29-amide
(3S,11S,18S,20S)-3-Hydroxy-11-amino-11-methyl-N-methoxy-N-methyl-11-oxo-olean-12-en-29-amide
(3S,11S,18S,20S)-3-Amino-11-amino-11-methyl-N-methoxy-N-methyl-11-oxo-olean-12-en-29-amide
(3S,11S,18S,20S)-3-(Acetamino)-11-amino-11-methyl-N-methoxy-N-methyl-11-oxo-olean-12-en-29-amide
(3S,11R,18S,20S)-3-(Acetoxy)-11-hydroxy-11-ethynyl-N-methoxy-N-methyl-11-oxo-olean-12-en-29-amide
(3S,11R,18S,20S)-3-Hydroxy-11-hydroxy-11-ethynyl-N-methoxy-N-methyl-11-oxo-olean-12-en-29-amide
(3S,11R,18S,20S)-3-Amino-11-hydroxy-11-ethynyl-N-methoxy-N-methyl-11-oxo-olean-12-en-29-amide
(3S,11R,18S,20S)-3-(Acetamino)-11-hydroxy-11-ethynyl-N-methoxy-N-methyl-11-oxo-olean-12-en-29-amide
(3S,11R,18S,20S)-3-(Acetoxy)-11-amino-11-ethynyl-N-methoxy-N-methyl-11-oxo-olean-12-en-29-amide
(3S,11R,18S,20S)-3-Hydroxy-11-amino-11-ethynyl-N-methoxy-N-methyl-11-oxo-olean-12-en-29-amide
(3S,11R,18S,20S)-3-Amino-11-amino-11-ethynyl-N-methoxy-N-methyl-11-oxo-olean-12-en-29-amide
(3S,11R,18S,20S)-3-(Acetamino)-11-amino-11-ethynyl-N-methoxy-N-methyl-11-oxo-olean-12-en-29-amide
(3S,11S,18S,20S)-3-(Acetoxy)-11-hydroxy-11-ethynyl-N-methoxy-N-methyl-11-oxo-olean-12-en-29-amide
(3S,11S,18S,20S)-3-Hydroxy-11-hydroxy-11-ethynyl-N-methoxy-N-methyl-11-oxo-olean-12-en-29-amide
(3S,11S,18S,20S)-3-Amino-11-hydroxy-11-ethynyl-N-methoxy-N-methyl-11-oxo-olean-12-en-29-amide
(3S,11S,18S,20S)-3-(Acetamino)-11-hydroxy-11-ethynyl-N-methoxy-N-methyl-11-oxo-olean-12-en-29-amide
(3S,11S,18S,20S)-3-(Acetoxy)-11-amino-11-ethynyl-N-methoxy-N-methyl-11-oxo-olean-12-en-29-amide
(3S,11S,18S,20S)-3-Hydroxy-11-amino-11-ethynyl-N-methoxy-N-methyl-11-oxo-olean-12-en-29-amide
(3S,11S,18S,20S)-3-Amino-11-amino-11-ethynyl-N-methoxy-N-methyl-11-oxo-olean-12-en-29-amide
(3S,11S,18S,20S)-3-(Acetamino)-11-amino-11-ethynyl-N-methoxy-N-methyl-11-oxo-olean-12-en-29-amide
(3S,18R,20S)-3-(Acetoxy)-N-ethoxy-11-oxo-olean-12-en-29-amide
(3S,18R,20S)-3-(Acetoxy)-N-i-propyloxy-11-oxo-olean-12-en-29-amide
(3S,18R,20S)-3-(Acetoxy)-N-t-butyloxy-11-oxo-olean-12-en-29-amide
(3S,18R,20S)-3-(Acetoxy)-N-allyloxy-11-oxo-olean-12-en-29-amide
(3S,18R,20S)-3-(Acetoxy)-N-ethynyloxy-11-oxo-olean-12-en-29-amide
(3S,18R,20S)-3-(Acetoxy)-N-cyclopropyloxy-11-oxo-olean-12-en-29-amide
(3S,18R,20S)-3-(Acetoxy)-N-cyclobutyloxy-11-oxo-olean-12-en-29-amide
(3S,18R,20S)-3-(Acetoxy)-N-trifluoromethoxy-11-oxo-olean-12-en-29-amide
(3S,18R,20S)-3-(Acetoxy)-N-(phenylmethoxy)-11-oxo-olean-12-en-29-amide
(3S,18R,20S)-3-(Acetoxy)-N-phenoxy-11-oxo-olean-12-en-29-amide
(3S,18R,20S)-3-(Acetoxy)-N-ethoxy-N-methyl-11-oxo-olean-12-en-29-amide
(3S,18R,20S)-3-(Acetoxy)-N-i-propyloxy-N-methyl-11-oxo-olean-12-en-29-amide
(3S,18R,20S)-3-(Acetoxy)-N-t-butyloxy-N-methyl-11-oxo-olean-12-en-29-amide
(3S,18R,20S)-3-(Acetoxy)-N-allyloxy-N-methyl-11-oxo-olean-12-en-29-amide
(3S,18R,20S)-3-(Acetoxy)-N-ethynyloxy-N-methyl-11-oxo-olean-12-en-29-amide
(3S,18R,20S)-3-(Acetoxy)-N-cyclopropyloxy-N-methyl-11-oxo-olean-12-en-29-amide
(3S,18R,20S)-3-(Acetoxy)-N-cyclobutyloxy-N-methyl-11-oxo-olean-12-en-29-amide
(3S,18R,20S)-3-(Acetoxy)-N-trifluoromethoxy-N-methyl-11-oxo-olean-12-en-29-amide
(3S,18R,20S)-3-(Acetoxy)-N-(phenylmethoxy)-N-methyl-11-oxo-olean-12-en-29-amide
(3S,18R,20S)-3-(Acetoxy)-N-phenoxy-N-methyl-11-oxo-olean-12-en-29-amide
(3S,18R,20S)-3-(Acetoxy)-N-hydroxy-N-ethyl-11-oxo-olean-12-en-29-amide
(3S,18R,20S)-3-(Acetoxy)-N-hydroxy-N-i-propyl-11-oxo-olean-12-en-29-amide
(3S,18R,20S)-3-(Acetoxy)-N-hydroxy-N-t-butyl-11-oxo-olean-12-en-29-amide
(3S,18R,20S)-3-(Acetoxy)-N-hydroxy-N-allyl-11-oxo-olean-12-en-29-amide
(3S,18R,20S)-3-(Acetoxy)-N-hydroxy-N-ethynyl-11-oxo-olean-12-en-29-amide
(3S,18R,20S)-3-(Acetoxy)-N-hydroxy-N-cyclopropyl-11-oxo-olean-12-en-29-amide
(3S,18R,20S)-3-(Acetoxy)-N-hydroxy-N-cyclobutyl-11-oxo-olean-12-en-29-amide
(3S,18R,20S)-3-(Acetoxy)-N-hydroxy-N-trifluoromethyl-11-oxo-olean-12-en-29-amide
(3S,18R,20S)-3-(Acetoxy)-N-hydroxy-N-2-hydroxyethyl-11-oxo-olean-12-en-29-amide
(3S,18R,20S)-3-(Acetoxy)-N-methoxy-N-ethyl-11-oxo-olean-12-en-29-amide
(3S,18R,20S)-3-(Acetoxy)-N-methoxy-N-i-propyl-11-oxo-olean-12-en-29-amide
(3S,18R,20S)-3-(Acetoxy)-N-methoxy-N-t-butyl-11-oxo-olean-12-en-29-amide
(3S,18R,20S)-3-(Acetoxy)-N-methoxy-N-allyl-11-oxo-olean-12-en-29-amide
(3S,18R,20S)-3-(Acetoxy)-N-methoxy-N-ethynyl-11-oxo-olean-12-en-29-amide
(3S,18R,20S)-3-(Acetoxy)-N-methoxy-N-cyclopropyl-11-oxo-olean-12-en-29-amide
(3S,18R,20S)-3-(Acetoxy)-N-methoxy-N-cyclobutyl-11-oxo-olean-12-en-29-amide
(3S,18R,20S)-3-(Acetoxy)-N-methoxy-N-trifluoromethyl-11-oxo-olean-12-en-29-amide
(3S,18R,20S)-3-(Acetoxy)-N-methoxy-N-2-hydroxyethyl-11-oxo-olean-12-en-29-amide
(3S,18R,20S)-3-(Acetoxy)-N-ethoxy-N-ethyl-11-oxo-olean-12-en-29-amide
(3S,18R,20S)-3-(Acetoxy)-N-ethynyloxy-N-ethyl-11-oxo-olean-12-en-29-amide
(3S,18R,20S)-3-(Acetoxy)-N-cyclopropyloxy-N-ethyl-11-oxo-olean-12-en-29-amide (3S,18R,20S)-3-(Acetoxy)-N-trifluoromethoxy-N-ethyl-11-oxo-olean-12-en-29-amide
(3S,18R,20S)-3-(Acetoxy)-N-ethoxy-N-ethynyl-11-oxo-olean-12-en-29-amide
(3S,18R,20S)-3-(Acetoxy)-N-ethynyloxy-N-ethynyl-11-oxo-olean-12-en-29-amide
(3S,18R,20S)-3-(Acetoxy)-N-cyclopropyloxy-N-ethynyl-11-oxo-olean-12-en-29-amide
(3S,18R,20S)-3-(Acetoxy)-N-trifluoromethoxy-N-ethynyl-11-oxo-olean-12-en-29-amide
(3S,18R,20S)-3-(Acetoxy)-N-ethoxy-N-cyclopropyl-11-oxo-olean-12-en-29-amide
(3S,18R,20S)-3-(Acetoxy)-N-ethynyloxy-N-cyclopropyl-11-oxo-olean-12-en-29-amide
(3S,18R,20S)-3-(Acetoxy)-N-cyclopropyloxy-N-cyclopropyl-11-oxo-olean-12-en-29-amide
(3S,18R,20S)-3-(Acetoxy)-N-trifluoromethoxy-N-cyclopropyl-11-oxo-olean-12-en-29-amide
(3S,18R,20S)-3-(Acetoxy)-N-ethoxy-N-trifluoromethyl-11-oxo-olean-12-en-29-amide
(3S,18R,20S)-3-(Acetoxy)-N-ethynyloxy-N-trifluoromethyl-11-oxo-olean-12-en-29-amide
(3S,18R,20S)-3-(Acetoxy)-N-cyclopropyloxy-N-trifluoromethyl-11-oxo-olean-12-en-29-amide
(3S,18R,20S)-3-(Acetoxy)-N-trifluormethoxy-N-trifluoromethyl-11-oxo-olean-12-en-29-amide
(3S,18R,20S)-3-Hydroxy-N-ethoxy-11-oxo-olean-12-en-29-amide
(3S,18R,20S)-3-Hydroxy-N-i-propyloxy-11-oxo-olean-12-en-29-amide
(3S,18R,20S)-3-Hydroxy-N-t-butyloxy-11-oxo-olean-12-en-29-amide
(3S,18R,20S)-3-Hydroxy-N-allyloxy-11-oxo-olean-12-en-29-amide
(3S,18R,20S)-3-Hydroxy-N-ethynyloxy-11-oxo-olean-12-en-29-amide
(3S,18R,20S)-3-Hydroxy-N-cyclopropyloxy-11-oxo-olean-12-en-29-amide
(3S,18R,20S)-3-Hydroxy-N-cyclobutyloxy-11-oxo-olean-12-en-29-amide
(3S,18R,20S)-3-Hydroxy-N-trifluoromethoxy-11-oxo-olean-12-en-29-amide
(3S,18R,20S)-3-Hydroxy-N-(phenylmethoxy)-11-oxo-olean-12-en-29-amide
(3S,18R,20S)-3-Hydroxy-N-phenoxy-11-oxo-olean-12-en-29-amide
(3S,18R,20S)-3-Hydroxy-N-ethoxy-N-methyl-11-oxo-olean-12-en-29-amide
(3S,18R,20S)-3-Hydroxy-N-i-propyloxy-N-methyl-11-oxo-olean-12-en-29-amide
(3S,18R,20S)-3-Hydroxy-N-t-butyloxy-N-methyl-11-oxo-olean-12-en-29-amide
(3S,18R,20S)-3-Hydroxy-N-allyloxy-N-methyl-11-oxo-olean-12-en-29-amide
(3S,18R,20S)-3-Hydroxy-N-ethynyloxy-N-methyl-11-oxo-olean-12-en-29-amide
(3S,18R,20S)-3-Hydroxy-N-cyclopropyloxy-N-methyl-11-oxo-olean-12-en-29-amide
(3S,18R,20S)-3-Hydroxy-N-cyclobutyloxy-N-methyl-11-oxo-olean-12-en-29-amide
(3S,18R,20S)-3-Hydroxy-N-trifluoromethoxy-N-methyl-11-oxo-olean-12-en-29-amide
(3S,18R,20S)-3-Hydroxy-N-(phenylmethoxy)-N-methyl-11-oxo-olean-12-en-29-amide
(3S,18R,20S)-3-Hydroxy-N-phenoxy-N-methyl-11-oxo-olean-12-en-29-amide
(3S,18R,20S)-3-Hydroxy-N-hydroxy-N-ethyl-11-oxo-olean-12-en-29-amide
(3S,18R,20S)-3-Hydroxy-N-hydroxy-N-i-propyl-11-oxo-olean-12-en-29-amide
(3S,18R,20S)-3-Hydroxy-N-hydroxy-N-t-butyl-11-oxo-olean-12-en-29-amide
(3S,18R,20S)-3-Hydroxy-N-hydroxy-N-allyl-11-oxo-olean-12-en-29-amide
(3S,18R,20S)-3-Hydroxy-N-hydroxy-N-ethynyl-11-oxo-olean-12-en-29-amide
(3S,18R,20S)-3-Hydroxy-N-hydroxy-N-cyclopropyl-11-oxo-olean-12-en-29-amide
(3S,18R,20S)-3-Hydroxy-N-hydroxy-N-cyclobutyl-11-oxo-olean-12-en-29-amide
(3S,18R,20S)-3-Hydroxy-N-hydroxy-N-trifluoromethyl-11-oxo-olean-12-en-29-amide
(3S,18R,20S)-3-Hydroxy-N-hydroxy-N-2-hydroxyethyl-11-oxo-olean-12-en-29-amide
(3S,18R,20S)-3-Hydroxy-N-methoxy-N-ethyl-11-oxo-olean-12-en-29-amide
(3S,18R,20S)-3-Hydroxy-N-methoxy-N-i-propyl-11-oxo-olean-12-en-29-amide
(3S,18R,20S)-3-Hydroxy-N-methoxy-N-t-butyl-11-oxo-olean-12-en-29-amide
(3S,18R,20S)-3-Hydroxy-N-methoxy-N-allyl-11-oxo-olean-12-en-29-amide
(3S,18R,20S)-3-Hydroxy-N-methoxy-N-ethynyl-11-oxo-olean-12-en-29-amide
(3S,18R,20S)-3-Hydroxy-N-methoxy-N-cyclopropyl-11-oxo-olean-12-en-29-amide
(3S,18R,20S)-3-Hydroxy-N-methoxy-N-cyclobutyl-11-oxo-olean-12-en-29-amide
(3S,18R,20S)-3-Hydroxy-N-methoxy-N-trifluoromethyl-11-oxo-olean-12-en-29-amide
(3S,18R,20S)-3-Hydroxy-N-methoxy-N-2-hydroxyethyl-11-oxo-olean-12-en-29-amide
(3S,18R,20S)-3-Hydroxy-N-ethoxy-N-ethyl-11-oxo-olean-12-en-29-amide
(3S,18R,20S)-3-Hydroxy-N-ethynyloxy-N-ethyl-11-oxo-olean-12-en-29-amide
(3S,18R,20S)-3-Hydroxy-N-cyclopropyloxy-N-ethyl-11-oxo-olean-12-en-29-amide
(3S,18R,20S)-3-Hydroxy-N-trifluoromethoxy-N-ethyl-11-oxo-olean-12-en-29-amide
(3S,18R,20S)-3-Hydroxy-N-ethoxy-N-ethynyl-11-oxo-olean-12-en-29-amide
(3S,18R,20S)-3-Hydroxy-N-ethynyloxy-N-ethynyl-11-oxo-olean-12-en-29-amide
(3S,18R,20S)-3-Hydroxy-N-cyclopropyloxy-N-ethynyl-11-oxo-olean-12-en-29-amide
(3S,18R,20S)-3-Hydroxy-N-trifluoromethoxy-N-ethynyl-11-oxo-olean-12-en-29-amide
(3S,18R,20S)-3-Hydroxy-N-ethoxy-N-cyclopropyl-11-oxo-olean-12-en-29-amide
(3S,18R,20S)-3-Hydroxy-N-ethynyloxy-N-cyclopropyl-11-oxo-olean-12-en-29-amide
(3S,18R,20S)-3-Hydroxy-N-cyclopropyloxy-N-cyclopropyl-11-oxo-olean-12-en-29-amide
(3S,18R,20S)-3-Hydroxy-N-trifluoromethoxy-N-cyclopropyl-11-oxo-olean-12-en-29-amide
(3S,18R,20S)-3-Hydroxy-N-ethoxy-N-trifluoromethyl-11-oxo-olean-12-en-29-amide
(3S,18R,20S)-3-Hydroxy-N-ethynyloxy-N-trifluoromethyl-11-oxo-olean-12-en-29-amide
(3S,18R,20S)-3-Hydroxy-N-cyclopropyloxy-N-trifluoromethyl-11-oxo-olean-12-en-29-amide (3S,18R,20S)-3-Hydroxy-N-trifluoromethoxy-N-trifluoromethyl-11-oxo-olean-12-en-29-amide
(3S,18R,20S)-3-Amino-N-ethoxy-11-oxo-olean-12-en-29-amide
(3S,18R,20S)-3-Amino-N-i-propyloxy-11-oxo-olean-12-en-29-amide
(3S,18R,20S)-3-Amino-N-t-butyloxy-11-oxo-olean-12-en-29-amide
(3S,18R,20S)-3-Amino-N-allyloxy-11-oxo-olean-12-en-29-amide
(3S,18R,20S)-3-Amino-N-ethynyloxy-11-oxo-olean-12-en-29-amide
(3S,18R,20S)-3-Amino-N-cyclopropyloxy-11-oxo-olean-12-en-29-amide
(3S,18R,20S)-3-Amino-N-cyclobutyloxy-11-oxo-olean-12-en-29-amide
(3S,18R,20S)-3-Amino-N-trifluoromethoxy-11-oxo-olean-12-en-29-amide
(3S,18R,20S)-3-Amino-N-(phenylmethoxy)-11-oxo-olean-12-en-29-amide
(3S,18R,20S)-3-Amino-N-phenoxy-11-oxo-olean-12-en-29-amide
(3S,18R,20S)-3-Amino-N-ethoxy-N-methyl-11-oxo-olean-12-en-29-amide
(3S,18R,20S)-3-Amino-N-i-propyloxy-N-methyl-11-oxo-olean-12-en-29-amide
(3S,18R,20S)-3-Amino-N-t-butyloxy-N-methyl-11-oxo-olean-12-en-29-amide
(3S,18R,20S)-3-Amino-N-allyloxy-N-methyl-11-oxo-olean-12-en-29-amide
(3S,18R,20S)-3-Amino-N-ethynyloxy-N-methyl-11-oxo-olean-12-en-29-amide
(3S,18R,20S)-3-Amino-N-cyclopropyloxy-N-methyl-11-oxo-olean-12-en-29-amide
(3S,18R,20S)-3-Amino-N-cyclobutyloxy-N-methyl-11-oxo-olean-12-en-29-amide
(3S,18R,20S)-3-Amino-N-trifluoromethoxy-N-methyl-11-oxo-olean-12-en-29-amide
(3S,18R,20S)-3-Amino-N-(phenylmethoxy)-N-methyl-11-oxo-olean-12-en-29-amide
(3S,18R,20S)-3-Amino-N-phenoxy-N-methyl-11-oxo-olean-12-en-29-amide
(3S,18R,20S)-3-Amino-N-hydroxy-N-ethyl-11-oxo-olean-12-en-29-amide
(3S,18R,20S)-3-Amino-N-hydroxy-N-i-propyl-11-oxo-olean-12-en-29-amide
(3S,18R,20S)-3-Amino-N-hydroxy-N-t-butyl-11-oxo-olean-12-en-29-amide
(3S,18R,20S)-3-Amino-N-hydroxy-N-allyl-11-oxo-olean-12-en-29-amide
(3S,18R,20S)-3-Amino-N-hydroxy-N-ethynyl-11-oxo-olean-12-en-29-amide
(3S,18R,20S)-3-Amino-N-hydroxy-N-cyclopropyl-11-oxo-olean-12-en-29-amide
(3S,18R,20S)-3-Amino-N-hydroxy-N-cyclobutyl-11-oxo-olean-12-en-29-amide
(3S,18R,20S)-3-Amino-N-hydroxy-N-trifluoromethyl-11-oxo-olean-12-en-29-amide
(3S,18R,20S)-3-Amino-N-hydroxy-N-2-hydroxyethyl-11-oxo-olean-12-en-29-amide
(3S,18R,20S)-3-Amino-N-methoxy-N-ethyl-11-oxo-olean-12-en-29-amide
(3S,18R,20S)-3-Amino-N-methoxy-N-i-propyl-11-oxo-olean-12-en-29-amide
(3S,18R,20S)-3-Amino-N-methoxy-N-t-butyl-11-oxo-olean-12-en-29-amide
(3S,18R,20S)-3-Amino-N-methoxy-N-allyl-11-oxo-olean-12-en-29-amide
(3S,18R,20S)-3-Amino-N-methoxy-N-ethynyl-11-oxo-olean-12-en-29-amide
(3S,18R,20S)-3-Amino-N-methoxy-N-cyclopropyl-11-oxo-olean-12-en-29-amide
(3S,18R,20S)-3-Amino-N-methoxy-N-cyclobutyl-11-oxo-olean-12-en-29-amide
(3S,18R,20S)-3-Amino-N-methoxy-N-trifluoromethyl-11-oxo-olean-12-en-29-amide
(3S,18R,20S)-3-Amino-N-methoxy-N-2-hydroxyethyl-11-oxo-olean-12-en-29-amide
(3S,18R,20S)-3-Amino-N-ethoxy-N-ethyl-11-oxo-olean-12-en-29-amide
(3S,18R,20S)-3-Amino-N-ethynyloxy-N-ethyl-11-oxo-olean-12-en-29-amide
(3S,18R,20S)-3-Amino-N-cyclopropyloxy-N-ethyl-11-oxo-olean-12-en-29-amide
(3S,18R,20S)-3-Amino-N-trifluoromethoxy-N-ethyl-11-oxo-olean-12-en-29-amide
(3S,18R,20S)-3-Amino-N-ethoxy-N-ethynyl-11-oxo-olean-12-en-29-amide
(3S,18R,20S)-3-Amino-N-ethynyloxy-N-ethynyl-11-oxo-olean-12-en-29-amide
(3S,18R,20S)-3-Amino-N-cyclopropyloxy-N-ethynyl-11-oxo-olean-12-en-29-amide
(3S,18R,20S)-3-Amino-N-trifluoromethoxy-N-ethynyl-11-oxo-olean-12-en-29-amide
(3S,18R,20S)-3-Amino-N-ethoxy-N-cyclopropyl-11-oxo-olean-12-en-29-amide
(3S,18R,20S)-3-Amino-N-ethynyloxy-N-cyclopropyl-11-oxo-olean-12-en-29-amide
(3S,18R,20S)-3-Amino-N-cyclopropyloxy-N-cyclopropyl-11-oxo-olean-12-en-29-amide
(3S,18R,20S)-3-Amino-N-trifluoromethoxy-N-cyclopropyl-11-oxo-olean-12-en-29-amide
(3S,18R,20S)-3-Amino-N-ethoxy-N-trifluoromethyl-11-oxo-olean-12-en-29-amide
(3S,18R,20S)-3-Amino-N-ethynyloxy-N-trifluoromethyl-11-oxo-olean-12-en-29-amide
(3S,18R,20S)-3-Amino-N-cyclopropyloxy-N-trifluoromethyl-11-oxo-olean-12-en-29-amide
(3S,18R,20S)-3-Amino-N-trifluoromethoxy-N-trifluoromethyl-11-oxo-olean-12-en-29-amide
(3S,18R,20S)-3-(Acetamino)-N-ethoxy-11-oxo-olean-12-en-29-amide
(3S,18R,20S)-3-(Acetamino)-N-i-propyloxy-11-oxo-olean-12-en-29-amide
(3S,18R,20S)-3-(Acetamino)-N-t-butyloxy-11-oxo-olean-12-en-29-amide
(3S,18R,20S)-3-(Acetamino)-N-allyloxy-11-oxo-olean-12-en-29-amide
(3S,18R,20S)-3-(Acetamino)-N-ethynyloxy-11-oxo-olean-12-en-29-amide
(3S,18R,20S)-3-(Acetamino)-N-cyclopropyloxy-11-oxo-olean-12-en-29-amide
(3S,18R,20S)-3-(Acetamino)-N-cyclobutyloxy-11-oxo-olean-12-en-29-amide
(3S,18R,20S)-3-(Acetamino)-N-trifluoromethoxy-11-oxo-olean-12-en-29-amide
(3S,18R,20S)-3-(Acetamino)-N-(phenylmethoxy)-11-oxo-olean-12-en-29-amide
(3S,18R,20S)-3-(Acetamino)-N-phenoxy-11-oxo-olean-12-en-29-amide
(3S,18R,20S)-3-(Acetamino)-N-ethoxy-N-methyl-11-oxo-olean-12-en-29-amide (3S,18R,20S)-3-(Acetamino)-N-i-propyloxy-N-methyl-11-oxo-olean-12-en-29-amide
(3S,18R,20S)-3-(Acetamino)-N-t-butyloxy-N-methyl-11-oxo-olean-12-en-29-amide
(3S,18R,20S)-3-(Acetamino)-N-allyloxy-N-methyl-11-oxo-olean-12-en-29-amide
(3S,18R,20S)-3-(Acetamino)-N-ethynyloxy-N-methyl-11-oxo-olean-12-en-29-amide
(3S,18R,20S)-3-(Acetamino)-N-cyclopropyloxy-N-methyl-11-oxo-olean-12-en-29-amide
(3S,18R,20S)-3-(Acetamino)-N-cyclobutyloxy-N-methyl-11-oxo-olean-12-en-29-amide
(3S,18R,20S)-3-(Acetamino)-N-trifluoromethoxy-N-methyl-11-oxo-olean-12-en-29-amide
(3S,18R,20S)-3-(Acetamino)-N-(phenylmethoxy)-N-methyl-11-oxo-olean-12-en-29-amide
(3S,18R,20S)-3-(Acetamino)-N-phenoxy-N-methyl-11-oxo-olean-12-en-29-amide
(3S,18R,20S)-3-(Acetamino)-N-hydroxy-N-ethyl-11-oxo-olean-12-en-29-amide
(3S,18R,20S)-3-(Acetamino)-N-hydroxy-N-i-propyl-11-oxo-olean-12-en-29-amide
(3S,18R,20S)-3-(Acetamino)-N-hydroxy-N-t-butyl-11-oxo-olean-12-en-29-amide
(3S,18R,20S)-3-(Acetamino)-N-hydroxy-N-allyl-11-oxo-olean-12-en-29-amide
(3S,18R,20S)-3-(Acetamino)-N-hydroxy-N-ethynyl-11-oxo-olean-12-en-29-amide
(3S,18R,20S)-3-(Acetamino)-N-hydroxy-N-cyclopropyl-11-oxo-olean-12-en-29-amide
(3S,18R,20S)-3-(Acetamino)-N-hydroxy-N-cyclobutyl-11-oxo-olean-12-en-29-amide
(3S,18R,20S)-3-(Acetamino)-N-hydroxy-N-trifluoromethyl-11-oxo-olean-12-en-29-amide
(3S,18R,20S)-3-(Acetamino)-N-hydroxy-N-2-hydroxyethyl-11-oxo-olean-12-en-29-amide
(3S,18R,20S)-3-(Acetamino)-N-methoxy-N-ethyl-11-oxo-olean-12-en-29-amide
(3S,18R,20S)-3-(Acetamino)-N-methoxy-N-i-propyl-11-oxo-olean-12-en-29-amide
(3S,18R,20S)-3-(Acetamino)-N-methoxy-N-t-butyl-11-oxo-olean-12-en-29-amide
(3S,18R,20S)-3-(Acetamino)-N-methoxy-N-allyl-11-oxo-olean-12-en-29-amide
(3S,18R,20S)-3-(Acetamino)-N-methoxy-N-ethynyl-11-oxo-olean-12-en-29-amide
(3S,18R,20S)-3-(Acetamino)-N-methoxy-N-cyclopropyl-11-oxo-olean-12-en-29-amide
(3S,18R,20S)-3-(Acetamino)-N-methoxy-N-cyclobutyl-11-oxo-olean-12-en-29-amide
(3S,18R,20S)-3-(Acetamino)-N-methoxy-N-trifluoromethyl-11-oxo-olean-12-en-29-amide
(3S,18R,20S)-3-(Acetamino)-N-methoxy-N-2-hydroxyethyl-11-oxo-olean-12-en-29-amide
(3S,18R,20S)-3-(Acetamino)-N-ethoxy-N-ethyl-11-oxo-olean-12-en-29-amide
(3S,18R,20S)-3-(Acetamino)-N-ethynyloxy-N-ethyl-11-oxo-olean-12-en-29-amide
(3S,18R,20S)-3-(Acetamino)-N-cyclopropyloxy-N-ethyl-11-oxo-olean-12-en-29-amide
(3S,18R,20S)-3-(Acetamino)-N-trifluoromethoxy-N-ethyl-11-oxo-olean-12-en-29-amide
(3S,18R,20S)-3-(Acetamino)-N-ethoxy-N-ethynyl-11-oxo-olean-12-en-29-amide
(3S,18R,20S)-3-(Acetamino)-N-ethynyloxy-N-ethynyl-11-oxo-olean-12-en-29-amide
(3S,18R,20S)-3-(Acetamino)-N-cyclopropyloxy-N-ethynyl-11-oxo-olean-12-en-29-amide
(3S,18R,20S)-3-(Acetamino)-N-trifluoromethoxy-N-ethynyl-11-oxo-olean-12-en-29-amide
(3S,18R,20S)-3-(Acetamino)-N-ethoxy-N-cyclopropyl-11-oxo-olean-12-en-29-amide
(3S,18R,20S)-3-(Acetamino)-N-ethynyloxy-N-cyclopropyl-11-oxo-olean-12-en-29-amide
(3S,18R,20S)-3-(Acetamino)-N-cyclopropyloxy-N-cyclopropyl-11-oxo-olean-12-en-29-amide
(3S,18R,20S)-3-(Acetamino)-N-trifluoromethoxy-N-cyclopropyl-11-oxo-olean-12-en-29-amide
(3S,18R,20S)-3-(Acetamino)-N-ethoxy-N-trifluoromethyl-11-oxo-olean-12-en-29-amide
(3S,18R,20S)-3-(Acetamino)-N-ethynyloxy-N-trifluoromethyl-11-oxo-olean-12-en-29-amide
(3S,18R,20S)-3-(Acetamino)-N-cyclopropyloxy-N-trifluoromethyl-11-oxo-olean-12-en-29-amide
(3S,18R,20S)-3-(Acetamino)-N-trifluoromethoxy-N-trifluoromethyl-11-oxo-olean-12-en-29-amide Example 38

Effects of Compounds on the Activity of 11β-HSD

Cell culture media were purchased from Invitrogen, Basel, Switzerland. [1,2,6,7-3H]-cortisol was from Amersham Pharmacia, Dubendorf, Switzerland. [1,2,6,7-3H]-cortisone was produced by incubating 1 mCi of [1,2,6,7-3H]-cortisol with 1 mg of lysate of HEK-293 cells expressing 11β-HSD2 in the presence of 1 mM NAD+. Incubation was for 16 h at 37° C. The steroids were extracted with ethylacetate, separated by thin layer chromatography (TLC) (SIL G-25 UV254, Macherey-Nagel, Oensingen, Switzerland) using a solvent system of 9:1 (v/v) chloroform:methanol and the band corresponding to cortisone was excised. The product was run for a second chromatographic purification step on the same TLC system. A total of 250 µCi of [1,2,6,7-3H]-cortisone was recovered. G-418 sulfate was from Promega, Wallisellen, Switzerland. All other chemicals were from Fluka AG, Buchs, Switzerland and were of the highest grade available.

Untransfected HEK-293 cells do not express 11β-HSD1 activity. 11β-HSD2 mRNA was detectable by RT-PCR, but activity was not detectable upon incubation of radiolabeled cortisol with cell lysate for 8 h. HEK-293 cells were transfected with the plasmid for expression of carboxy-terminally FLAG-epitope tagged 11β-HSD1 or 11β-HSD2, respectively, that were described previously [18]. Transfected cells were selected by cultivation in presence of 800 µg/mL of G-418. Non-resistant cells were removed by replacing the cell culture medium every third day for 3 weeks. From these cells, eight clones each were then selected and tested for protein expression, by immunofluorescence analysis using mouse monoclonal anti-FLAG antibody M2 (Sigma) and goat anti-mouse antibody ALEXA 488, and 11β-HSD activity. All of the eight clones of either 11β-HSD1 or 11β-HSD2 transfected cells showed similar expression and activity of the corresponding FLAG-epitope tagged 11β-HSD construct.

HEK-293 cells stably transfected with either 11β-HSD1 or 11β-HSD2 were grown in 10 cm dishes to 90% confluence. Cells were rinsed once with phosphate-buffered saline and resuspended in 2 mL of ice-cold buffer TS2 containing 100 mM NaCl, 1 mM EGTA, 1 mM EDTA, 1 mM MgCl$_2$, 250 mM sucrose, 20 mM Tris-HCl, pH 7.4. For determination of oxidative activity of 11β-HSD enzymes, cells were lysed by sonication and the cell lysate was diluted 1:12 in buffer TS2 (at 4° C.). Reactions were carried out in 96-well optical PCR reaction plates (Applied Biosystems, Foster City, Calif.) and tubes were capped during the reaction to avoid evaporation. Reactions were started by simultaneously adding 10 μL of cell lysate and 10 μL of TS2 buffer containing the appropriate concentration of the compound to be tested to 10 μL of TS2 buffer containing NAD+, 30 nCi of [1,2,6,7-3H]-cortisol and unlabeled cortisol to give a final concentration of 400 μM NAD+ and 10 nM cortisol. Stock solutions of the compounds in methanol or in DMSO were diluted in TS2 buffer to yield the appropriate concentrations, whereby the concentration of methanol or DMSO in the reactions was below 0.1%. Control reactions with or without 0.1% of the solvent showed the same activity. After incubation at 37° C. for 10 min with shaking, 10 μL of stop solution containing 2 mMol unlabeled cortisol and cortisone dissolved in methanol were added. Conversion of radiolabeled cortisol was determined by separation of cortisol and cortisone using TLC and a solvent system of 9:1 (v/v) chloroform:methanol, followed by scintillation counting [19]. In absence of inhibitors approximately 40% of cortisol was converted to cortisone.

Similarly, reductase activity was measured in a reaction containing NADPH, 30 nCi of [1,2,6,7-3H]-cortisone and unlabeled cortisone, whereby final concentrations were 400 μM NADPH and 10 nM cortisone. No loss of 11β-HSD2 activity was observed upon freezing of cell lysates for up to 1 month. In contrast, 11β-HSD1 activity declined after cell disruption, with a concomitant loss of affinity for its substrate but without any significant loss of apparent Vmax. Activities were determined measuring the conversion of either radiolabeled cortisone or cortisol for 5-20 min using substrate concentrations in the range between 10 nM and 10 μM. 11β-HSD1 activities were measured immediately after cell disruption. All measurements included a negative control in absence of environmental compound and a positive control containing glycyrrhetinic acid at a final concentration of 10 μM. Results are expressed as mean±S.D. and consist of at least three independent measurements.

| Compound | Concentration (nmol/L) | Reduction of 11β-HSD1 Activity (%) (average ± standard deviation) | Reduction of 11β-HSD2 Activity (%) (average ± standard deviation) |
|---|---|---|---|
| 1* | 1000 | 51.7 ± 8.3 | 98.8 ± 1.9 |
| 2** | 1000 | 46.7 ± 13.8 | 98.5 ± 1.5 |
| 4 | 200 | 5.1 +− 21.8 | 28.3 +− 1.2 |
| 6 | 200 | 3.3 +− 3.9 | 95.8 +− 5 |
| 6 | 1000 | 49.5 ± 10.9 | 97.4 ± 1.4 |
| 7 | 200 | 29.4 +− 12.6 | 93.4 +− 1.5 |
| 10 | 200 | 6.7 +− 9.4 | 70.5 +− 18.2 |
| 13 | 200 | 1 +− 12.1 | 15.6 +− 1.6 |
| 16 | 1000 | 62.1 +− 9.2 | 64.3 +− 41.3 |
| 27 | 200 | 28.4 +− 12.2 | 96.4 +− 3 |
| 33 | 200 | 29.4 +− 27.2 | 55.7 +− 38.3 |
| 34 | 200 | 12 +− 7.7 | 17.7 +− 2.7 |
| 35 | 200 | 14.4 +− 3.4 | 14.9 +− 13.5 |

| Compound | 11β-HSD1 IC$_{50}$ (nmol/L) | 11β-HSD2 IC$_{50}$ (nmol/L) | IC$_{50}$ 11β-HSD1/11β-HSD2 |
|---|---|---|---|
| 1* | 627 | 60 | 10.4 |
| 2** | 1156 | 122 | 9.5 |
| 6 | 1012 | 7 | 153.1 |
| 10 | >40000 | 547 | >73.1 |
| 16 | 929 | 2128 | 0.4 |

*(3S,18R,20S)-3-(Acetyloxy)-N-hydroxy-11-oxo-olean-12-en-29-amide CAS Registry Number: 30292-62-7 [20]

**(3S,18R,20S)-3-(Hydroxy)-N-hydroxy-11-oxo-olean-12-en-29-amide CAS Registry Number: 863323-50-6 [23]

Compound 6 was tested in an assay using intact cells similar to the one described above for cell lysates. The IC$_{50}$ value in these experiments was calculated to more than 20 μM for 11β-HSD1 and 2.1 μM for 11β-HSD2. In addition compound 6 was tested against murine 11β-HSD2 in a lysate assay as described above for human 11β-HSD2 where compound 6 showed an IC$_{50}$ of 0.027 μM.

Reference List:

[1] R. A. Isbrucker, G. A. Burdock, Regul Toxicol Pharmacol 46 (2006) 167-192.

[2] N. Nassiri Asl, H. Hosseinzadeh, Journal of Medicinal Plants 6 (2007) 1-12.

[3] M. Nassiri Asl, H. Hosseinzadeh, Phytotherapy Research 22 (2008) 709-724.

[4] F. Andersen, International Journal of Toxicology 26 (2007) 79-112.

[5] J. Rios et al., Studies in Natural Product Chemistry 22 (2000) 93-143.

[6] Y. H. Zhang et al., Immunology. 79 (1993) 528-534.

[7] Y. H. Zhang et al., Cell. Immunol. 162 (1995) 97-104.

[8] K. C. Nicolaou et al., JAGS124 (2002) 2245-2258.

[9] R. A. Schweizer et al., Mol. Cell. Endocrinol. 212 (2003) 41-49.

[10] X. Su et al., J. Steroid Biochem. Mol. Biol. 104 (2007) 312-320.

[11] S. Diederich et al., Eur. J. Endocrinol. 142 (2000) 200-207.

[12] S. A. Latif et al., Mol. Cell. Endocrinol. 243 (2005) 43-50.

[13] A. Ukil et al., J. Immunol. 175 (2005) 1161-1169.

[14] N. Abe, T. Ebina, N. Ishida, Microbiol. Immunol. 26 (1982) 535-539.

[15] R. C. Rowe, P. J. Sheskey, S. C. Owen, Handbook of Pharmaceutical Excipients, 5 ed., Pharmaceutical Press, London, Chicago, 2006.

[16] United States Pharmacopeia, USP NF 2008 (United States Pharmacopeia/National Formulary), 2008.

[17] European Directorate for the Quality of Medicines & HealthCare (EDQM), European Pharmacopoeia, 2008.

[18] A. Odermatt et al., J. Biol. Chem. 274 (1999) 28762-28770.

[19] G. Escher et al., J. Exp. Med. 186 (1997) 189-198.

[20] D. Schuster et al., J. Med. Chem. 49 (2006) 3454-3466.

[21] X. Su et al., Bioorg. & Med. Chem. 12 (2004) 4439-4457.

[22] C. Brieskorn et al., Archiv der 303 (1970) 901-4.

[23] A. Ech-Chahad et al. Tetrahedron Letters 46 (2005) 5113-5115.

[24] W. J. Boyle et al., Nature 423 (2003) 337-342.

[25] T. Suda et al., Bone 17 (1995)

The invention claimed is:

1. A compound having the following general structural formula I,

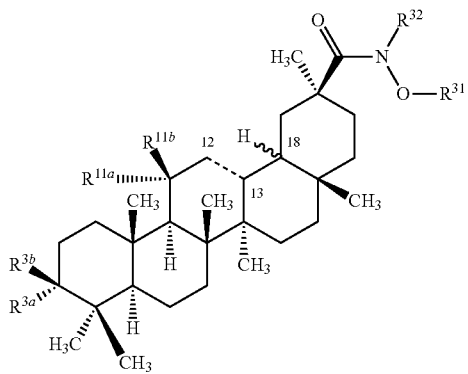

wherein:

R$^{3a}$ and R$^{3b}$ together are selected from =O, =NR$^a$, =N—O—R$^a$; or R$^{3a}$ and R$^{3b}$ are independently from one another selected from hydrogen, —O—R$^a$, —O—C(=O)—R$^a$, —NH—R$^a$, —NH—O—R$^a$, —NH—C(=O)—R$^a$ and —NH—S(=O)$_2$R$^a$; and R$^{11a}$ and R$^{11b}$ together are selected from =O, =NR$^a$, =N—O—R$^a$; or R$^{11a}$ and R$^{11b}$ are independently from one another selected from hydrogen, —O—R$^a$, —O—C(=O)—R$^a$, —NH—R$^a$, methyl, ethyl, ethynyl, fluorine, chlorine, and bromine; and a single or double bond is present at 12-13;

R$^{31}$ is selected from hydrogen, hydroxyalkyl, C$_{1-6}$ alkyl, C$_{2-6}$ alkenyl, C$_{2-8}$ alkynyl, —CF$_3$, —(CH$_2$)$_n$—C$_{6-14}$ aryl, —CH=CH—C$_{6-14}$ aryl, —C≡C—C$_{6-14}$ aryl, —(CH$_2$)$_n$—C$_{5-14}$ heteroaryl, —CH=CH—C$_{5-14}$ heteroaryl, —C≡C—C$_{5-14}$ heteroaryl, carboxylic acid, —(CH$_2$)$_n$—C$_{3-8}$ cycloalkyl, —CH=CH—C$_{3-8}$ cycloalkyl and —C≡C—C$_{3-8}$ cycloalkyl; and R$^{32}$ is hydrogen or selected from optionally substituted hydroxyalkyl, C$_{1-6}$ alkyl, C$_{2-6}$ alkenyl, C$_{2-8}$ alkynyl, —CF$_3$, —(CH$_2$)$_n$—C$_{6-14}$ aryl, —CH=CH—C$_{6-14}$ aryl, —C≡C—C$_{6-14}$ aryl, —(CH$_2$)$_n$—C$_{5-14}$ heteroaryl, —CH=CH—C$_{5-14}$heteroaryl, —C≡C—C$_{5-14}$ heteroaryl, carboxylic acid, —(CH$_2$)$_n$—C$_{3-8}$ cycloalkyl, —CH=CH—C$_{3-8}$cycloalkyl and —C≡C—C$_{3-8}$cycloalkyl;

R$^a$ is selected from hydrogen, hydroxyalkyl, C$_{1-6}$ alkyl, C$_{2-6}$ alkenyl, C$_{2-8}$ alkynyl, —CF$_3$, —(CH$_2$)$_n$—C$_{6-14}$ aryl, —CH=CH—C$_{6-14}$ aryl, —C≡C—C$_{6-14}$ aryl, —(CH$_2$)$_n$—C$_{5-14}$heteroaryl, —CH=CH—C$_{5-14}$heteroaryl, —C≡C—C$_{5-14}$heteroaryl, carboxylic acid, —(CH$_2$)$_n$—C$_{3-8}$cycloalkyl, —CH=CH—C$_{3-8}$cycloalkyl and —C≡C—C$_{3-8}$cycloalkyl; and each n independently of one another denotes 0, 1 or 2, including pharmaceutically effective salts, solvates, prodrugs, tautomers, racemates, enantiomers, diastereomers and mixtures thereof, with the proviso that compounds (3S, 18R, 20S)-3-(acetyloxy)-N-hydroxy-11-oxo-olean-12-en-29-amide and (3S, 18R, 20S)-3-(hydroxy)-N-hydroxy-11-oxo-olean-12-en-29-amide are not encompassed.

2. The compound of claim 1, wherein
R$^{11a}$ and R$^{11b}$ together denotes =O; and
a double bond is present at 12-13.

3. The compound of claim 1, wherein $R^{31}$ is selected from the group consisting of hydrogen, $C_{1-6}$ alkyl, $C_{2-6}$ alkenyl, $C_{2-8}$ alkynyl, —$CF_3$, —$(CH_2)_n$—$C_{6-14}$ aryl, —$(CH_2)_n$—$C_{5-14}$ heteroaryl and —$(CH_2)_n$—$C_{3-8}$cycloalkyl.

4. The compound of claim 1, wherein $R^{32}$ is selected from the group consisting of hydrogen, substituted hydroxyalkyl, $C_{1-6}$alkyl, $C_{2-6}$alkenyl, $C_{2-8}$alkynyl, —$CF_3$, —$(CH_2)_n$—$C_{6-14}$ aryl, —$(CH_2)_n$—$C_{5-14}$heteroaryl and —$(CH_2)_n$—$C_{3-8}$cycloalkyl.

5. The compound of claim 4, wherein $R^{32}$ is selected from the group consisting of hydrogen, methyl, ethyl, n-propyl, i-propyl, allyl, ethynyl, 2-hydroxyethyl, 3-hydroxypropyl, cyclopropyl and cyclobutyl.

6. The compound of claim 1, wherein $R^{3a}$ is hydrogen and $R^{3b}$ is selected from the group consisting of —O—$R^a$, —O—C(=O)—$R^a$, —NH—$R^a$, —NH—O—$R^a$, —NH—C(=O)—$R^a$ and —NH—S(=O)$_2R^a$.

7. The compound of claim 6, wherein $R^{3b}$ is selected from the group consisting of —OH, —O—acetyl, —O—succinyl, —NH$_2$, —NH—acetyl, —NH—succinyl, —NH—S(O)$_2$CF$_3$, —NH—S(O)$_2$CH$_3$ and —NH—S(O)$_2$CH$_2$CH$_2$COOH.

8. The compound of claim 1, wherein $R^{3b}$ is hydrogen and $R^{3a}$ is selected from the group consisting of —O—$R^a$, —O—C(=O)—$R^a$, —NH—$R^a$, —NH—O—$R^a$, —NH—C(=O)—$R^a$ and —NH—S(=O)$_2R^a$.

9. The compound of claim 8, wherein $R^{3a}$ is selected from the group consisting of —OH, —O—acetyl, —O—succinyl, —NH$_2$, —NH—acetyl, —NH—succinyl, —NH—S(O)$_2$CF$_3$, —NH—S(O)$_2$CH$_3$ and —NH—S(O)$_2$CH$_2$CH$_2$COOH.

10. The compound of claim 1, wherein $R^{3a}$ and $R^{3b}$ together are selected from the group consisting of oxo, imino and =N—O—$R^a$.

11. The compound of claim 10, wherein $R^a$ is hydrogen or methyl.

12. The compound of claim 1, wherein the compound is selected from the group consisting of:
   (3S, 18R, 20S)-3-(Acetyloxy)-N-hydroxy-N-methyl-11-oxo-olean-12-en-29-amide;
   (3S, 18R, 20S)-3-Hydroxy-N-methoxy-11-oxo-olean-12-en-29-amide;
   (3S, 18R, 20S)-3-(Acetyloxy)-N-methoxy-11-oxo-olean-12-en-29-amide;
   (3S, 18R, 20S)-3-(Acetyloxy)-N-methyl-N-methoxy-11-oxo-olean-12-en-29-amide;
   (3S, 18R, 20S)-3-Hydroxy-N-methyl-N-methoxy-11-oxo-olean-12-en-29-amide;
   (3S, 18R, 20S)-3-Hydroxy-N-(2-propen-l-yloxy)-11-oxo-olean-12-en-29-amide;
   (3S, 18R, 20S)-3-(Acetyloxy)-N-(2-propen-l-yloxy)-11-oxo-olean-12-en-29-amide;
   (3S, 18R, 20S)-3-Hydroxy-N-(1,1-dimethylethoxy)-11-oxo-olean-12-en-29-amide;
   (3S, 18R, 20S)-3-(Acetyloxy)-N-(1,1-dimethylethoxy)-11-oxo-olean-12-en-29-amide;
   (3S, 18R, 20S)-3-Hydroxy-N-(phenylmethoxy)-11-oxo-olean-12-en-29-amide;
   (3S, 18R, 20S)-3-(Acetyloxy)-N-(phenylmethoxy)-11-oxo-olean-12-en-29-amide;
   (3S, 18R, 20S)-3-Hydroxy-N-phenoxy-11-oxo-olean-12-en-29-amide;
   (3S, 18R, 20S)-3-(Acetyloxy)-N-phenoxy-11-oxo-olean-12-en-29-amide;
   (3S, 18R, 20S)-3-(Acetamino)-N-benzyloxy-11-oxo-olean-12-en-29-amide;
   (3S, 18R, 20S)-3-(Acetamino)-N-hydroxy-11-oxo-olean-12-en-29-amide;
   (3R, 18R, 20S)-3-(Acetamino)-N-benzyloxy-11-oxo-olean-12-en-29-amide;
   (3R, 18R, 20S)-3-(Acetamino)-N-hydroxy-11-oxo-olean-12-en-29-amide;
   (18R, 20S)-3-imino-N-Hydroxy-11-oxo-olean-12-en-29-amide; and
   (18R, 20S)-N-Hydroxy-3,11-dioxo-olean-12-en-29-amide.

13. A pharmaceutical preparation comprising the compound of claim 1 and one or more pharmaceutically acceptable excipients and/or carriers.

14. A method of treating one or more diseases selected from the group consisting of chronic inflammatory diseases, autoimmune diseases, skin diseases, bone diseases, metabolic diseases, and infectious diseases by administering a therapeutically effective amount of the compound of claim 1 to a subject in need thereof.

* * * * *